United States Patent
Choi et al.

(10) Patent No.: US 9,735,376 B2
(45) Date of Patent: Aug. 15, 2017

(54) ORGANOMETALLIC COMPOUND AND ORGANIC LIGHT-EMITTING DEVICE INCLUDING THE SAME

(71) Applicant: Samsung Electronics Co., Ltd., Suwon-si, Gyeonggi-do (KR)

(72) Inventors: Jongwon Choi, Yongin-si (KR); Yoonhyun Kwak, Seoul (KR); Ohyun Kwon, Yongin-si (KR); Sangdong Kim, Hwaseong-si (KR); Bumwoo Park, Seoul (KR); Youngjae Park, Seoul (KR); Sunyoung Lee, Seoul (KR)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 290 days.

(21) Appl. No.: 14/661,064

(22) Filed: Mar. 18, 2015

(65) Prior Publication Data

US 2016/0118604 A1  Apr. 28, 2016

(30) Foreign Application Priority Data

Oct. 22, 2014 (KR) .................. 10-2014-0143604

(51) Int. Cl.
  *C07F 15/00* (2006.01)
  *H01L 29/08* (2006.01)
  *H01L 51/00* (2006.01)
  *C07F 19/00* (2006.01)
  *H01L 51/50* (2006.01)

(52) U.S. Cl.
  CPC ...... *H01L 51/0085* (2013.01); *C07F 15/0033* (2013.01); *C07F 19/00* (2013.01); *H01L 51/5012* (2013.01)

(58) Field of Classification Search
  CPC .. H01L 51/0085; H01L 51/5012; C07F 19/00; C07F 15/0033
  USPC .................................................. 546/4; 257/40
  See application file for complete search history.

(56) References Cited

U.S. PATENT DOCUMENTS

| 6,465,115 | B2 | 10/2002 | Shi et al. |
| 6,596,415 | B2 | 7/2003 | Shi et al. |
| 2001/0019782 | A1 | 9/2001 | Igarashi et al. |
| 2008/0309228 | A1 | 12/2008 | Watanabe et al. |

(Continued)

FOREIGN PATENT DOCUMENTS

| JP | 5127300 | 5/1993 |
| JP | 20121517 | 1/2012 |

(Continued)

OTHER PUBLICATIONS

Hong Zhi Xie, et al., "Reduction of Self-Quenching Effect in Organic Electrophosphorescence Emitting Devices via the Use of Sterically Hindered Spacers in Phosphorescence Molecules", Adv. Mater. 2001, 13, No. 16, Aug. 16.

(Continued)

*Primary Examiner* — William Cheung
(74) *Attorney, Agent, or Firm* — Cantor Colburn LLP

(57) ABSTRACT

An organometallic compound represented by Formula 1:

$$M(L_1)_{n1}(L_2)_{n2}(L_3)_{n3} \qquad \text{Formula 1}$$

wherein in Formula 1, M, $L_1$, $L_2$, $L_3$, n1, n2, and n3 are the same as defined in the specification.

20 Claims, 1 Drawing Sheet

(56) References Cited

U.S. PATENT DOCUMENTS

| | | | |
|---|---|---|---|
| 2011/0037056 A1* | 2/2011 | Dubois | C09K 11/06 257/40 |
| 2011/0198580 A1* | 8/2011 | Herron | H01L 51/0072 257/40 |
| 2012/0299468 A1 | 11/2012 | Tsai et al. | |

FOREIGN PATENT DOCUMENTS

| | | | |
|---|---|---|---|
| WO | 2011032626 A1 | 3/2011 | |
| WO | 2014023377 A2 | 2/2014 | |

OTHER PUBLICATIONS

Raymond C. Kwong et al., "High Operational stability of electrophosphorescent devices", Applied Physics Letters 81, 162 (2002).

Sergey Lamansky et al., "Highly Phosphorescent Bis-Cyclometalated Iridium Complexes: Synthesis, Photophysical Characterization, and Use in Organic Light Emitting Diodes", J. Am. Chem. Soc. 2001, 123, 4304-4312.

Sergey Lamansky et al., "Synthesis and Characterization of Phosphorescent Cyclometalated Iridium Complexes", Inorg. Chem. 2001, 40, 1704-1711.

* cited by examiner

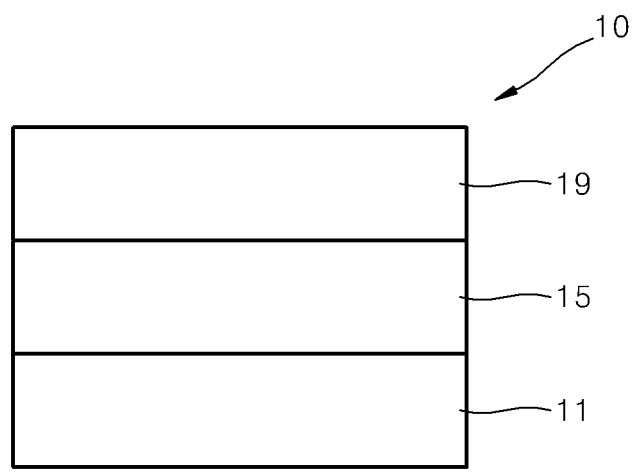

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0143604, filed on Oct. 22, 2014, in the Korean Intellectual Property Office, and all the benefits accruing therefrom under 35 U.S.C. §119, the content of which is incorporated herein in its entirety by reference.

BACKGROUND

1. Field

The present disclosure relates to an organometallic compound and an organic light-emitting device including the organometallic compound

2. Description of the Related Art

Organic light-emitting devices (OLEDs) are self-emission devices that have wide viewing angles, high contrast ratios, and short response times. In addition, OLEDs exhibit excellent brightness, driving voltages, and response speed characteristics, and produce full-color images.

A typical organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers such as the holes and the electrons recombine in the emission layer to generate excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are an organometallic compound and an organic light-emitting device including the organometallic compound.

Additional aspects will be set forth in part in the description which follows and, in part, will be apparent from the description, or may be learned by practice of the presented exemplary embodiments.

According to an aspect of an exemplary embodiment, an organometallic compound is represented by Formula 1:

$$M(L_1)_{n1}(L_2)_{n2}(L_3)_{n3} \quad \text{Formula 1}$$

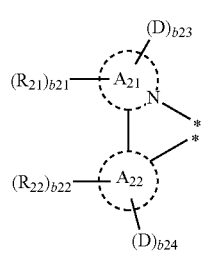

Formula 2

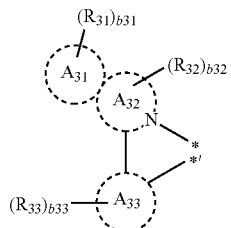

Formula 3 wherein, in Formulae 1, 2 and 3,

M may be selected from a Period 1 transition metal, a Period 2 transition metal, and a Period 3 transition metal;

$L_1$ may be a first ligand represented by Formula 2;

$L_2$ may be a second ligand represented by Formula 3;

$L_3$ may be selected from a monovalent organic ligand, a divalent organic ligand and a trivalent organic ligand;

n1 and n2 may be each independently an integer selected from 1, 2, and 3, wherein when n1 is 2 or more, groups $L_1$ may be identical or different, and when n2 is 2 or more, groups $L_2$ may be identical or different;

when n3 is an integer selected from 0, 1, 2, 3, and 4, and n3 is 2 or more, groups $L_3$ may be identical or different;

$A_{21}$ and $A_{32}$ may be each independently $C_1$-$C_{10}$ heterocycloalkane, $C_1$-$C_{10}$ heterocycloalkene, $C_1$-$C_{10}$ heteroarene, and non-aromatic condensed heteropolycycle;

$A_{22}$ and $A_{33}$ may be each independently selected from $C_3$-$C_{10}$ cycloalkane, $C_1$-$C_{10}$ heterocycloalkane, $C_3$-$C_{10}$ cycloalkene, $C_1$-$C_{10}$ heterocycloalkene, $C_6$-$C_{10}$ arene, $C_1$-$C_{10}$ heteroarene, non-aromatic condensed polycycle and non-aromatic condensed heteropolycycle;

$A_{31}$ may be selected from $C_3$-$C_{20}$ cycloalkene and $C_1$-$C_{10}$ heterocycloalkene;

$R_{21}$, $R_{22}$, and $R_{31}$ to $R_{33}$ may be each independently selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), —B(Q$_6$)(Q$_7$), and —Ge(Q$_8$)(Q$_9$)(Q$_{10}$);

b21, b22, and b31 to b33 are each independently an integer selected from 1, 2, 3, and 4;

b23 and b24 are each independently selected from 0, 1, 2, 3, and 4, wherein the sum of b23 and b24 is equal to or greater than 1;

* and *' may be each independently a binding site with M in Formula 1;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group and substituted monovalent non-aromatic condensed heteropolycyclic group, may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_{10}$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

According to an aspect of another exemplary embodiment, an organic light-emitting device includes:

a first electrode;

a second electrode; and an organic layer disposed between the first electrode and the second electrode, wherein the organic layer includes an emission layer and one or more organometallic compounds.

BRIEF DESCRIPTION OF THE DRAWINGS

These and/or other aspects will become apparent and more readily appreciated from the following description of the exemplary embodiments, taken in conjunction with the accompanying drawings in which:

the FIGURE illustrates a schematic view of an organic light-emitting device according to an embodiment of the inventive concept.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise. An expression used in the singular encompasses the expression of the plural, unless it has a clearly different meaning in the context.

It will be further understood that the terms "comprises" and/or "comprising," or "includes" and/or "including" used herein specify the presence of stated features, regions, integers, steps, operations, elements, and/or components, but do not preclude the presence or addition of one or more other features, regions, integers, steps, operations, elements, and/or components.

It will be understood that when a component, such as a layer, a film, a region, or a plate, is referred to as being "on" another component, the component can be directly on the other component or intervening components may be present thereon. In contrast, when an element is referred to as being "directly on" another element, there are no intervening elements present.

Since sizes and thicknesses of components in the drawings are arbitrarily illustrated for convenience of explanation, the following embodiments are not limited thereto.

Spatially relative terms, such as "beneath," "below," "lower," "above," "upper" and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As used herein, the term the "organic layer" refers to a single and/or a plurality of layers disposed between the first electrode and the second electrode in an organic light-emitting device. A material included in the "organic layer" is not limited to an organic material.

An organometallic compound represented by Formula 1 below:

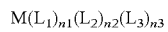

$$M(L_1)_{n1}(L_2)_{n2}(L_3)_{n3} \qquad \text{Formula 1}$$

wherein in Formula 1, M may be selected from a Period 1 transition metal, a Period 2 transition metal, and a Period 3 transition metal.

For example, in Formula 1, M may be iridium (Ir), platinum (Pt), osmium (Os), titanium (Ti), zirconium (Zr), hafnium (Hf), europium (Eu), terbium (Tb) or thulium (Tm), but is not limited thereto.

In some embodiments, in Formula 1, M may be Os, Ir or Pt, but is not limited thereto.

In some embodiments, in Formula 1, M may be Ir, but is not limited thereto.

In Formula 1, $L_1$ may be a first ligand represented by Formula 2 below;

$L_2$ may be a second ligand represented by Formula 3 below; and $L_3$ may be selected from a monovalent organic ligand, divalent organic ligand and trivalent organic ligand.

Formula 2

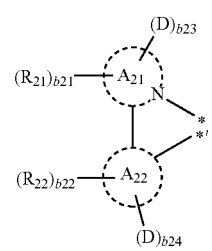

Formula 3

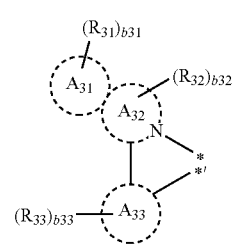

Detailed description of the first ligand, the second ligand, the monovalent organic ligand, the divalent organic ligand, and the trivalent organic ligand will be provided later.

In Formula 1, n1 denotes the number of groups $L_1$ and may be an integer selected from 1, 2, and 3. For example, in Formula 1, n1 may be 1 or 2, but is not limited thereto. When n1 is 2 or more, groups $L_1$ may be identical or different.

In Formula 1, n2 denotes the number of groups $L_2$ and may be an integer selected from an integer 1, 2, and 3. For example, in Formula 1, n2 may be 1 or 2, but is not limited thereto. When n2 is 2 or more, groups $L_2$ may be identical or different.

In Formula 1, n3 denotes the number of groups $L_3$ and may be selected from 0, 1, 2, 3, and 4. For example, in Formula 1, n3 may be 0 but is not limited thereto. When n2 is 2 or more, groups $L_3$ may be identical or different.

In some embodiments, in Formula 1, n1 may be 2, n2 may be 1, n3 may be 0, but they are not limited thereto.

In some embodiments, in Formula 1, n1 may be 1, n2 may be 2, n3 may be 0, but they are not limited thereto.

In Formulae 2 and 3, $A_{21}$ and $A_{32}$ may be each independently selected from $C_1$-$C_{10}$ heterocycloalkane, $C_1$-$C_{10}$ heterocycloalkene, $C_1$-$C_{10}$ heteroarene, and non-aromatic condensed heteropolycycle. $A_{21}$ and $A_{32}$ may each independently include a nitrogen atom (N) as a ring-forming atom.

In some embodiments, in Formulae 2 and 3, $A_{21}$ and $A_{32}$ may each independently be a pyrrole, an imidazole, a pyrazole, a thiazole, an isothiazole, an oxazole, an isoxazole (isooxazole), a triazole, a pyridine, a pyrazine, a pyrimidine, a quinoline, an isoquinoline, a benzoquinoline, a quinoxaline, a quinazoline, a naphthyridine, a benzoimidazole, a benzoxazole, an isobenzoxazole, an oxadiazole, or a triazine, but are not limited thereto.

In some embodiments, in Formulae 2 and 3, $A_{21}$ and $A_{32}$ may each independently be a pyridine, a pyrazine, a pyrimidine, a quinoline, an isoquinoline, a benzoquinoline, a quinoxaline, a quinazoline, a naphthyridine, or a triazine, but are not limited thereto.

In some embodiments, in Formulae 2 and 3, $A_{21}$ and $A_{32}$ may each independently be a pyridine, a pyrazine, a pyrimidine, a quinoline, an isoquinoline, a quinoxaline, a quinazoline, or a naphthyridine, but are not limited thereto.

In some embodiments, in Formulae 2 and 3, $A_{21}$ and $A_{32}$ may each independently be a pyridine, a quinoline, or an isoquinoline, but are not limited thereto.

In Formulae 2 and 3, $A_{22}$ and $A_{33}$ may be each independently selected from a $C_3$-$C_{10}$ cycloalkane, a $C_1$-$C_{10}$ heterocycloalkane, a $C_3$-$C_{10}$ cycloalkene, a $C_1$-$C_{10}$ heterocycloalkene, a $C_6$-$C_{10}$ arene, a $C_1$-$C_{10}$ heteroarene, a non-aromatic condensed polycycle, and a non-aromatic condensed heteropolycycle.

In some embodiments, in Formulae 2 and 3, $A_{22}$ and $A_{33}$ may each independently be a benzene, a naphthalene, a fluorene, a spiro-fluorene, an indene, a furan, a thiophene, a carbazole, a benzofuran, a benzothiophene, a dibenzofuran, a dibenzothiophene, a pyrrole, an imidazole, a pyrazole, a thiazole, an isothiazole, an oxazole, an isoxazole, a triazole, a pyridine, a pyrazine, a pyrimidine, a quinoline, an isoquinoline, a benzoquinoline, a quinoxaline, a quinazoline, a naphthyridine, a benzoimidazole, a benzoxazole, an isobenzoxazole, an oxadiazole or a triazine, but are not limited thereto.

In some embodiments, in Formulae 2 and 3, $A_{22}$ and $A_{33}$ may each independently be a benzene, a naphthalene, a fluorene, a carbazole, a dibenzofuran, a dibenzothiophene, a pyridine, a pyrazine, a pyrimidine, a quinoline, an isoquinoline, a benzoquinoline, a quinoxaline, a quinazoline, a naphthyridine, or a triazine, but are not limited thereto.

In some embodiments, in Formulae 2 and 3, $A_{22}$ and $A_{33}$ may each independently be a benzene, a naphthalene, a fluorene, a carbazole, a dibenzofuran, or a dibenzothiophene, but are not limited thereto.

In some embodiments, in Formulae 2 and 3, $A_{22}$ and $A_{33}$ may each independently be a benzene or a naphthalene, but are not limited thereto.

In Formula 3, $A_{32}$ may be selected from a $C_3$-$C_{20}$ cycloalkene and a $C_1$-$C_{10}$ heterocycloalkene.

For example, in Formula 3, $A_{32}$ may be a cyclopentene, a cyclohexene, a cycloheptene, a bicycloheptene, a dihydrofuran, a dihydropyran, or an oxabicycloheptene, but is not limited thereto.

In some embodiments, in Formula 3, $A_{32}$ may be a cyclopentene, a cyclohexane, or a bicycloheptene, but is not limited thereto.

In some embodiments, in Formula 3, $A_{32}$ may be a cyclohexene or a bicycloheptene, but is not limited thereto.

In Formulae 2 and 3, $R_{21}$, $R_{22}$, and $R_{31}$ to $R_{33}$ may be each independently selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-N(Q_1)(Q_2)$, $-Si(Q_3)(Q_4)(Q_5)$, $-B(Q_6)(Q_7)$, and $-Ge(Q_8)(Q_9)(Q_{10})$;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group, may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $-N(Q_{11})(Q_{12})$, $-Si(Q_{13})(Q_{14})(Q_{15})$, and $-B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$;

wherein $Q_1$ to $Q_{10}$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In some embodiments, in Formulae 2 and 3, $R_{21}$, $R_{22}$, and $R_{31}$ to $R_{33}$ may be each independently selected from a hydrogen, a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —$Si(Q_{33})(Q_{34})(Q_{35})$; and —$Si(Q_3)(Q_4)(Q_5)$ and —$Ge(Q_8)(Q_9)(Q_{10})$;

wherein $Q_3$ to $Q_5$, $Q_8$ to $Q_{10}$, and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, but are not limited thereto.

In some embodiments, in Formulae 2 and 3, $R_{21}$, $R_{22}$, and $R_{31}$ to $R_{33}$ may be each independently selected from a hydrogen, a deuterium, —F, —Cl, —Br, —I, a cyano group, a nitro group, a methyl group, an ethyl group, a n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, and a pentoxy group;

a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, and a pentoxy group, each substituted with at least one selected from a deuterium, —F, a cyano group, and a nitro group;

a phenyl group, a naphthyl group, a pyridinyl group, a pyrimidinyl group, a triazinyl group, and a dibenzofuranyl group;

a phenyl group, a naphthyl group, a pyridinyl group, a pyrimidinyl group, a triazinyl group, and a dibenzofuranyl group, each substituted with at least one selected from —F, a cyano group, a nitro group, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{33}$)($Q_{34}$)($Q_{35}$); and —Si($Q_3$)($Q_4$)($Q_5$), and —Ge($Q_8$)($Q_9$)($Q_{10}$);

wherein $Q_3$ to $Q_5$, $Q_8$ to $Q_{10}$, and $Q_{33}$ to $Q_{35}$ may be each independently selected from a hydrogen, a $C_1$-$C_{10}$ alkyl group, a phenyl group, a naphthyl group, a pyridinyl group, a pyrimidinyl group, and a triazinyl group, but are not limited thereto.

In Formula 2, b21 denotes the number of groups $R_{21}$ and may be an integer selected from 1, 2, 3, and 4. When b21 is 2 or more, groups $R_{21}$ may be identical or different.

In Formula 2, b22 denotes the number of groups $R_{22}$ and may be an integer selected from 1, 2, 3, and 4. When b22 is 2 or more, groups $R_{22}$ may be identical or different.

In Formula 2, b23 and b24 denote the number of deuterium (D) atoms, and may each independently be an integer selected from 0, 1, 2, 3, and 4, wherein the sum of b23 and b24 may be 1 or more. In some embodiments, in Formula 2, b23 may be 4, and b24 may be 0, but they are not limited thereto. In some embodiments, in Formula 2, b23 may be 0, and b24 may be 4, but they are not limited thereto. In some embodiments, in Formula 2, b23 may be 4, and b24 may be 4, but they are not limited thereto. In some embodiments, in Formula 2, the sum of b23 and b24 may be 4 or more, but they are not limited thereto.

In Formula 3, b31 denotes the number of groups $R_{31}$ and may be an integer selected from 1, 2, 3, and 4. When b31 is 2 or more, groups $R_{31}$ may be identical or different.

In Formula 3, b32 denotes the number of groups $R_{32}$ and may be an integer selected from 1, 2, 3, and 4. When b32 is 2 or more, groups $R_{32}$ may be identical or different.

In Formula 3, b33 denotes the number of groups $R_{33}$ and may be an integer selected from 1, 2, 3, and 4. When b33 is 2 or more, groups $R_{33}$ may be identical or different.

In Formulae 2 and 3, * and *' may each independently be a binding site with M in Formula 1.

For example, in Formula 1, $L_1$ may be a first ligand represented by any one of Formulae 2-1 to 2-4 below, but is not limited thereto:

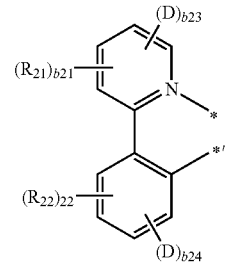

2-1

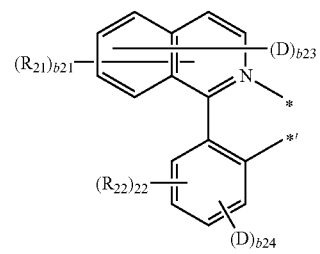

2-2

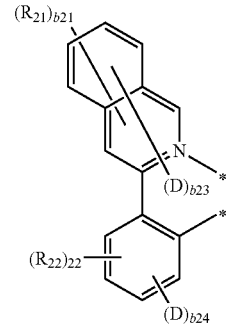

2-3

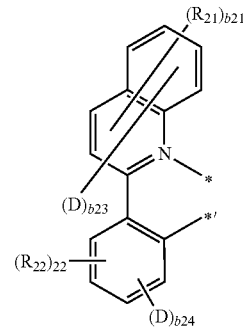

2-4 wherein in Formulae 2-1 to 2-4, D is deuterium, and descriptions of $R_{21}$, $R_{22}$, b21, b22, b23, b24, *, and *' are the same as the descriptions in Formula 2.

In some embodiments, in Formula 1, $L_1$ may be a first ligand represented by any one of Formulae 2-11 to 2-18 below, but is not limited thereto:

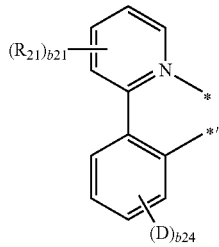
2-11

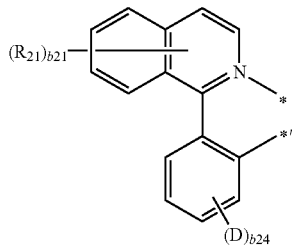
2-12

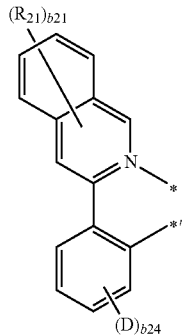
2-13

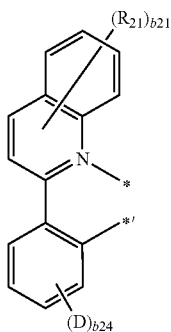
2-14

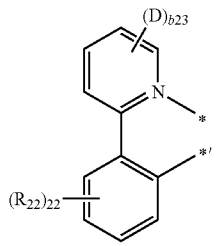
2-15

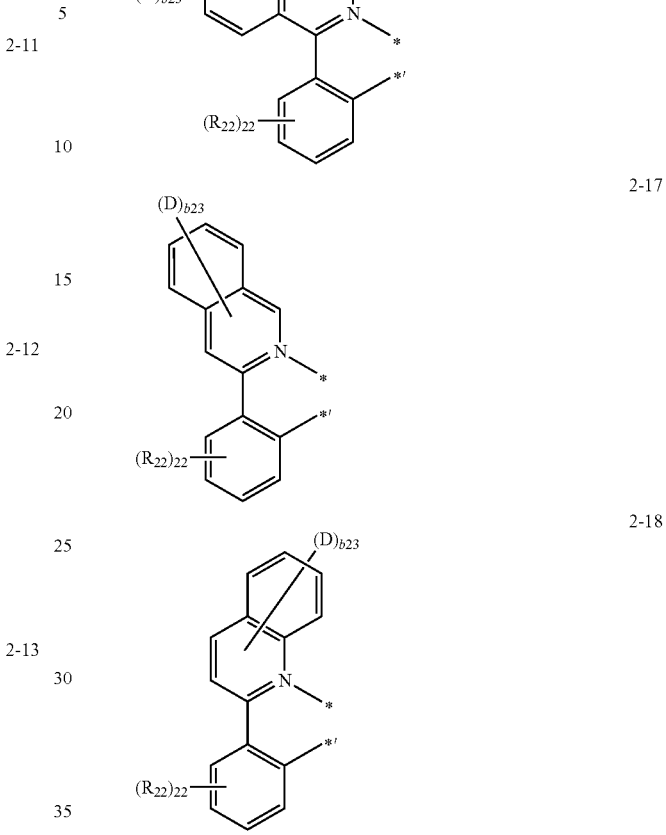
2-16

2-17

2-18 wherein, in Formulae 2-11 to 2-18, D is deuterium and descriptions of $R_{21}$, $R_{22}$, b21, b22, b23, b24, *, and *' are the same as the descriptions in Formula 2.

In some embodiments, in Formula 1, $L_1$ may be a first ligand represented by any one of Formulae 2-21 to 2-24 below, but is not limited thereto:

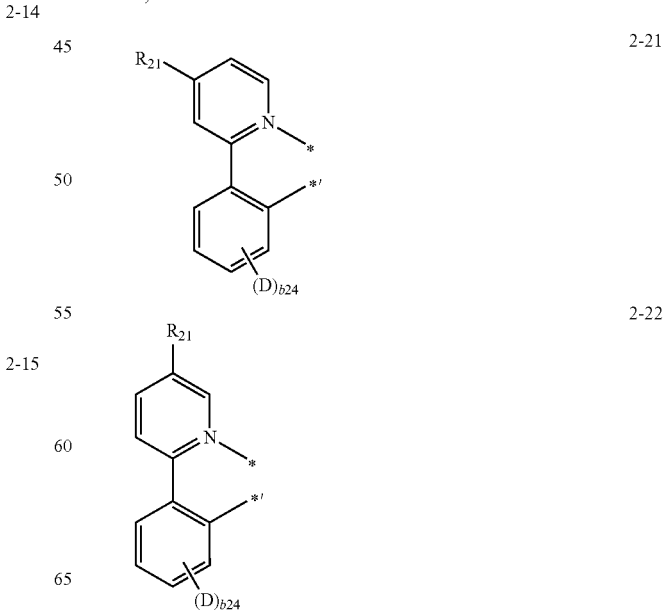
2-21

2-22

2-23

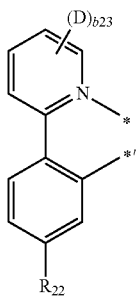

2-24

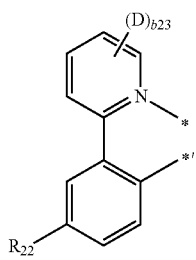

wherein, in Formulae 2-21 to 2-24, D is deuterium and descriptions of $R_{21}$, $R_{22}$, b21, b22, b23, b24, *, and *' are the same as the descriptions in Formula 2.

In some embodiments, in Formula 1, $L_1$ may be a first ligand represented by any one of Formulae 2-31 to 2-34 below, but is not limited thereto:

2-31

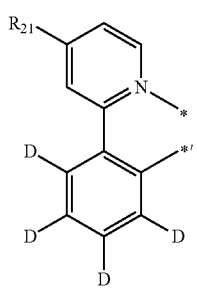

2-32

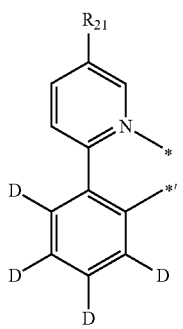

2-33

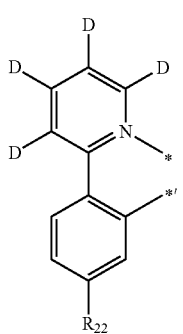

2-34

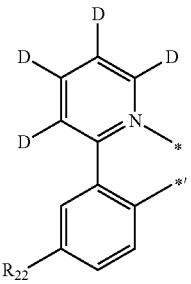

wherein, in Formulae 2-31 to 2-34, D is deuterium and descriptions of $R_{21}$, $R_{22}$, *, and *' are the same as the descriptions in Formula 2.

For example, in Formula 1, $L_2$ may be a second ligand represented by any one of Formulae 3-1 to 3-15 below, but is not limited thereto:

3-1

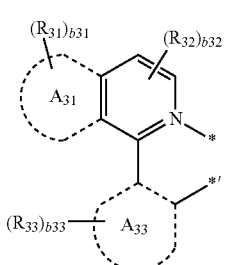

3-2

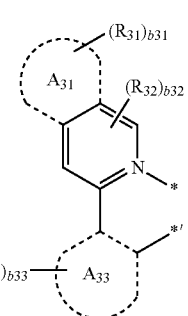

3-3

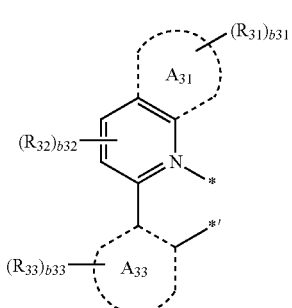

3-4

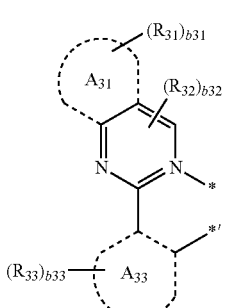

-continued
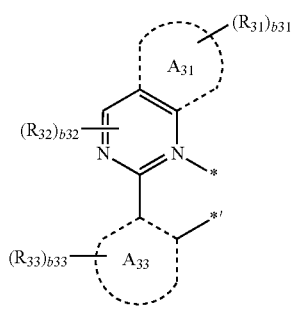
3-5
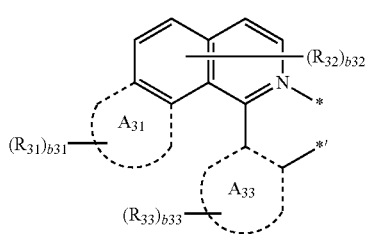
3-6
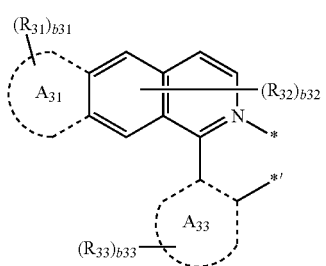
3-7
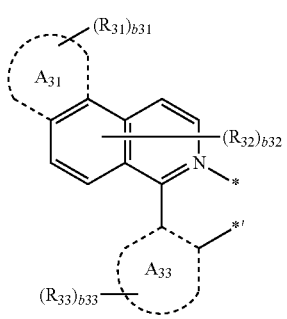
3-8
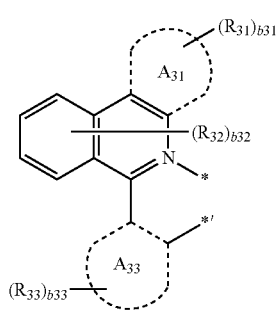
3-9
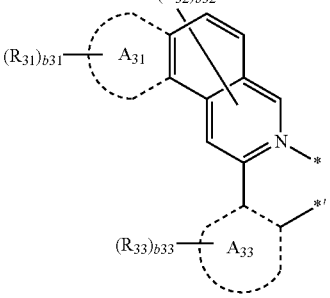
3-10
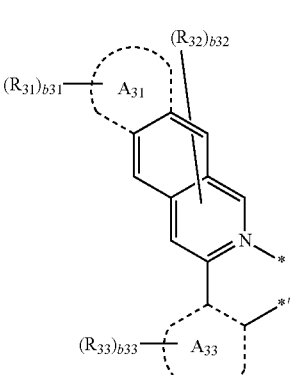
3-11
3-12
3-13

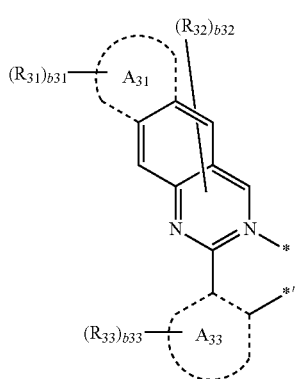
3-14
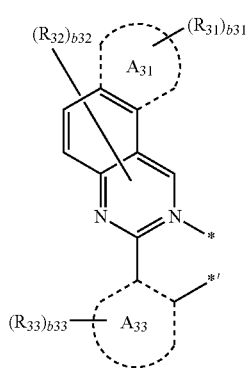
3-15
wherein, in Formulae 3-1 to 3-15,
descriptions of $A_{31}$, $A_{33}$, $R_{31}$ to $R_{33}$, b31 to b33, * and *' are the same as the descriptions in Formula 3.
In some embodiments, in Formula 1, $L_2$ may be a second ligand represented by any one of Formulae 3-31 to 3-45 below, but is not limited thereto:
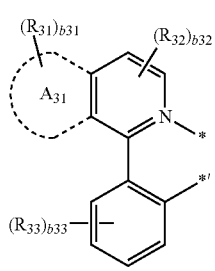
3-31
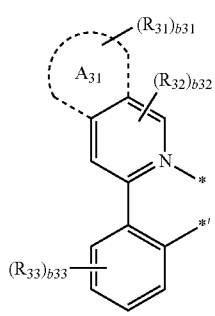
3-32
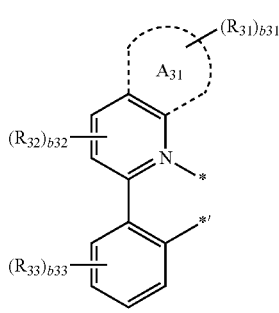
3-33
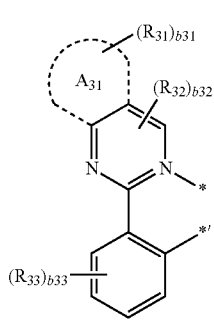
3-34
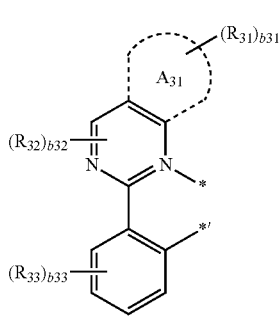
3-35
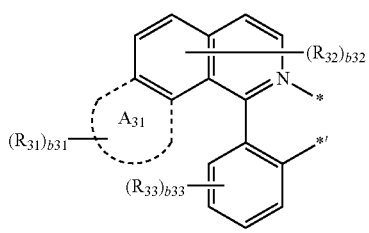
3-36
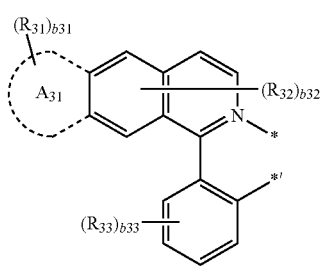
3-37

3-38
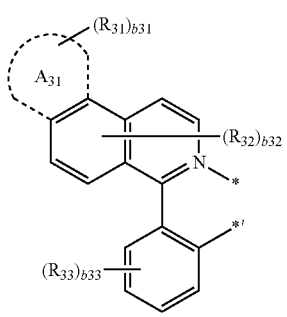
3-39
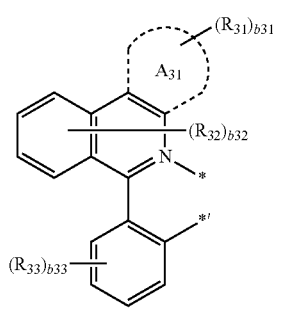
3-40
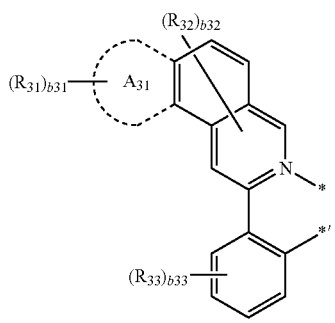
3-41
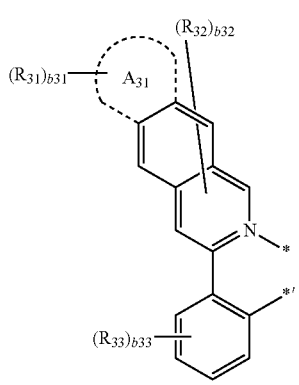
3-42
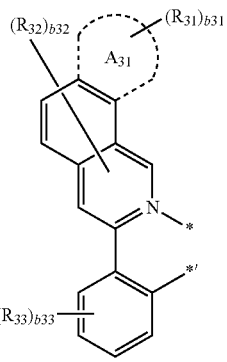
3-43
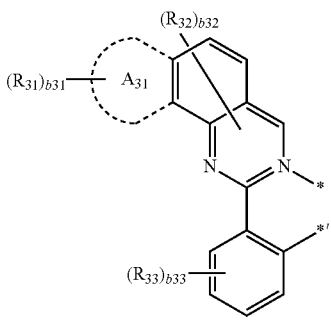
3-44
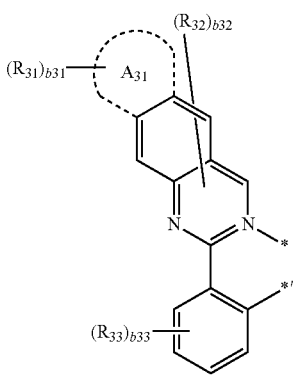
3-45
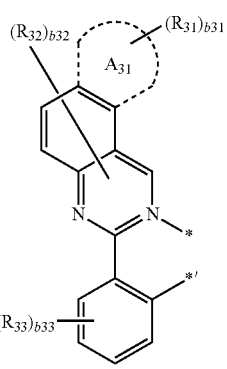
wherein, in Formulae 3-31 to 3-45,
descriptions of $A_{31}$, $R_{31}$ to $R_{33}$, b31 to b33, *, and *' are the same as the descriptions in Formula 3.
In some embodiments, in Formula 1, $L_2$ may be a second ligand represented by any one of Formulae 3-51 to 3-65 below, but is not limited thereto:

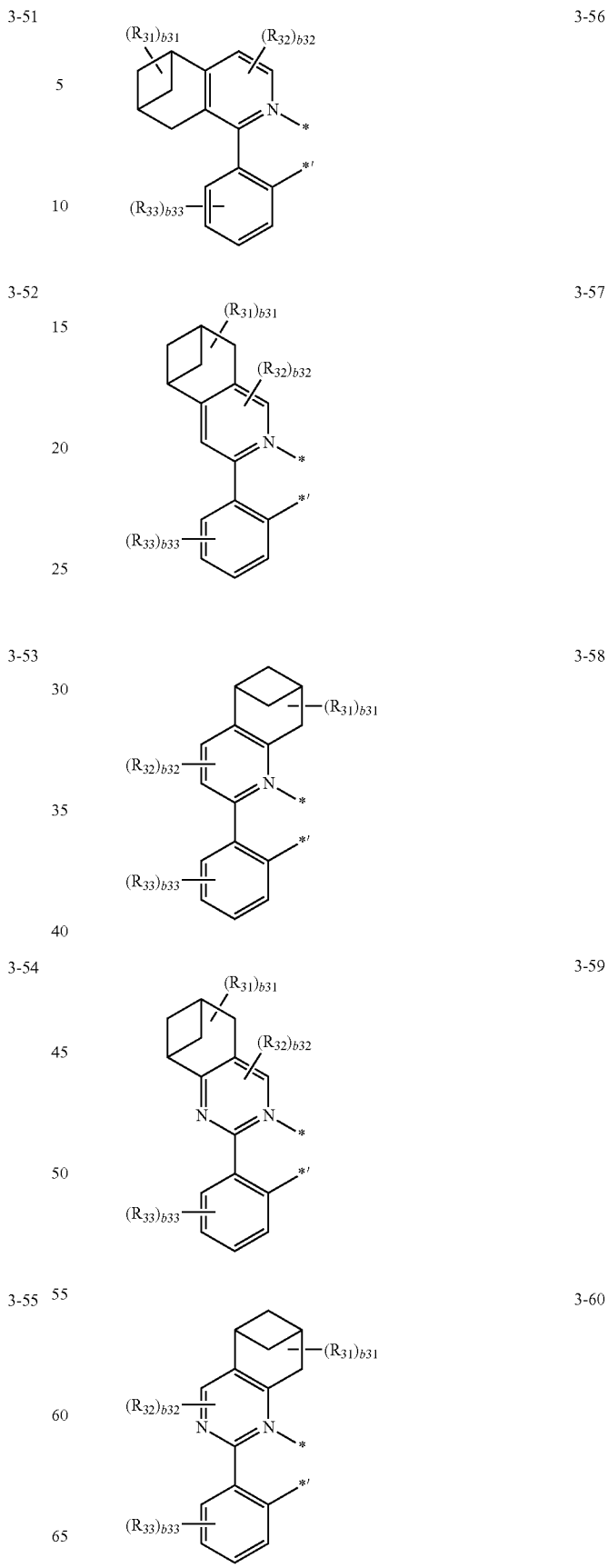

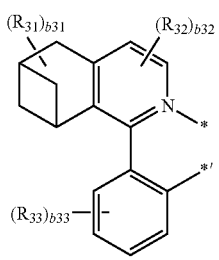

3-61

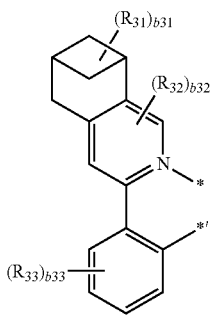

3-62

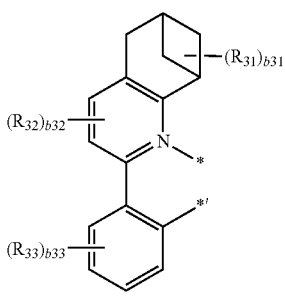

3-63

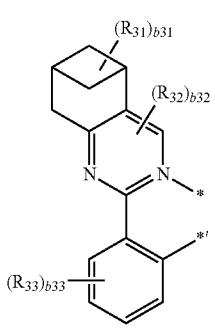

3-64

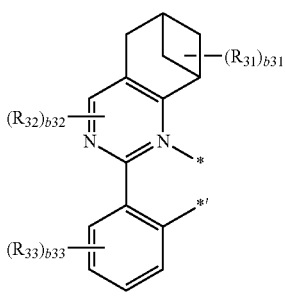

3-65 wherein, in Formulae 3-51 to 3-65, descriptions of $R_{31}$ to $R_{33}$, b31 to b33, *, and *' are the same as the descriptions in Formula 3.

For example, in Formula 1, $L_3$ may be selected from divalent organic ligands, but is not limited thereto.

In some embodiments, in Formula 1, $L_3$ may be represented by any one of Formulae 4-1 to 4-4 below, but is not limited thereto:

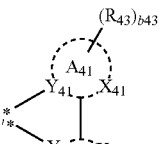

4-1

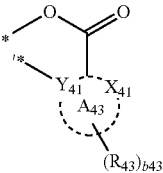

4-2

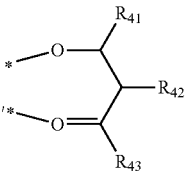

4-3

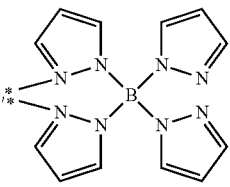

4-4 wherein, in Formulae 4-1 to 4-4, $X_{41}$ may be $CR_{41}$ or N; $X_{42}$ may be $CR_{42}$ or N;

$Y_{41}$ and $Y_{42}$ may each independently be carbon (C) atom or nitrogen (N) atom;

$A_{41}$ to $A_{43}$ may be each independently selected from a $C_3$-$C_{10}$ cycloalkane, a $C_1$-$C_{10}$ heterocycloalkane, a $C_3$-$C_{10}$ cycloalkene, a $C_1$-$C_{10}$ heterocycloalkene, a $C_6$-$C_{10}$ arene, a $C_1$-$C_{10}$ heteroarene, a non-aromatic condensed polycycle, and a non-aromatic condensed heteropolycycle;

$R_{41}$ to $R_{44}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_{41}$)($Q_{42}$)($Q_{43}$);

b43 and b44 may each independently be an integer selected from 1, 2, 3, 4, and 5;

$Q_{41}$ to $Q_{43}$ may each independently be a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group or a monovalent non-aromatic condensed heteropolycyclic group;

* and *' may each independently be a binding site with M in Formula 1.

In some embodiments, in Formula 1, $L_3$ may be represented by any one of Formulae 4-1 to 4-4 above;

wherein, in Formulae 4-1 to 4-4, $A_{41}$ to $A_{43}$ may each independently be a benzene, a naphthalene, a fluorene, a spiro-fluorene, an indene, a furan, a thiophene, a carbazole, a benzofuran, a benzothiophene, a dibenzofuran, a dibenzothiophene, a pyrrole, an imidazole, a pyrazole, a thiazole, an isothiazole, an oxazole, an isoxazole, a triazole, a pyridine, a pyrazine, a pyrimidine, a quinoline, an isoquinoline, a benzoquinoline, a quinoxaline, a quinazoline, a naphthyridine, a benzoimidazole, a benzoxazole, an isobenzoxazole, an oxadiazole or a triazine;

$R_{41}$ to $R_{44}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group or an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and —Si($Q_{41}$)($Q_{42}$)($Q_{43}$);

b43 and b4 may each independently be an integer selected from 1, 2, and 3;

$Q_{41}$ to $Q_{43}$ may be each independently selected from a $C_1$-$C_{10}$ alkyl group, a phenyl group, a naphthyl group, a pyridinyl group, a pyrimidinyl group, and a triazinyl group, but are not limited thereto.

In some embodiments, in Formula 1, $L_3$ may be represented by any one of Formulae 4-1 to 4-4 above; in Formulae 4-1 to 4-4, $A_{41}$ may be a pyridine, an imidazole, a pyrazole, a triazole, or a tetrazole, $A_{42}$ may be a benzene, a pyridine, a pyrazine, a pyrimidine, or a triazine, $A_{43}$ may be a benzene or a pyridine;

$R_{41}$ to $R_{44}$ may be each independently selected from a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group, each substituted with at least one selected from —F, a cyano group, and a nitro group;

c1 to c3 may each independently be an integer selected from 1, 2, and 3, but are not limited thereto.

In some embodiments, in Formula 1, $L_3$ may be represented by Formulae 5-1 to 5-119 below, but are not limited thereto:

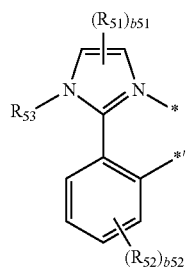

5-1

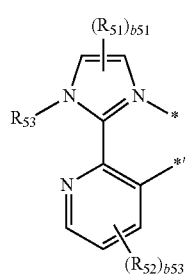

5-2

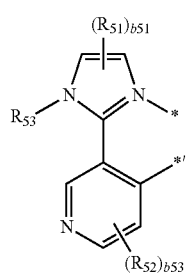

5-3

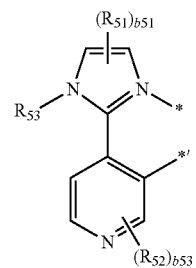

5-4

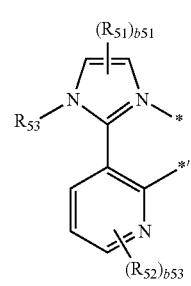

5-5

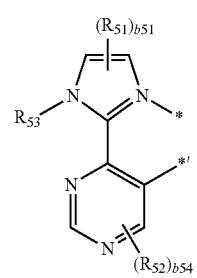

5-6

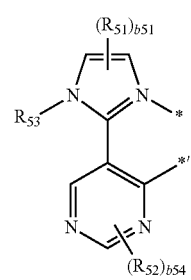

5-7

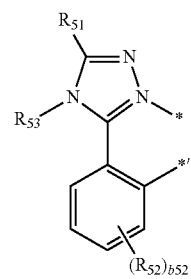

5-8

5-9
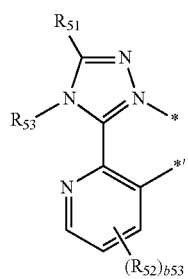
5-10
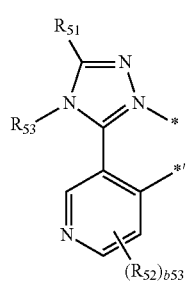
5-11
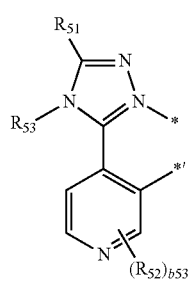
5-12
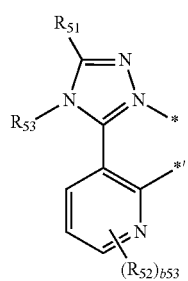
5-13
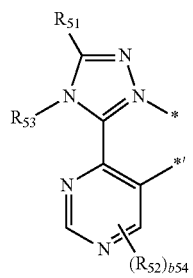
5-14
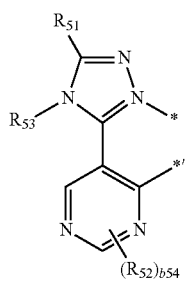
5-15
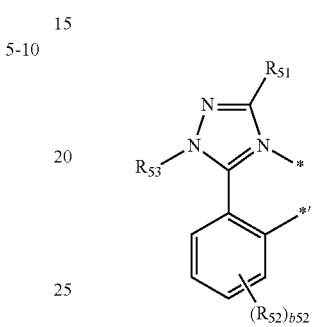
5-16
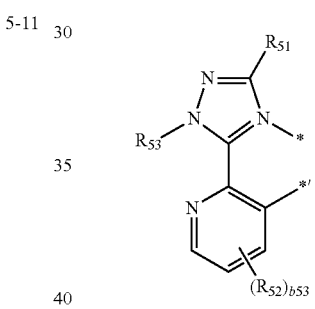
5-17
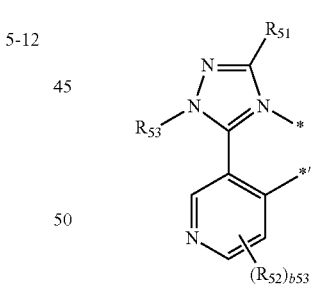
5-18
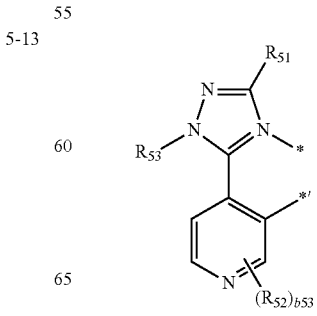

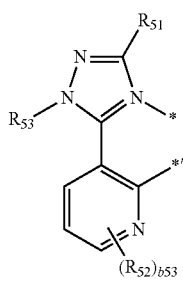
5-19
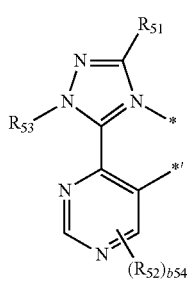
5-20
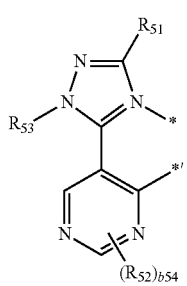
5-21
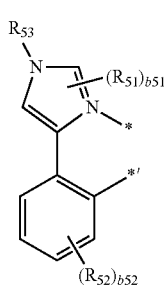
5-22
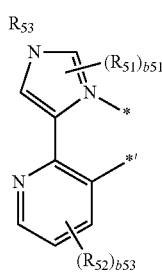
5-23
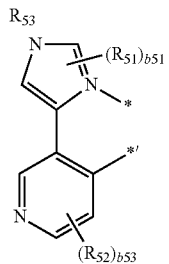
5-24
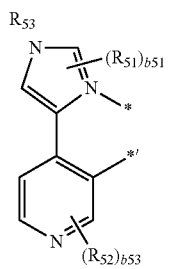
5-25
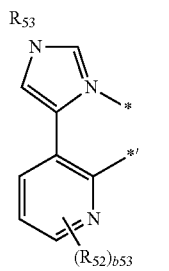
5-26
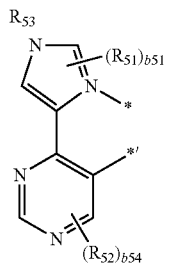
5-27
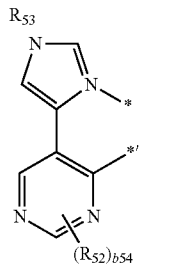
5-28
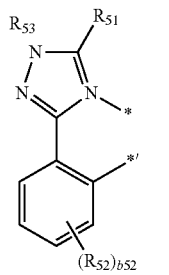
5-29

-continued
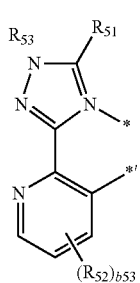
5-30
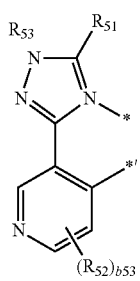
5-31
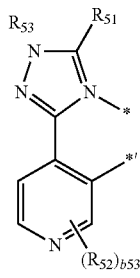
5-32
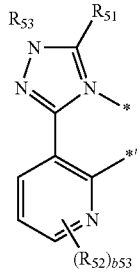
5-33
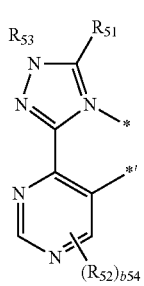
5-34
-continued
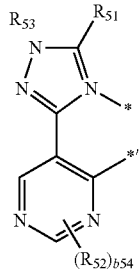
5-35
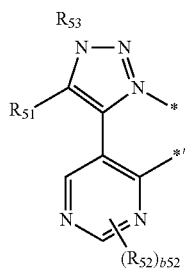
5-36
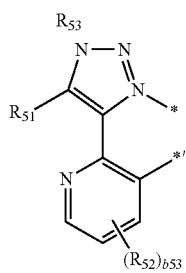
5-37
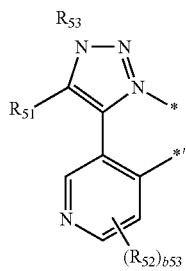
5-38
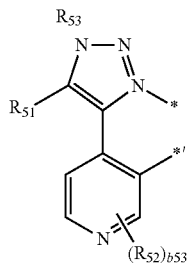
5-39
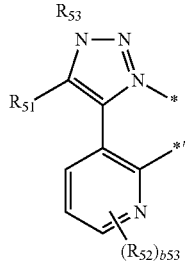
5-40

5-41 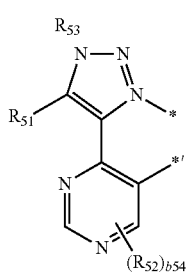
5-42 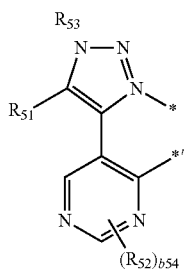
5-43 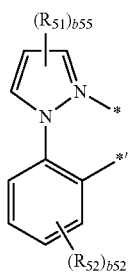
5-44 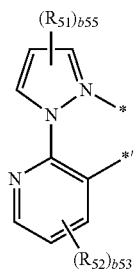
5-45 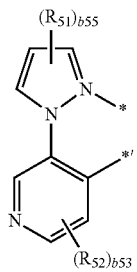
5-46 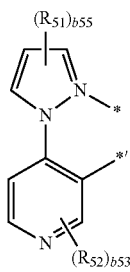
5-47 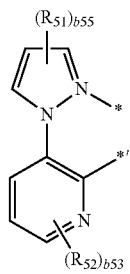
5-48 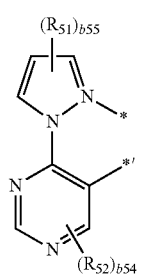
5-49 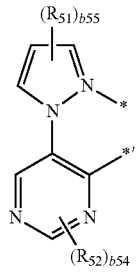
5-50 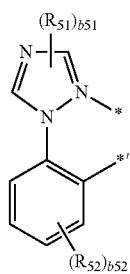
5-51 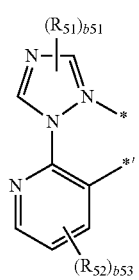

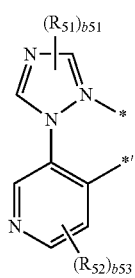 5-52
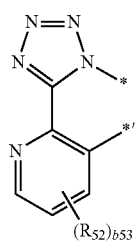 5-58
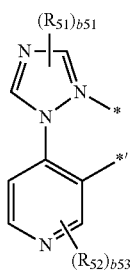 5-53
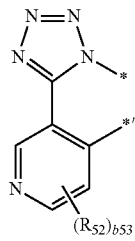 5-59
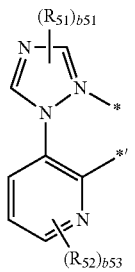 5-54
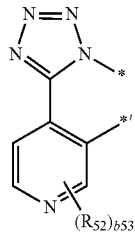 5-60
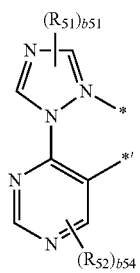 5-55
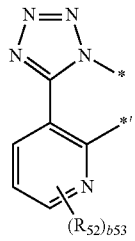 5-61
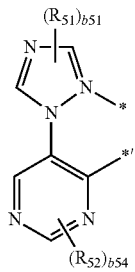 5-56
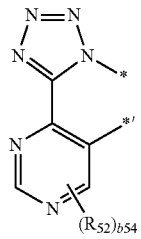 5-62
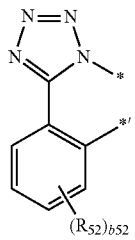 5-57
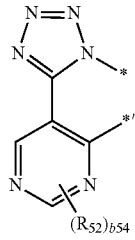 5-63

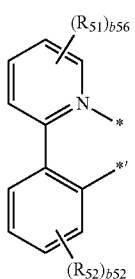
5-64
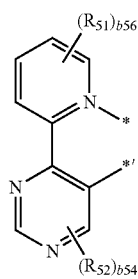
5-69
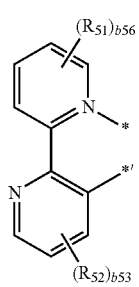
5-65
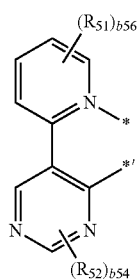
5-70
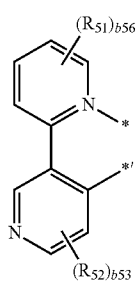
5-66
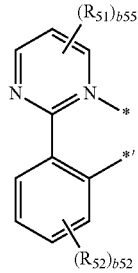
5-71
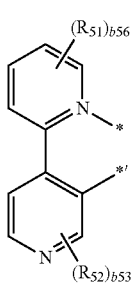
5-67
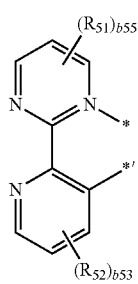
5-72
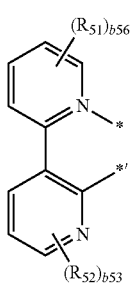
5-68
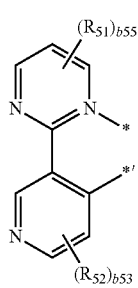
5-73

5-74 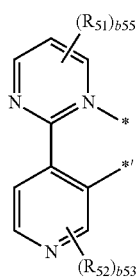
5-75 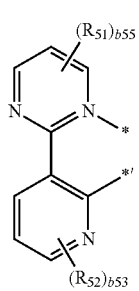
5-76 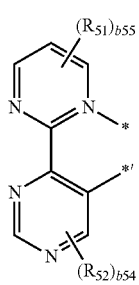
5-77 
5-78
5-79 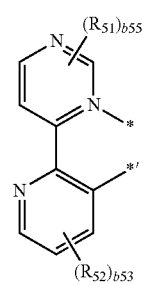
5-80 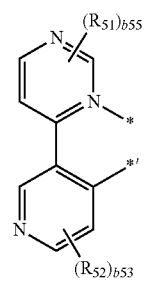
5-81 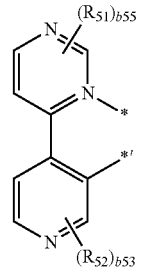
5-82 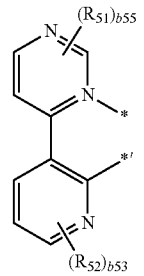
5-83 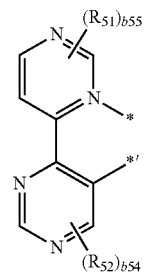

5-84 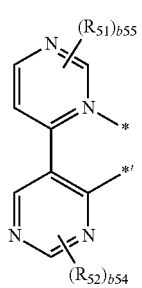
5-85 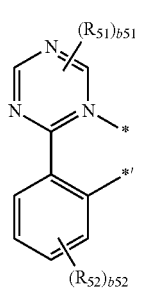
5-86 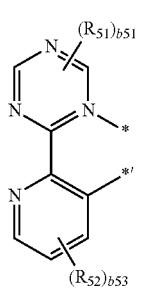
5-87 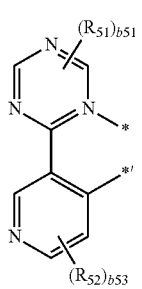
5-88 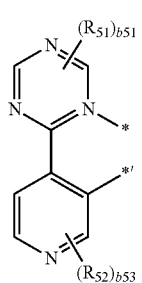
5-89 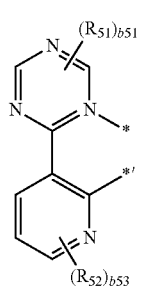
5-90 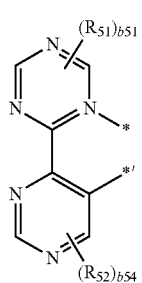
5-91 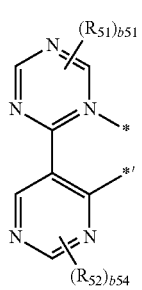
5-92 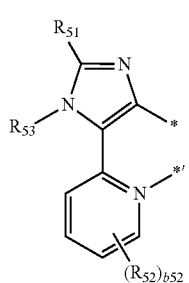
5-93 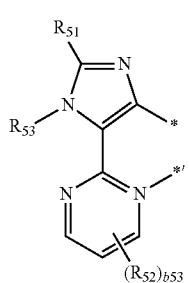

| | |
|---|---|
| 5-94 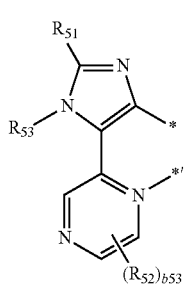 | 5-99 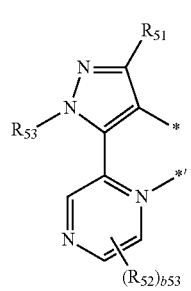 |
| 5-95 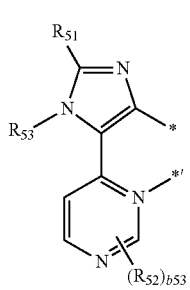 | 5-100 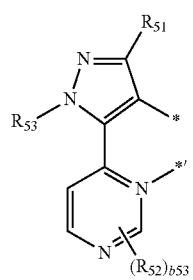 |
| 5-96 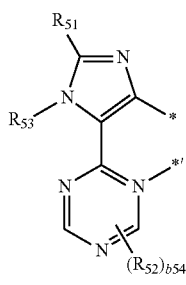 | 5-101 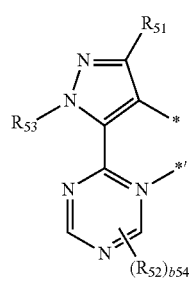 |
| 5-97 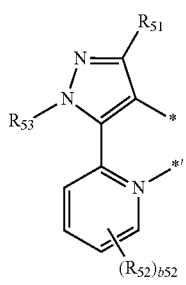 | 5-102 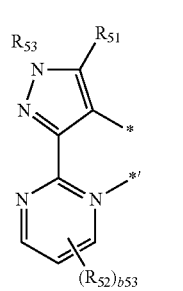 |
| 5-98 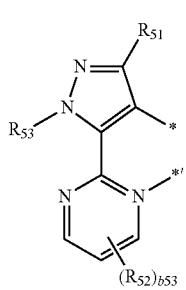 | 5-103 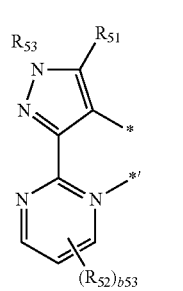 |

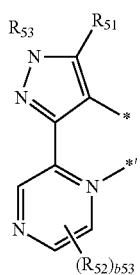 5-98
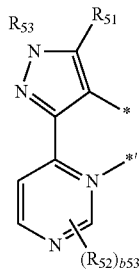 5-99
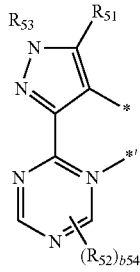 5-100
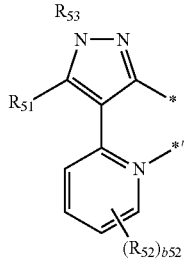 5-101
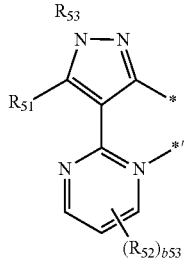 5-102
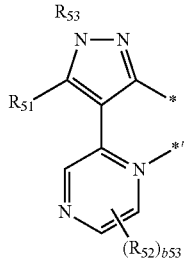 5-103
5-104 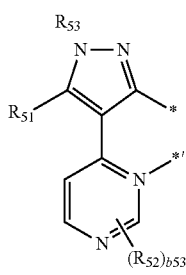
5-105 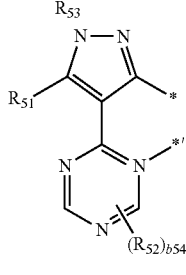
5-106 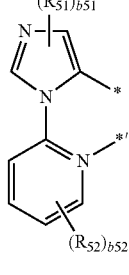
5-107 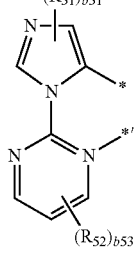
5-108 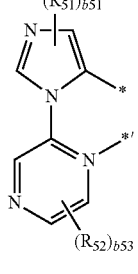
5-109 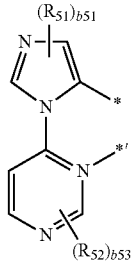
5-110
5-111
5-112
5-113
5-114
5-115

-continued 5-116
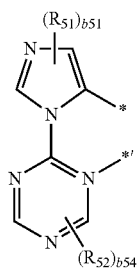

5-117
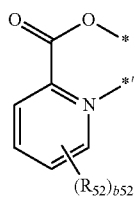

5-118
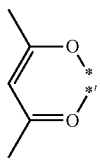

5-119
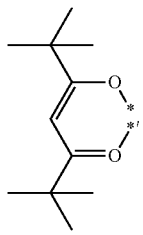

$R_{51}$ to $R_{53}$ may be each independently selected from a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group, each substituted with at least one selected from —F, a cyano group, and a nitro group;

b51 and b54 may each independently be 1 or 2;

b53 and b55 may each independently be an integer selected from 1, 2, and 3; b52 may be an integer selected from 1, 2, 3, and 4;

\* and \*' may each independently be a binding site with M in Formula 1.

In some embodiments, the organometallic compound may be represented by Formula 1-1 below, but is not limited thereto:

$$M(L_1)_{n1}(L_2)_{n2} \qquad \text{Formula 1-1}$$

wherein, in Formulae 1-1,

M may be Os, Ir or Pt;

$L_1$ may be represented by any one of Formulae 6-1 to 6-11 below;

6-1
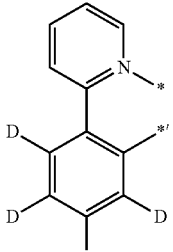

6-2
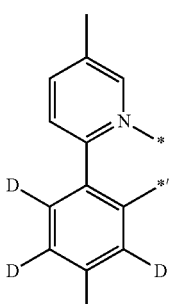

6-3
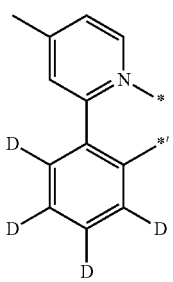

6-4
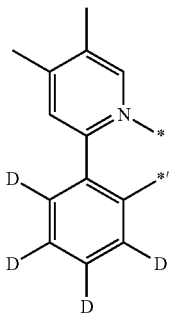

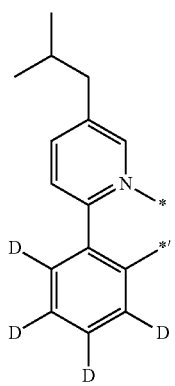
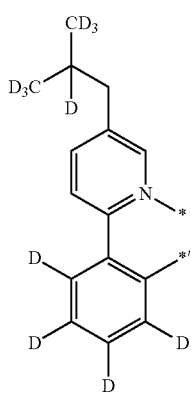
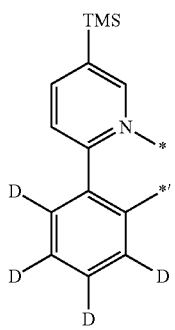
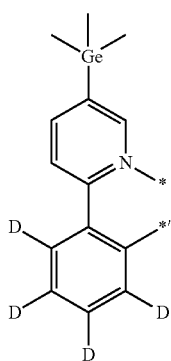
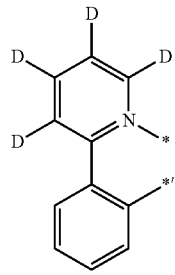
6-5
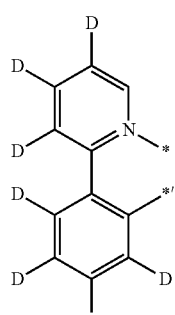
6-6
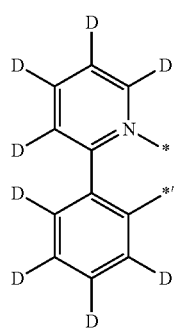
6-7
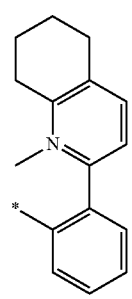
6-8
6-9
6-10
6-11
D is deuterium, n1 may be 2; $L_2$ may be represented by any one of Formulae 7-1 to 7-16 below:
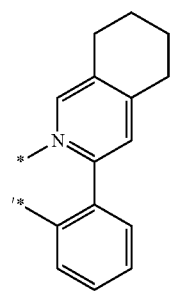
7-1
7-2

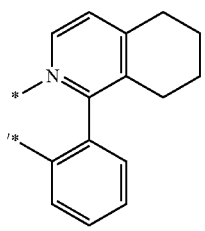
7-3
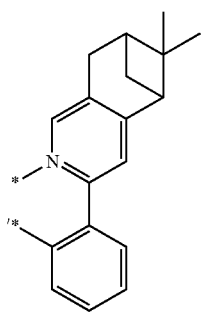
7-4
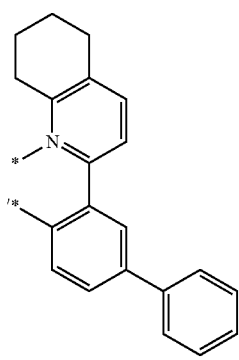
7-5
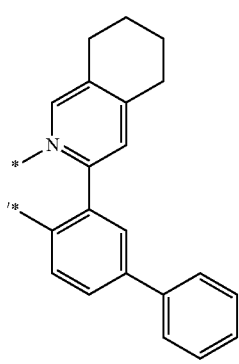
7-6
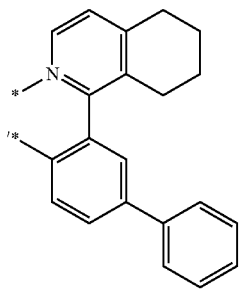
7-7
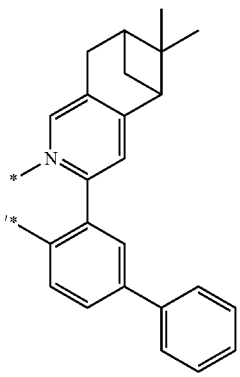
7-8
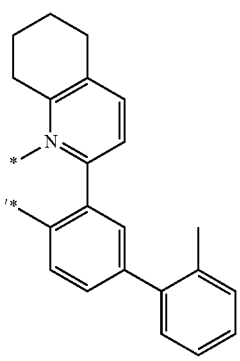
7-9
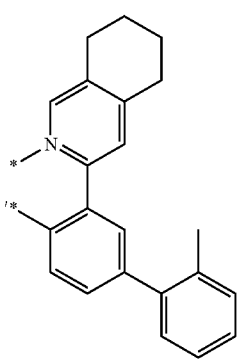
7-10
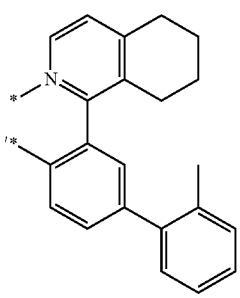
7-11

7-12
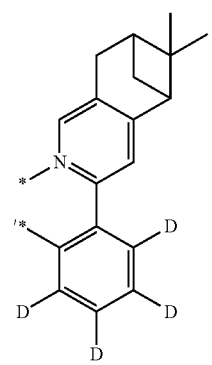
7-13
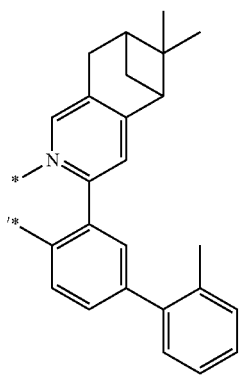
7-14
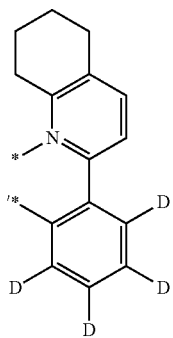
7-15
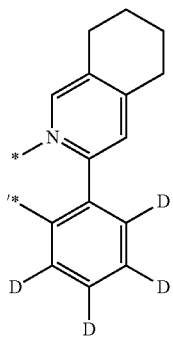
7-16
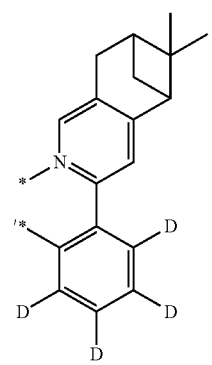
D is deuterium and n2 may be 1.
In some embodiments, the organometallic compound may be any one of compounds 1 to 19 below, but is not limited thereto:
1
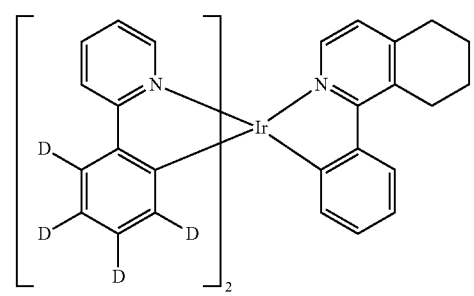
2
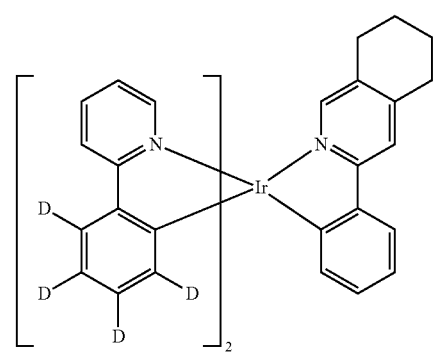
3
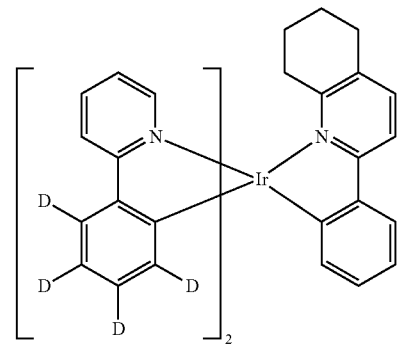

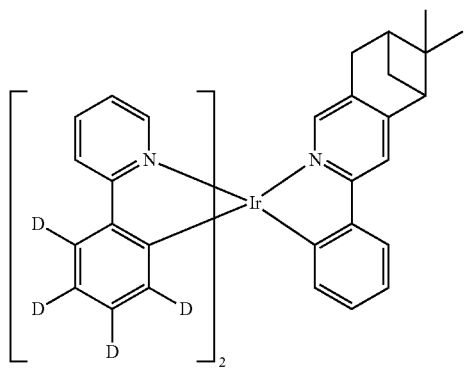
4
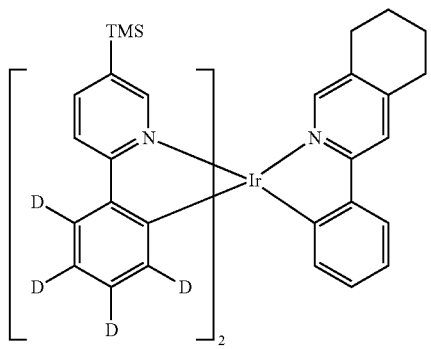
8
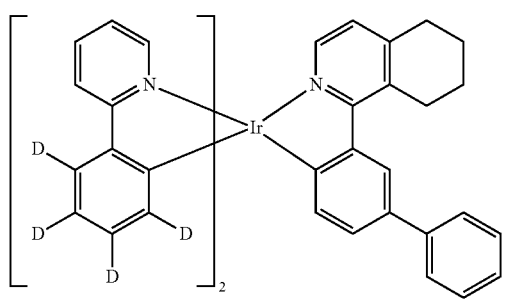
5
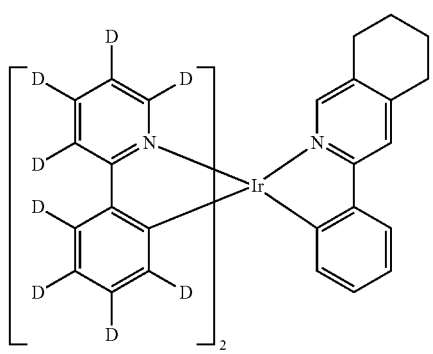
9
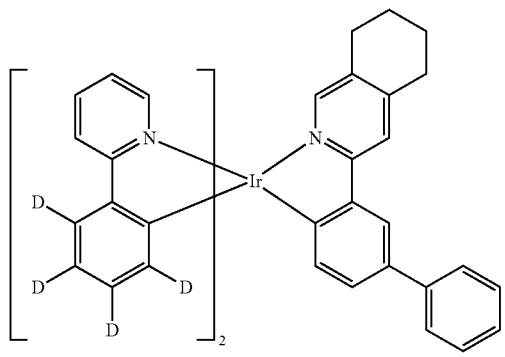
6
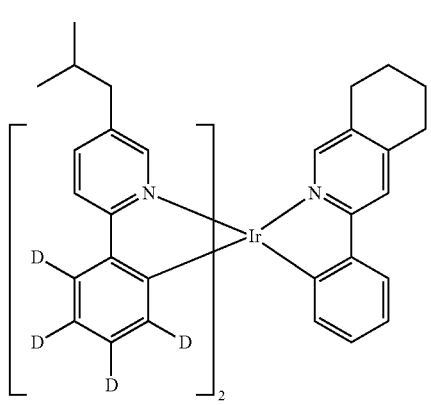
10
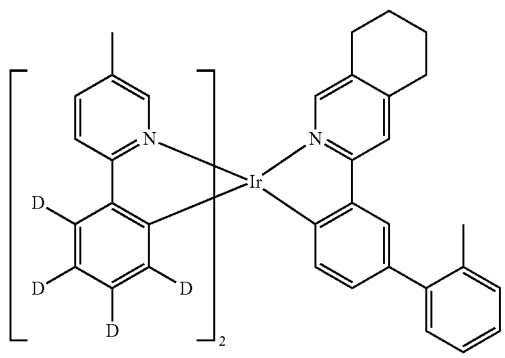
7
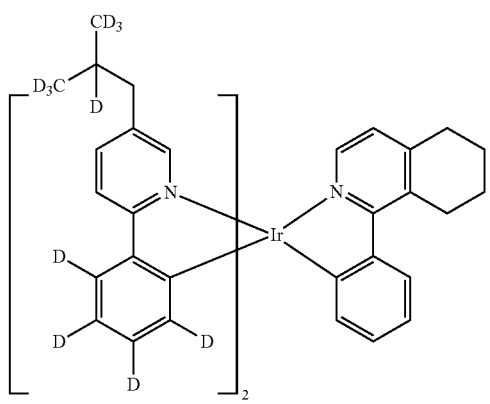
11

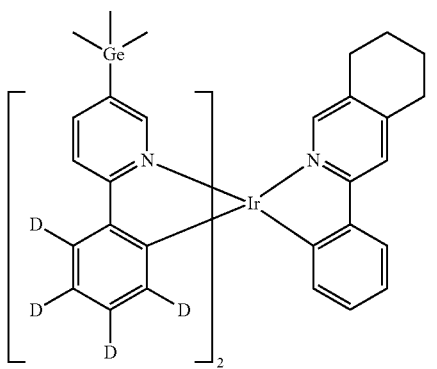
12
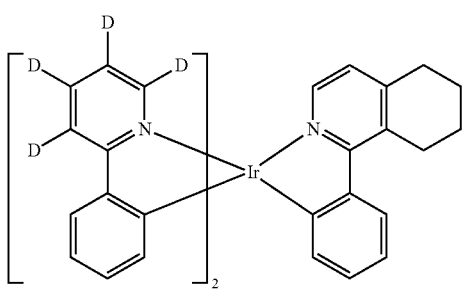
13
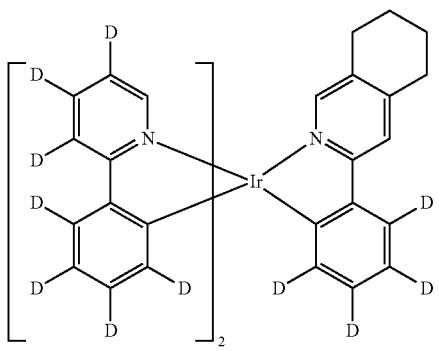
14
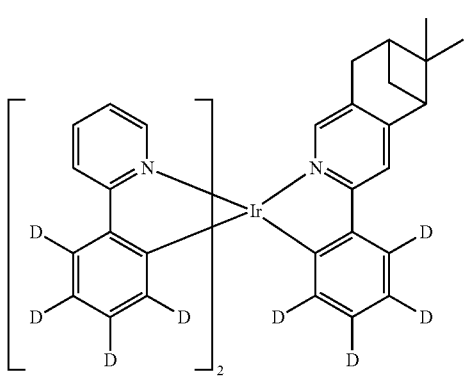
15
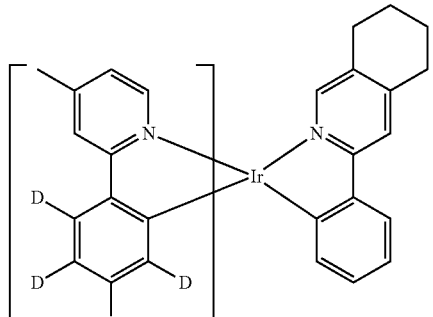
16
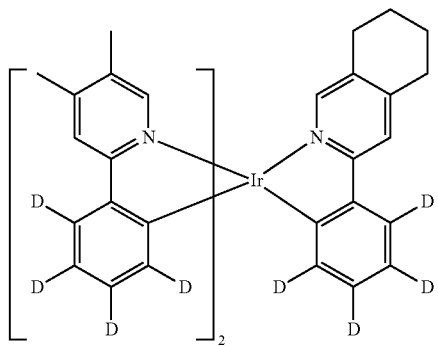
17
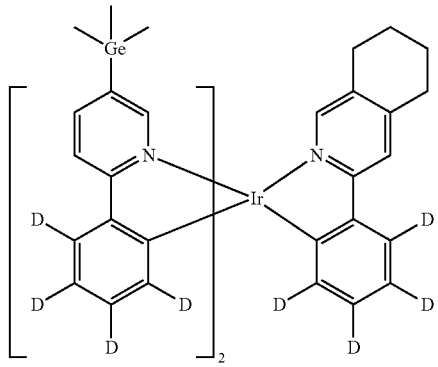
18
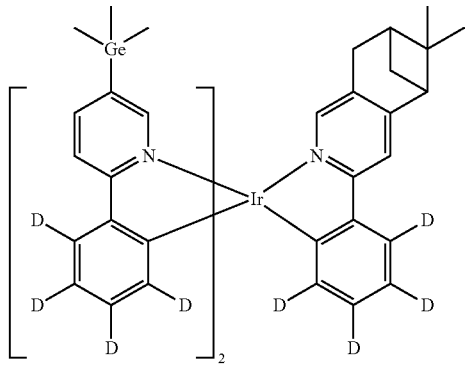
19
wherein, in compounds 1 to 19,
TMS may denote —Si(CH$_3$)$_3$.
The organometallic compound represented by Formula 1 may include, as described in Formula 1'-1 below, at least one deuterium.

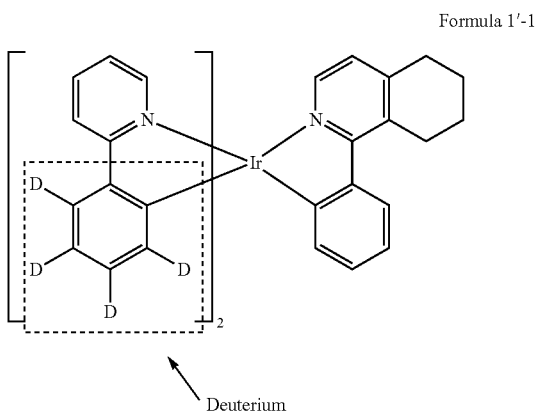

Formula 1'-1

Deuterium

A bond between a deuterium and a carbon may be shorter than a bond between a hydrogen and a carbon, and thus, a bond between a deuterium and a carbon may be stronger than a bond between a hydrogen and a carbon. Thus, an organic light-emitting device including an organometallic compound represented by Formula 1 may have improved lifetime.

An organometallic compound represented by Formula 1 may relatively rarely have a nonradiative transition, and thus, the efficiency of an organic light-emitting device including the organometallic compound may be improved.

Due to an organometallic compound represented by Formula 1, a HOMO energy level and hole current may be increased to lower a driving voltage of an organic light-emitting device including the organometallic compound.

An organometallic compound represented by Formula 1 may include, as described in Formula 1'-2 below, a cycloalkene:

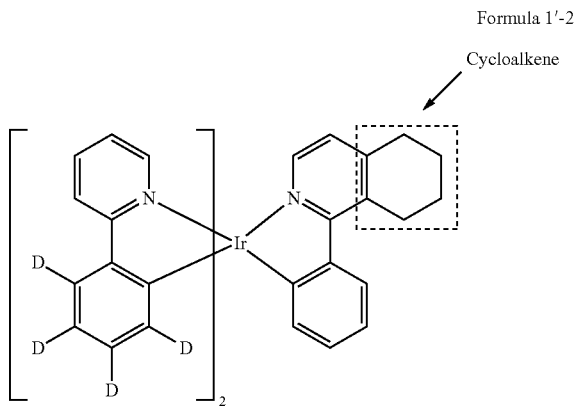

Formula 1'-2

Cycloalkene

Thus, a LUMO energy level of the organometallic compound may be increased to block electrons that are provided to an emission layer. In this regard, the lifetime of an organic light-emitting device including the organometallic compound may be increased.

Also, molecule-molecule stackings may be reduced due to a cycloalkene having a large steric hindrance, and thus, the efficiency of an organic light-emitting device including the cycloalkene may be improved.

In this regard, an organic light-emitting device including the organometallic compound represented by Formula 1 may provide low driving voltage, high efficiency, and long lifetime.

A method of synthesizing the organometallic compound represented by Formula 1 may be apparent to one of ordinary skill in the art by referring to Synthesis Examples used herein.

In this regard, the organometallic compound represented by Formula 1 may be suitable to be used as a dopant for an organic layer of an organic light-emitting device, for example, an emission layer among organic layers of the organic light-emitting device.

In some embodiments, provided is an organic light-emitting device including:

a first electrode;

a second electrode; and an organic layer disposed between the first electrode and the second electrode, wherein the organic layer includes an emission layer and at least one organometallic compound represented by Formula 1.

The organic light-emitting device includes an organic layer including the organometallic compound represented by Formula 1, thereby having low driving voltage, high efficiency, high luminance and long lifespan.

The organometallic compound represented by Formula 1 may be used in a pair of electrodes in an organic light-emitting device. For example, the organometallic compound represented by Formula 1 may be included in an emission layer. Here, the organometallic compound may be a dopant, and the emission layer may further include a host (in other words, an amount of the organometallic compound represented by Formula 1 may be smaller than an amount of the host).

The expression as used herein "(an organic layer) includes at least one organometallic compound" may be understood as "(organic layer) may include one organometallic compound represented by Formula 1 or two or more different organometallic compounds represented by Formula 1" For example, the organic layer may include only Compound 1 as the organometallic compound. In this regard, Compound 1 may be included in the emission layer of the organic light-emitting device.

Alternatively, the organic layer may include Compound 1 and Compound 2 as the organometallic compound. In this case, the Compound 1 and the Compound 2 may be included in an identical layer (for example, both the Compound 1 and the Compound 2 may be included in an emission layer).

The first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

In some embodiments, the first electrode may be an anode, the second electrode may be a cathode, and the organic layer may include:

i) a hole-transport region disposed between the first electrode and the emission layer, wherein the hole-transport region includes at least one selected from a hole injection layer, a hole-transport layer, and an electron blocking layer; and ii) an electron transport region disposed between the emission layer and the second electrode, wherein the electron transport region includes at least one selected from a hole blocking layer, an electron transport layer, and an electron injection layer.

The term "organic layer" as used herein means a single layer and/or a plurality of layers disposed between a first electrode and a second electrode in an organic light-emitting device. The "organic layer" may include an organic metal complex including a metal as well as an organic compound.

The FIGURE is a schematic view of an organic light-emitting device 10 according to an embodiment. Hereinafter, a structure and a method of manufacturing the organic light-emitting device according to an embodiment will be described with reference to the FIGURE. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by depositing or sputtering a material for forming the first electrode on the substrate. The first electrode 11 may be an anode. The material for the first electrode 11 may be selected from materials with a high work function for an easy hole injection. The first electrode 11 may be a reflective electrode, a semi-transmissive electrode, or a transmissive electrode. The material for the first electrode 110 may be selected from indium tin oxide (ITO), indium zinc oxide (IZO), tin oxide ($SnO_2$), and zinc oxide (ZnO). Alternatively, a metal such as magnesium (Mg), aluminum (Al), aluminum-lithium (Al—Li), calcium (Ca), magnesium-indium (Mg—In), and magnesium-silver (Mg—Ag) may be used as a material for the first electrode 11.

The first electrode 11 may have a single layer structure or a multi-layer structure including two or more layers. For example, the first electrode 11 may have a triple-layer structure of ITO/Ag/ITO, but it is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, hole transport layer, electron blocking layer, and buffer layer.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer (HIL) may be formed on the first electrode 11 by using various methods such as vacuum deposition, spin coating, casting, and Langmuir-Blodgett (LB) method.

When a hole injection layer is formed by using vacuum deposition, for example, the vacuum deposition may be performed at a temperature of a deposition temperature of about 100° C. to about 500° C., at a vacuum degree of about $10^{-8}$ torr to about $10^{-3}$ torr, and at a deposition rate of about 0.01 Angstroms per second (A/sec) to about 100 Å/sec in consideration of a compound to be deposited for forming a hole injection layer, and the structure and thermal characteristics of a hole injection layer to be formed. However an embodiment is not limited thereto.

A hole injection layer is formed by spin coating, for example, the spin coating may be performed at a coating rate of about 2,000 revolutions per minute (rpm) to about 5,000 rpm, and at a heat-treatment temperature of about 80° C. to 200° C. for removing a solvent depending on a compound to be deposited for forming a hole injection layer, and the structure and thermal characteristics of a hole injection layer to be formed. However an embodiment is not limited thereto.

The conditions for forming a hole transport layer and an electron blocking layer may be inferred based on the conditions for forming the hole injection layer.

The hole transport region, for example, may include at least one selected from m-MTDATA, TDATA, 2-TNATA, NPB, β-NPB, TPD, Spiro-TPD, Spiro-NPB, α-NPB, TAPC, HMTPD, TCTA(4,4',4"-tris(N-carbazolyl)triphenylamine (4,4',4"-tris(N-carbazolyl)triphenylamine)), Pani/DBSA (polyaniline/dodecylbenzenesulfonic acid:polyaniline/dodecyl benzenesulfonic acid), PEDOT/PSS(poly(3,4-ethylenedioxythiophene)/poly(4-styrenesulfonate):poly(3,4-ethylenedioxythiophene)/poly(4-styrene sulfonate)), Pani/CSA (polyaniline/camphor sulfonic acid:polyaniline/camphor sulfonic acid), PANI/PSS (polyaniline)/poly(4-styrene sulfonate):polyaniline)/poly(4-styrene sulfonate)), a compound represented by Formula 201 below, and a compound represented by Formula 202 below:

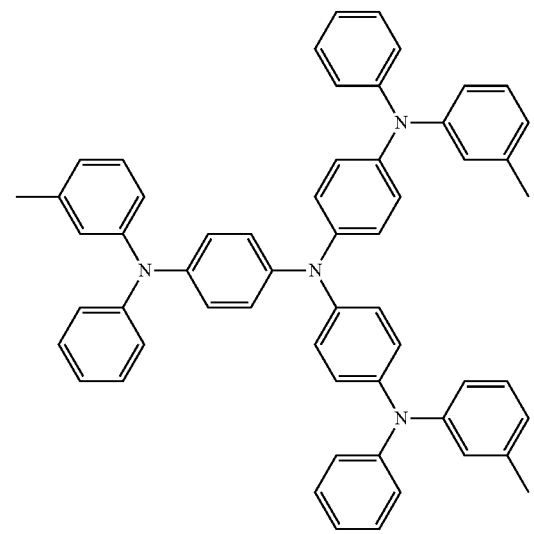

m-MTDATA

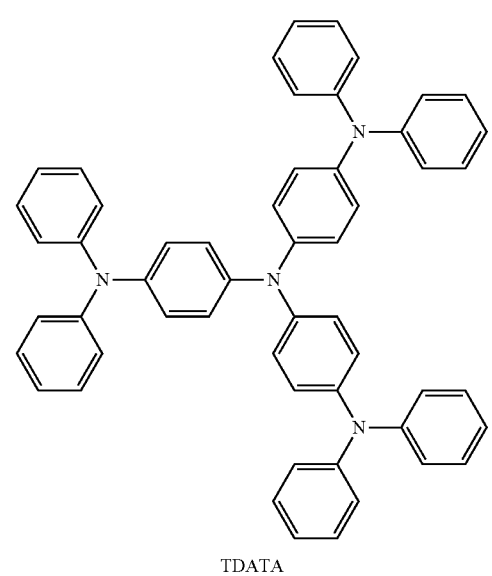

TDATA

-continued
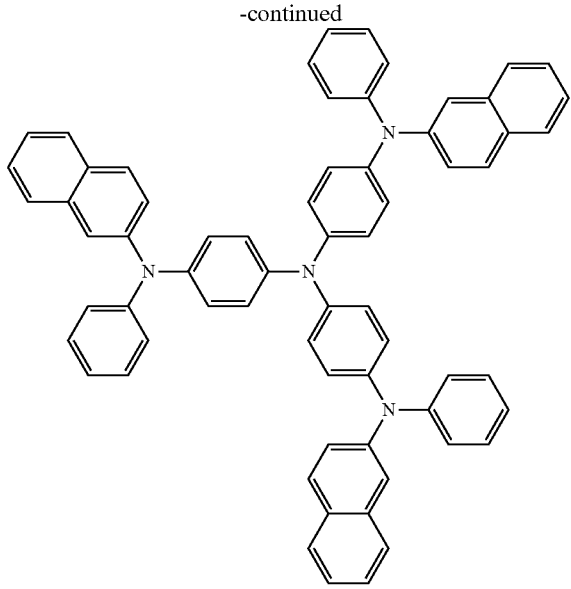
2-TNATA
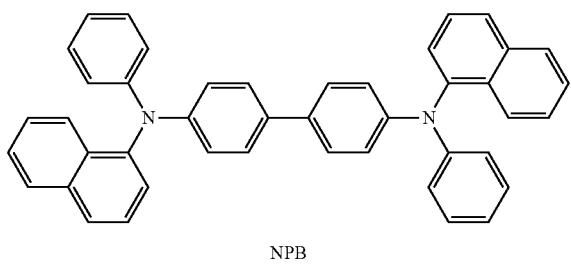
NPB
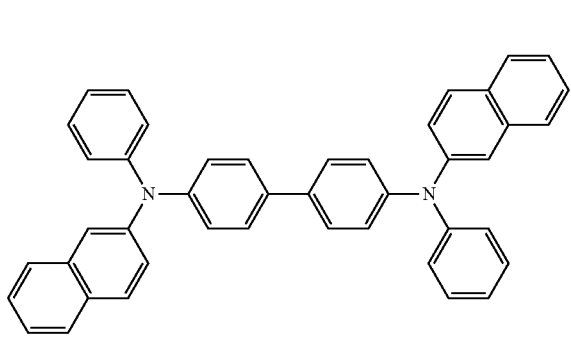
β-NPB
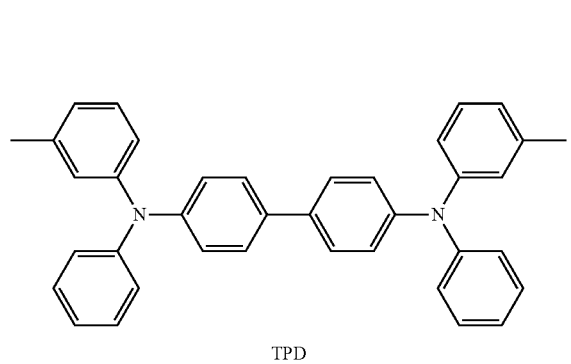
TPD
-continued
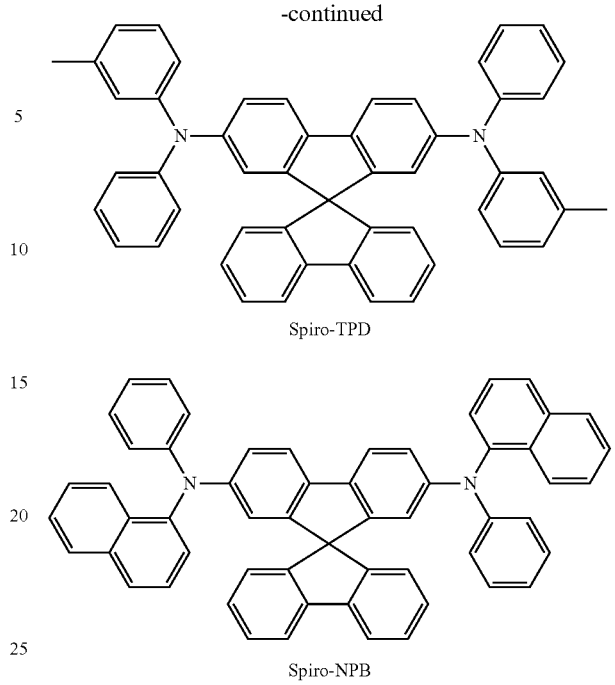
Spiro-TPD
Spiro-NPB
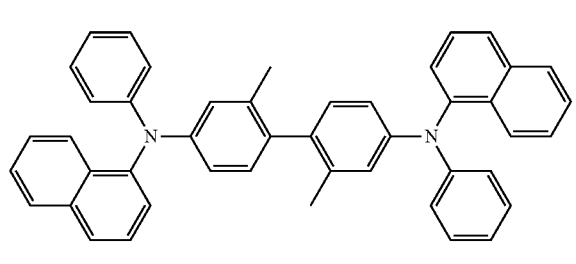
α-NPB
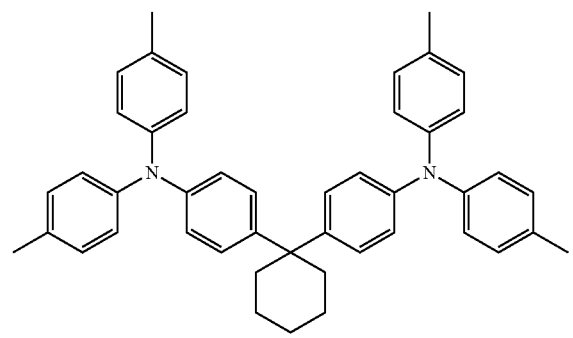
TAPC
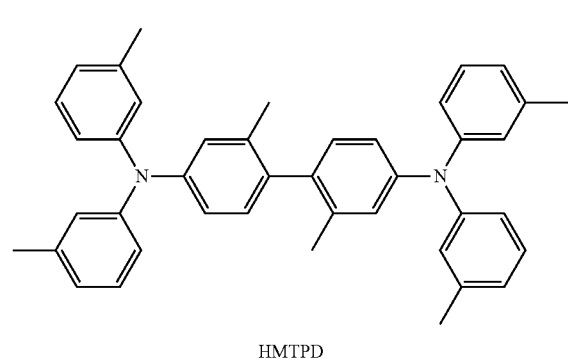
HMTPD

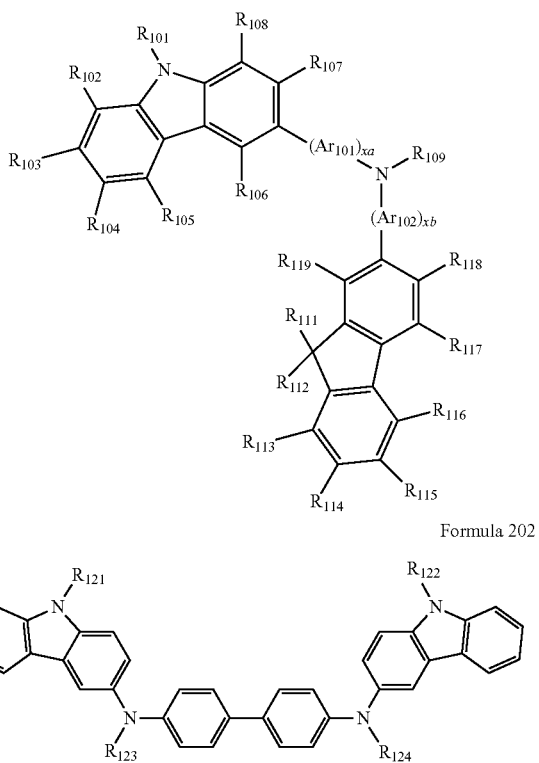

Formula 201

Formula 202 wherein, $Ar_{101}$ and $Ar_{102}$ in Formula 201 may be each independently selected from a phenylene, a pentalenylene, an indenylene, a naphthylene, an azulenylene, a heptalenylene, an acenaphthylene, a fluorenylene, a phenalenylene, a phenanthrenylene, an anthracenylene, a fluoranthenylene, a triphenylenylene, a pyrenylene, a chrysenylenylene, a naphthacenylene, a picenylene, a perylenylene, and a pentacenylene; and a phenylene, a pentalenylene, an indenylene, a naphthylene, an azulenylene, a heptalenylene, an acenaphthylene, a fluorenylene, a phenalenylene, a phenanthrenylene, an anthracenylene, a fluoranthenylene, a triphenylenylene, a pyrenylene, a chrysenylenylene, a naphthacenylene, a picenylene, a perylenylene, and a pentacenylene, each substituted with at least one selected from a deuterium, a halogen atom, a hydroxyl group, a cyano group, a nitro group, an amino group an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer of 0 to 5, or 0, 1, or 2. In some embodiments, xa may be 1 and xb may be 0, but they are not limited thereto.

In Formulae 201 and 202, $R_{101}$ to $R_{108}$, $R_{111}$ to $R_{119}$ and $R_{121}$ to $R_{124}$ may be each independently selected from a hydrogen, a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, and a hexyl group) and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a $C_1$-$C_{10}$ alkyl group and a $C_1$-$C_{10}$ alkoxy group, but they are not limited thereto.

$R_{109}$ in Formula 201 may be one selected from a phenyl group, a naphthyl group, an anthracenyl group, a biphenyl group, and a pyridinyl group; and a phenyl group, a naphthyl group, an anthracenyl group, a biphenyl group, and a pyridinyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

According to an embodiment, the compound represented by Formula 201 may also be represented by Formula 201A below, but is not limited thereto:

Formula 201A

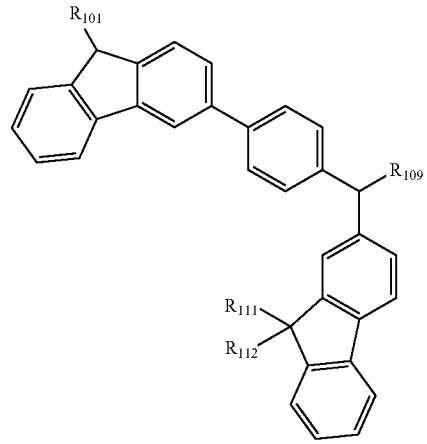

Descriptions of $R_{101}$, $R_{111}$, $R_{112}$, and $R_{109}$ in Formula 201A are the same as provided herein.

In some embodiments, the compound represented by Formula 201 and the compound represented by Formula 202 may include Compounds HT1 to HT20, but they are not limited thereto:

HT1
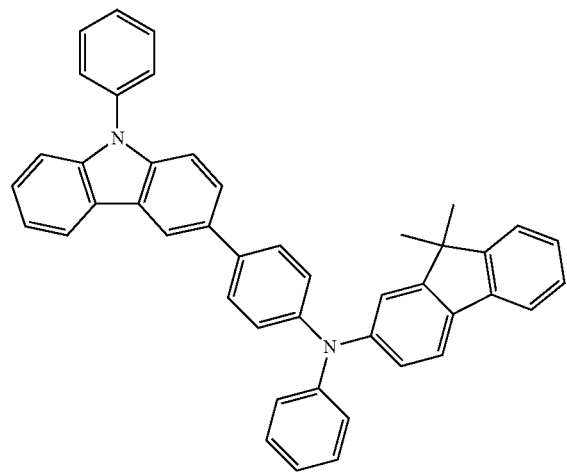
HT3
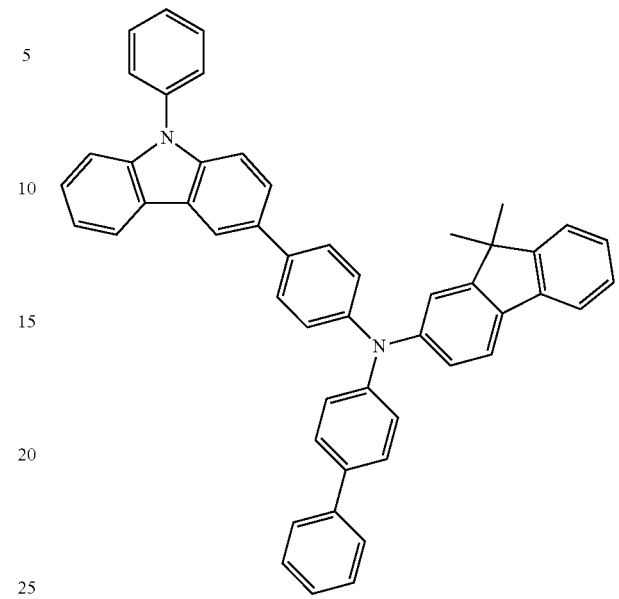
HT2
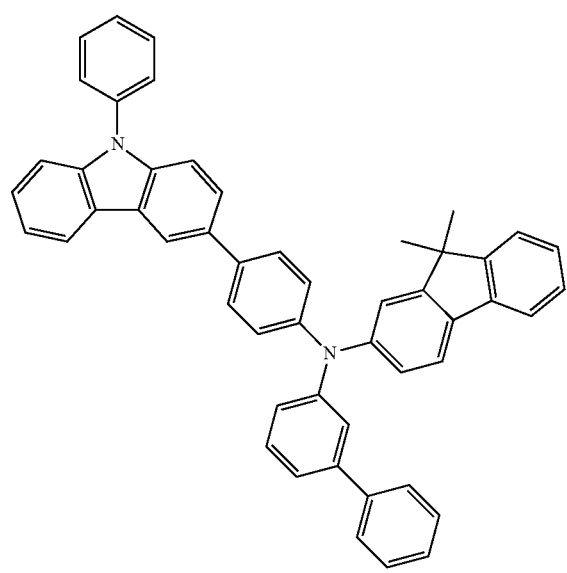
HT4
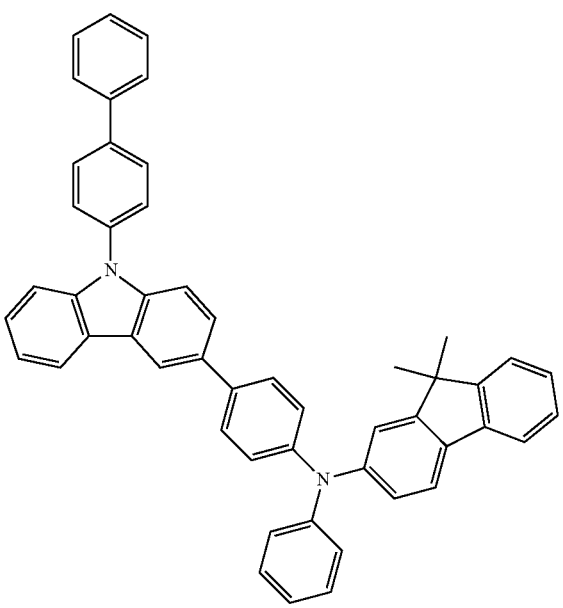

HT5
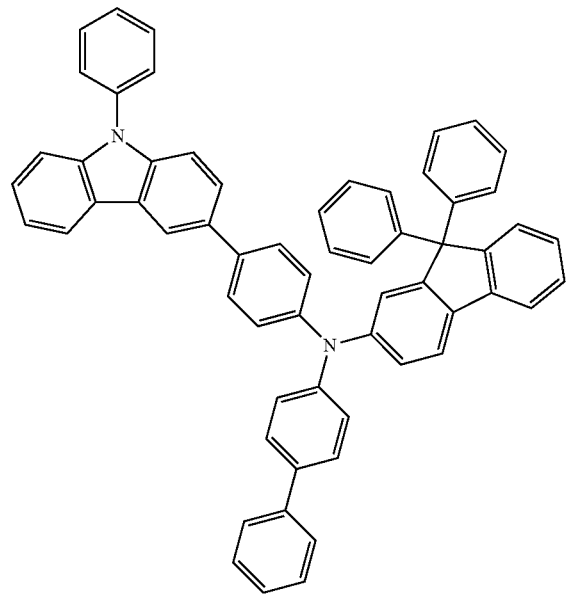
HT6
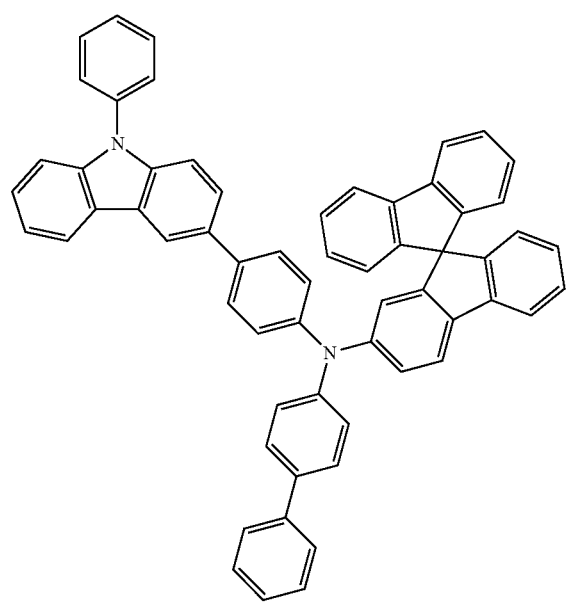
HT7
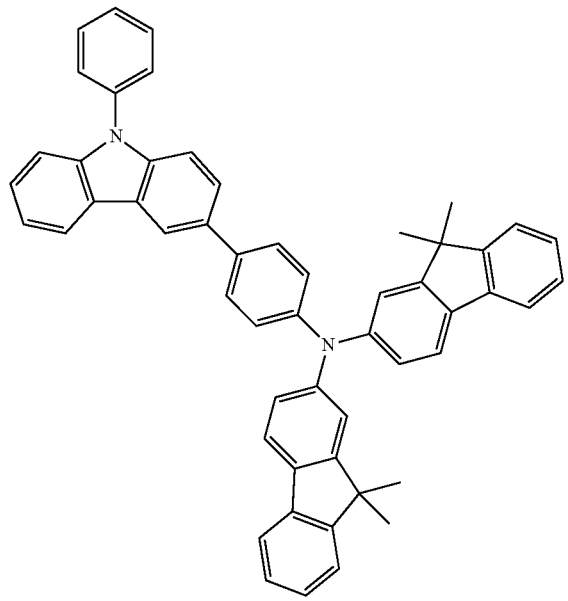
HT8
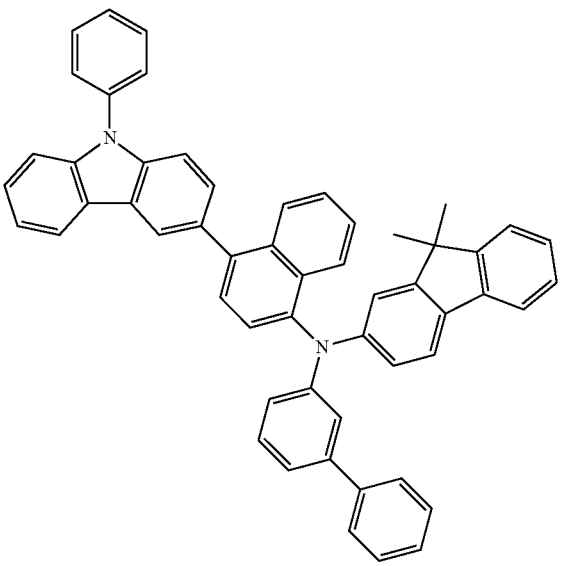

HT9
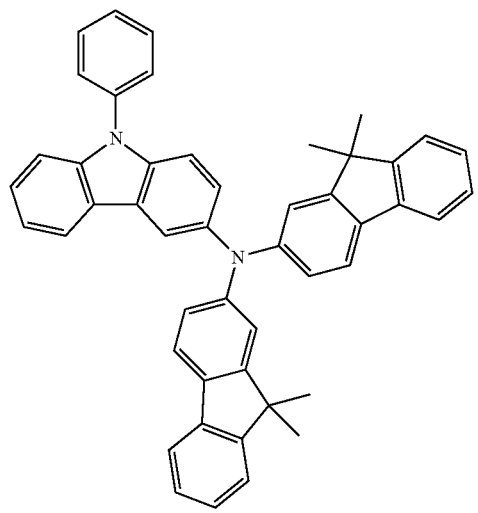
HT11
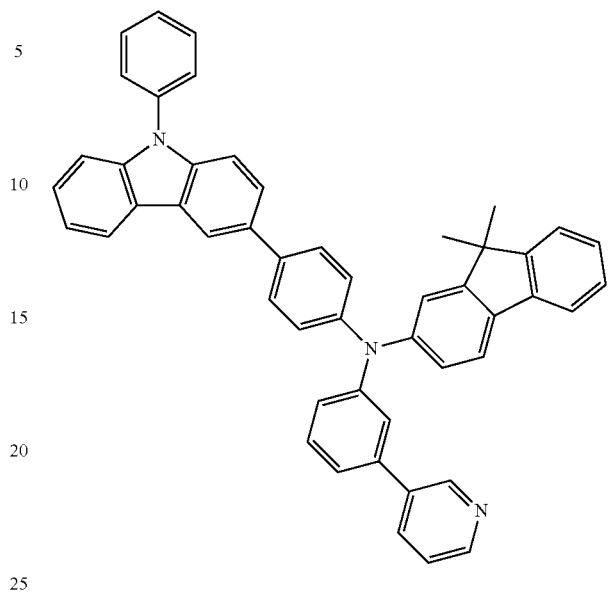
HT12
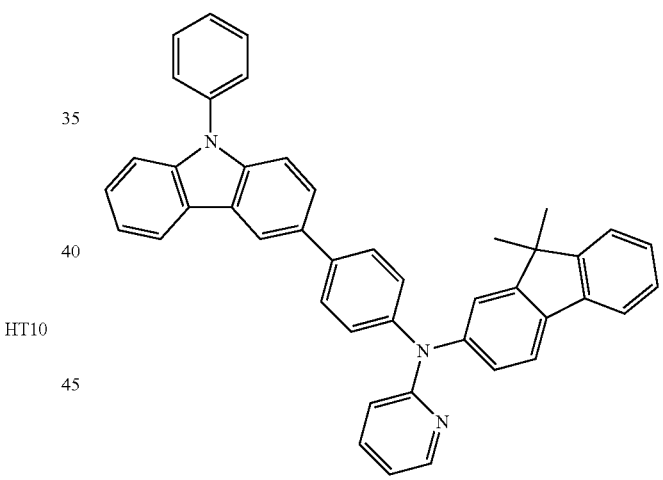
HT10
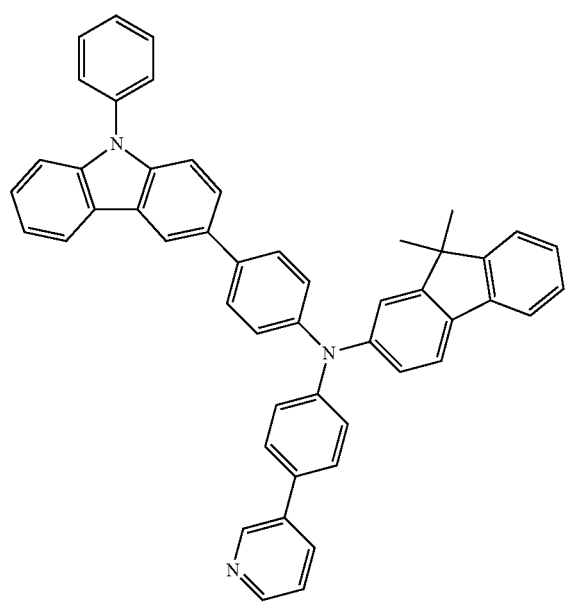
HT13
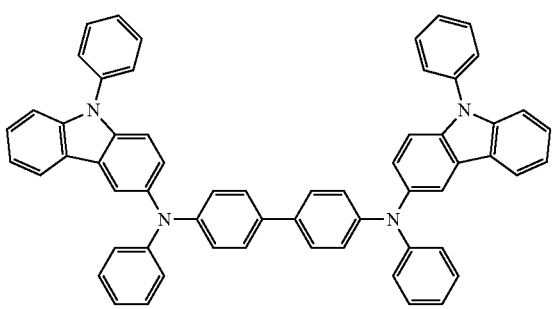

-continued

HT14
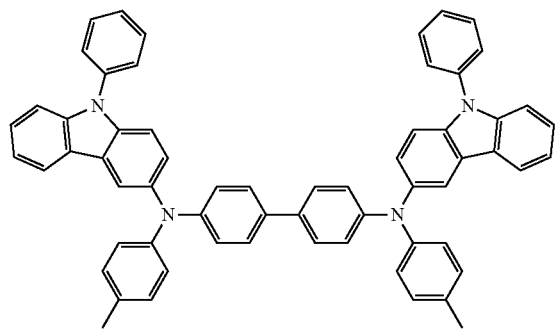

HT15
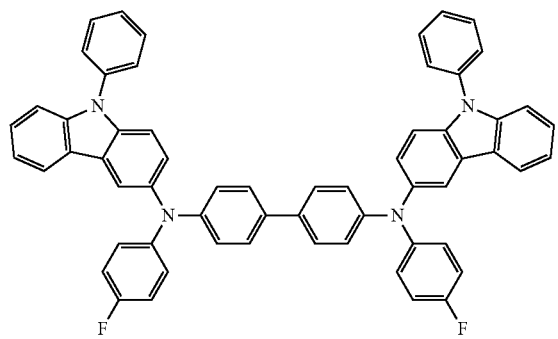

HT16
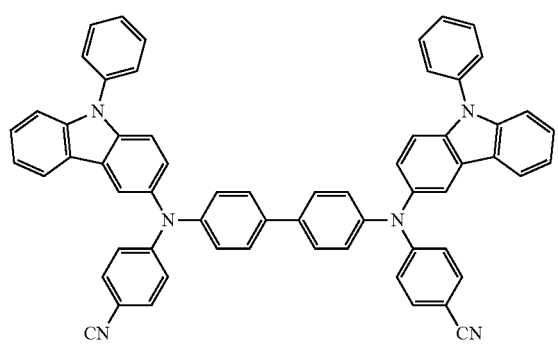

HT17
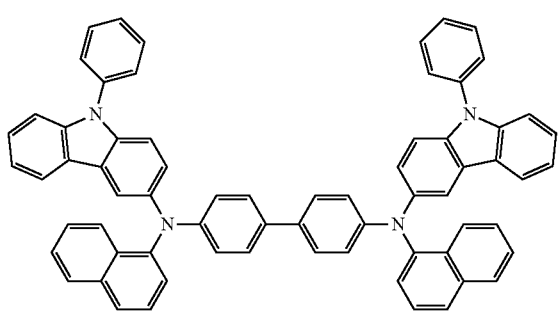

-continued

HT18
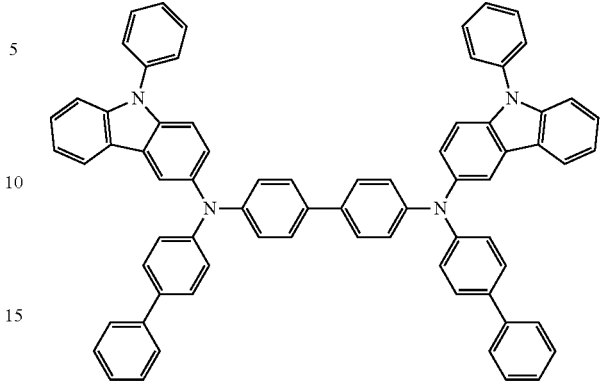

HT19
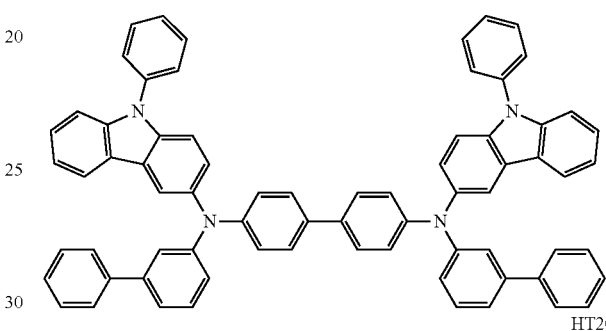

HT20
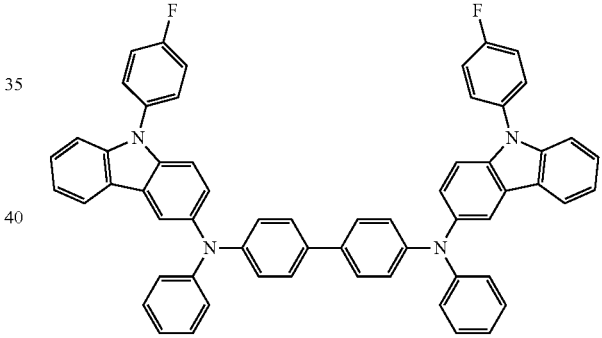

A thickness of the hole transport region may be in a range of about 100 Å to about 10,000 Å, for example, about 100 Å to about 1,000 Å. When the hole transport region includes a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but is not limited thereto. For example, non-limiting examples of the p-dopant include a quinone derivative such as 7,7,8,8-tetracyanoquinodimethane (TCNQ) and 2,3,5,6-tetrafluoro-tetracyano-7,7,8,8-tetracyanoquinodimethane (F4-TCNQ); a metal oxide such as a tungsten oxide and s molybdenum oxide; a cyano group-containing compound such as Compound HT-D1 below, but are not limited thereto.

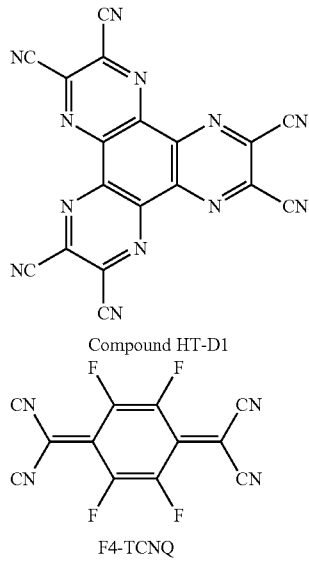

The hole transport region may further include a buffer layer.

The buffer layer may compensate for an optical resonance distance according to a wavelength of light emitted from the emission layer to improve the efficiency of an organic light-emitting device.

An emission layer (EML) may be formed on the hole transport region by using various methods, such as vacuum deposition, spin coating, casting, or an LB method. When the emission layer is formed by vacuum deposition or spin coating, deposition and coating conditions for the emission layer may be generally similar to the conditions for forming a hole injection layer, though the conditions may vary depending on the compound used.

The emission layer may include a host and a dopant and the dopant may include the organometallic compound represented by Formula 1.

The host may include at least one selected from TPBi, TBADN, AND (also known as "DNA"), CBP, CDBP, and TCP:

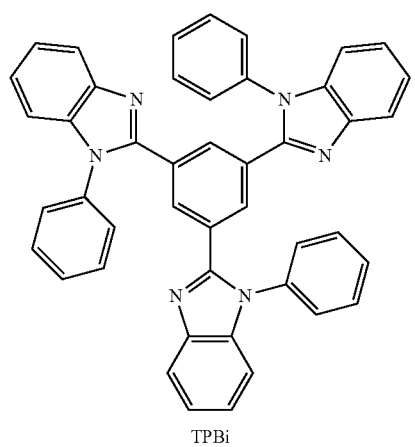

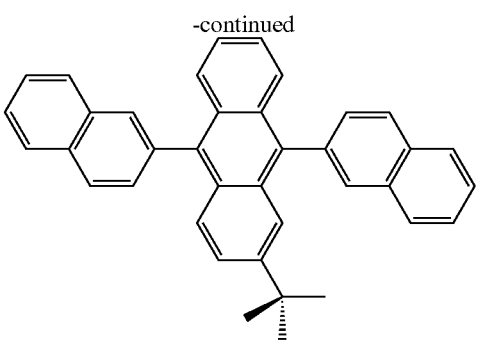

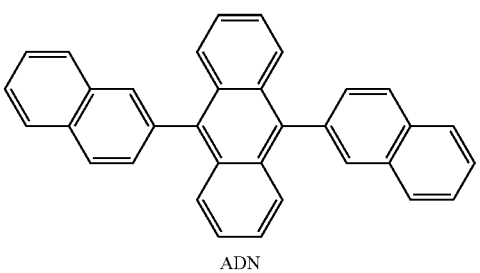

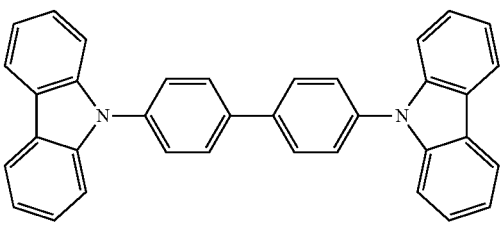

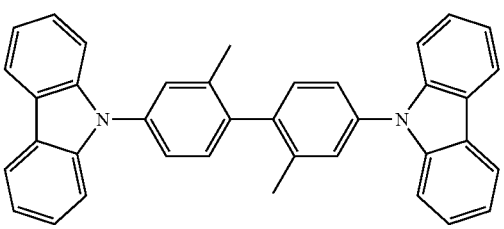

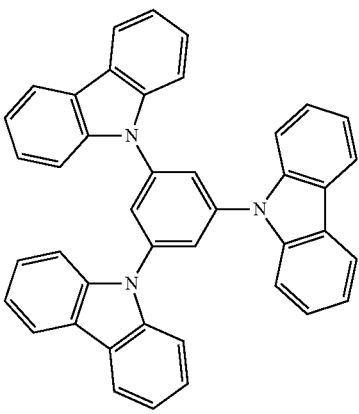

Alternatively, the host may further include a compound represented by Formula 301:

Formula 301

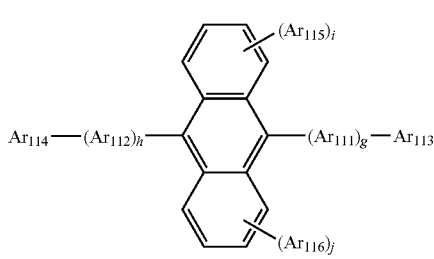

$Ar_{111}$ and $Ar_{112}$ in Formula 301 may be each independently selected from a phenylene, a naphthylene, a phenanthrenylene, and a phenylene; and a phenylene, a naphthylene, a phenanthrenylene, a fluorenyl group, and a pyrenylene, each substituted with at least one selected from a phenyl group, a naphthyl group, and an anthracenyl group.

$Ar_{113}$ to $Ar_{116}$ in Formula 301 may be each independently selected from a $C_1$-$C_{10}$ alkyl; a phenyl group, a naphthyl group, a phenanthrenyl group, and a pyrenyl group; and a phenyl group, a naphthyl group, a phenanthrenyl group, a fluorenyl group, and a pyrenyl group, each substituted with at least one selected from a phenyl group, a naphthyl group, and an anthracenyl group.

g, h, i, and j in Formula 301 may each independently be an integer of 0 to 4, for example, 0, 1, or 2.

$Ar_{113}$ and $Ar_{116}$ in Formula 301 may be each independently selected from a $C_1$-$C_{10}$ alkyl phenyl group, substituted with at least one selected from a naphthyl group, and an anthracenyl group;

a phenyl group, a naphthyl group, an anthracenyl group, a pyrenyl group, a phenanthrenyl group, and a fluorenyl group;

a phenyl group, a naphthyl group, an anthracenyl group, a pyrenyl group, a phenanthrenyl group, and a fluorenyl group, each substituted with at least one selected from a deuterium, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; and

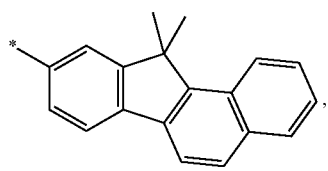 [SMILES: *c1ccc2c(c1)C(C)(C)c1c-2ccc2ccccc12]

but they are not limited thereto.

Alternatively, the host may include a compound represented by Formula 302:

Formula 302

Descriptions of $Ar_{122}$ to $Ar_{125}$ in Formula 302 are the same as the description of $Ar_{113}$ in Formula 301.

$Ar_{126}$ and $Ar_{127}$ in Formula 302 may each independently be a $C_1$-$C_{10}$ alkyl group (for example, a methyl group, an ethyl group, or a propyl group).

k and l in Formula 302 may each independently be an integer of 0 to 4.

For example, k and l may be 0, 1, or 2.

For example, the compound represented by Formula 201 and the compound represented by Formula 302 may include Compounds HT1 to HT42, but they are not limited thereto:

H1

H2

H3

H4

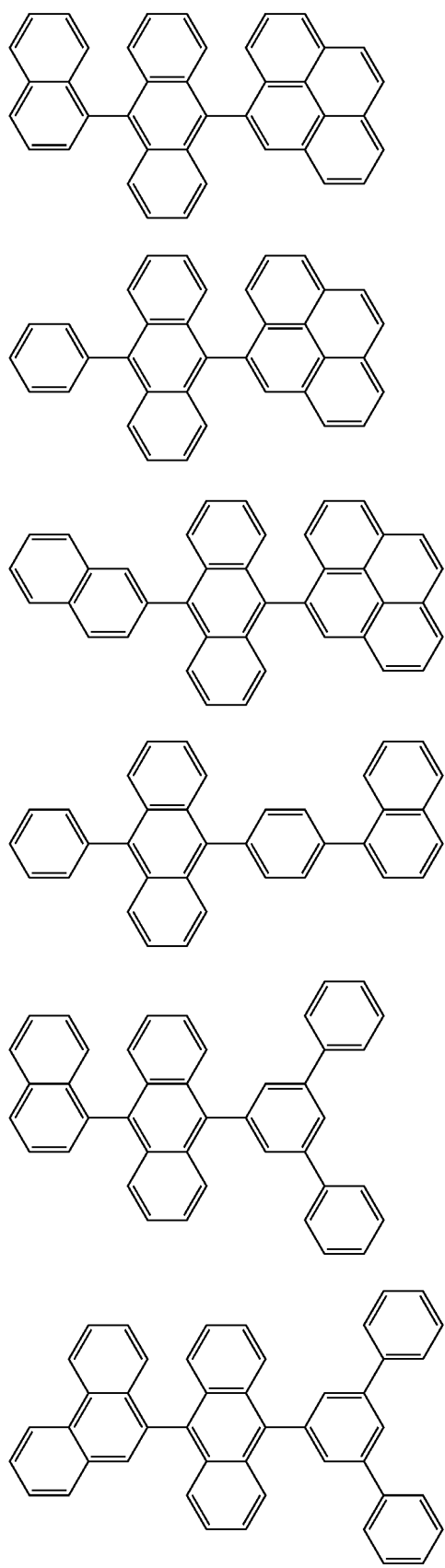
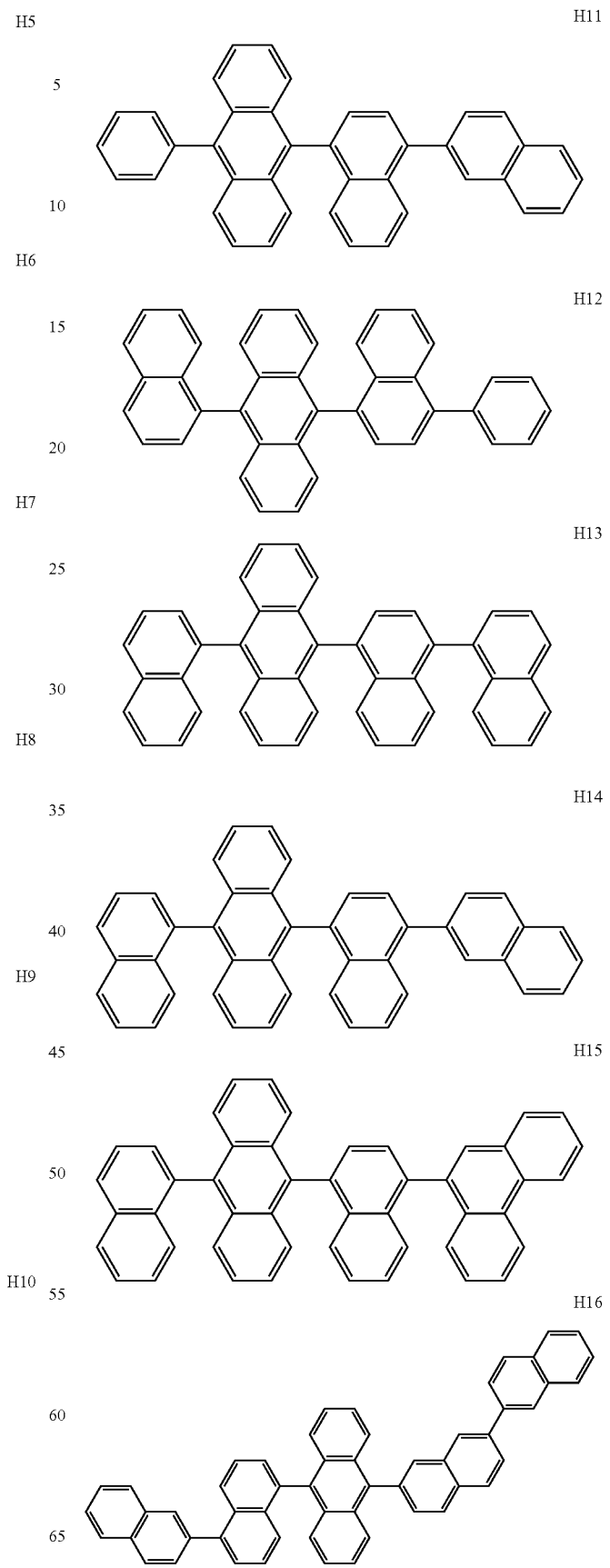

H17
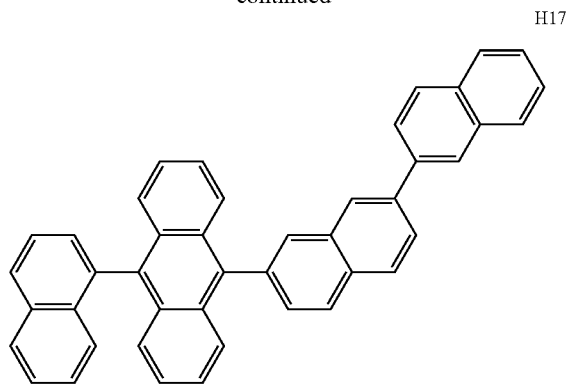
H18
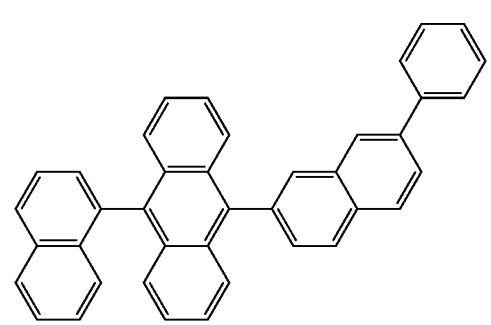
H19
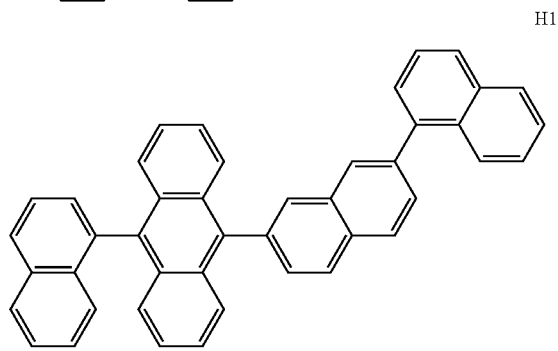
H20
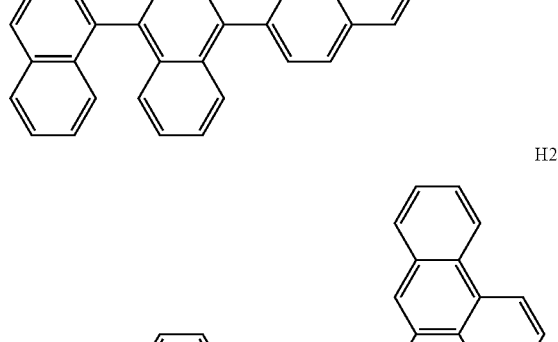
H21
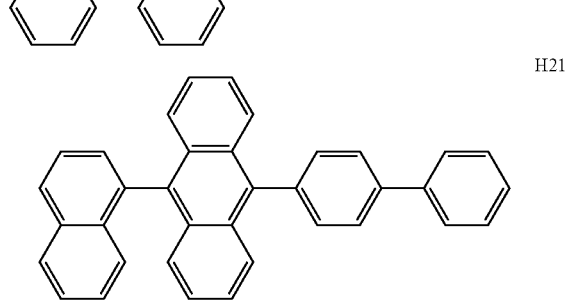
H22
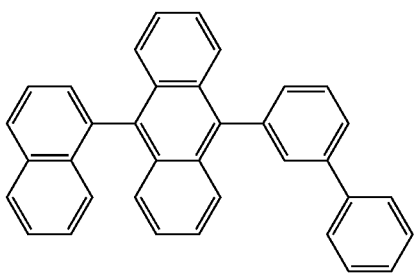
H23
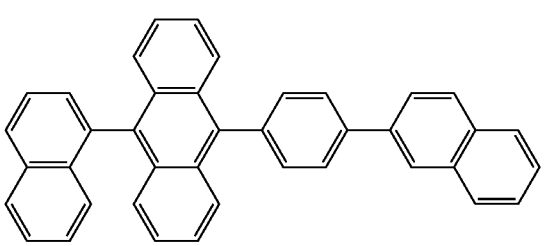
H24
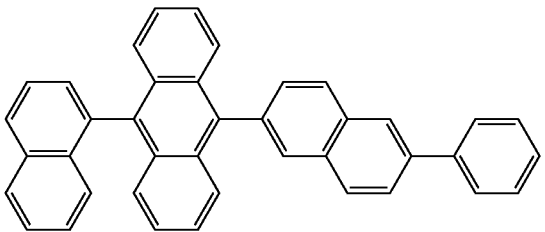
H25
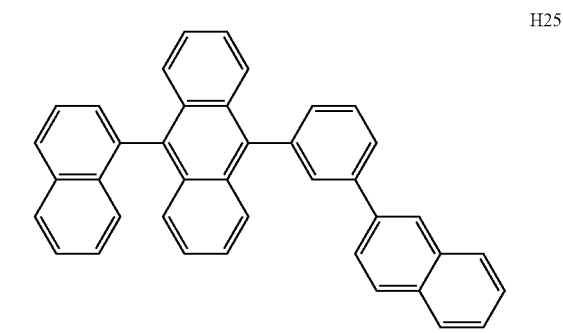
H26
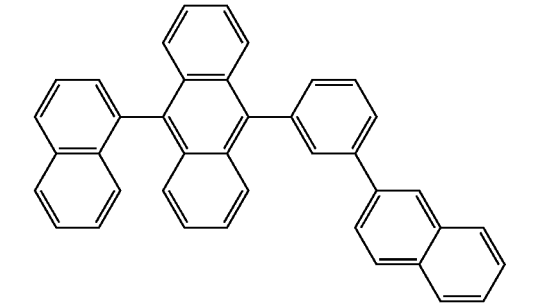

H27
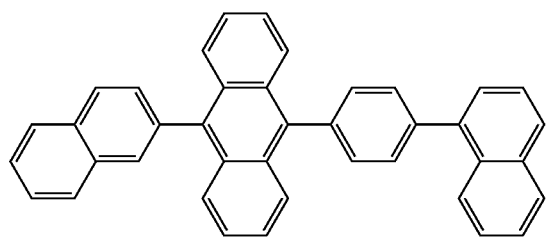
H28
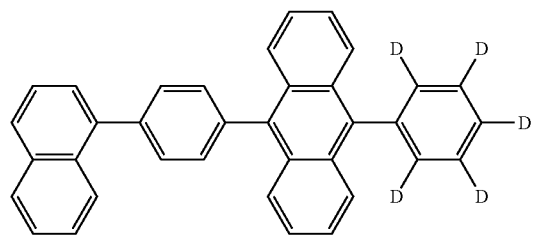
H29
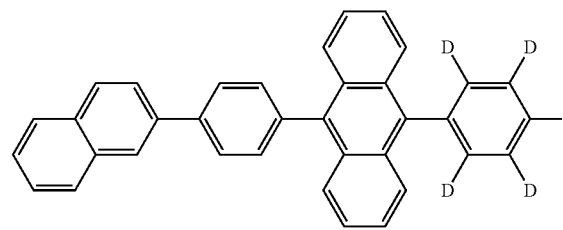
H30
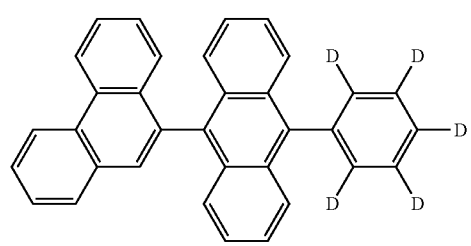
H31
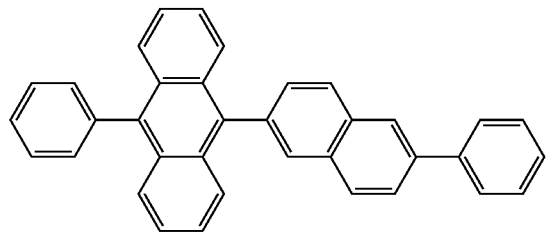
H32
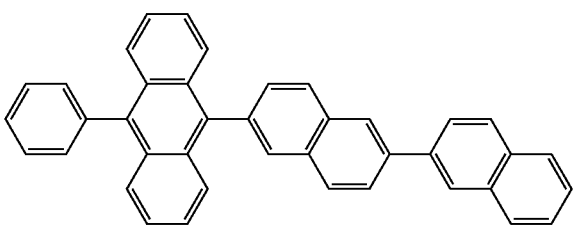
H33
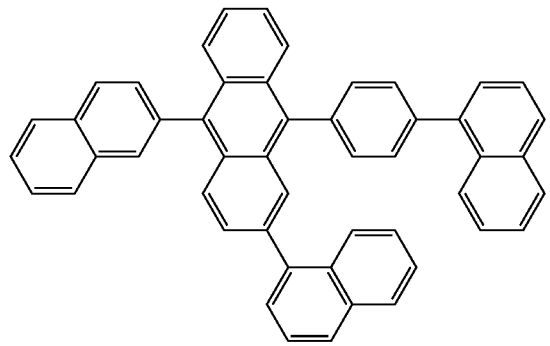
H34
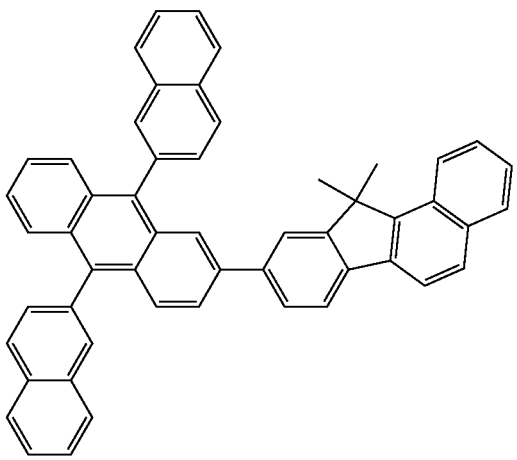
H35
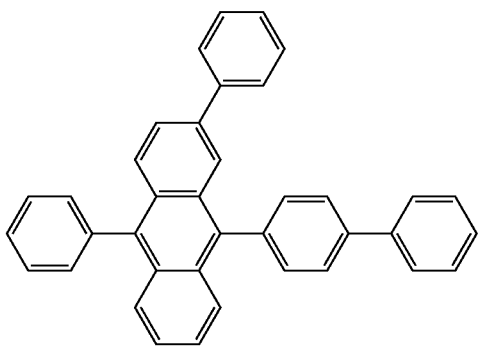

H36
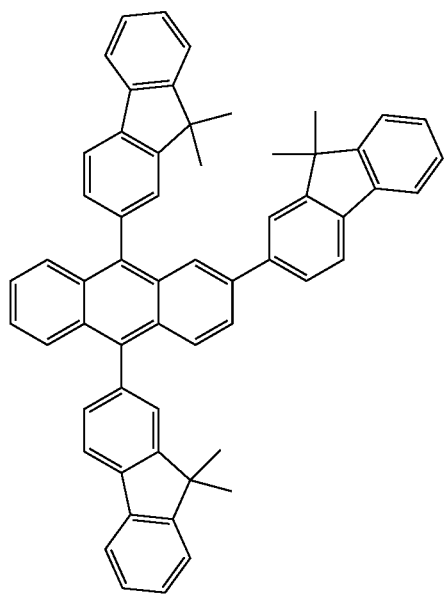
H37
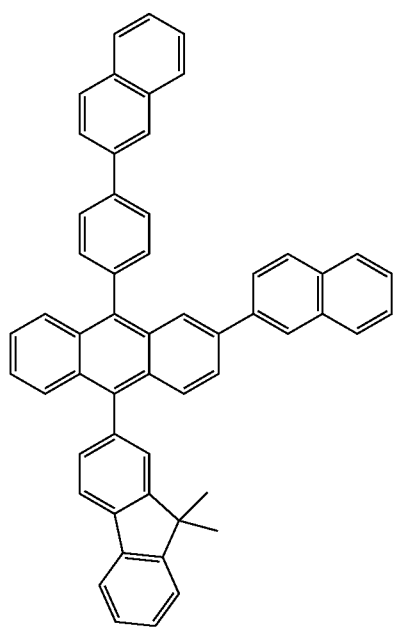
H38
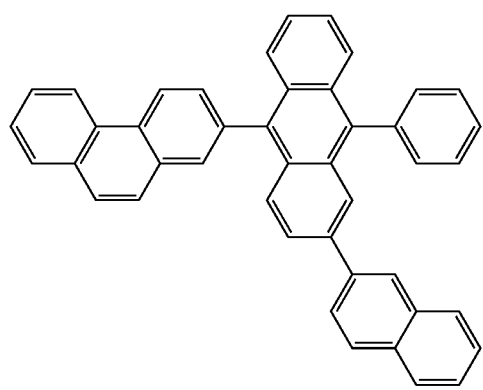
H39
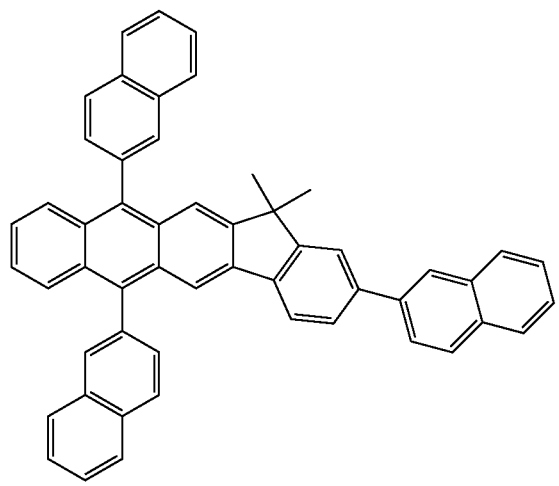
H40
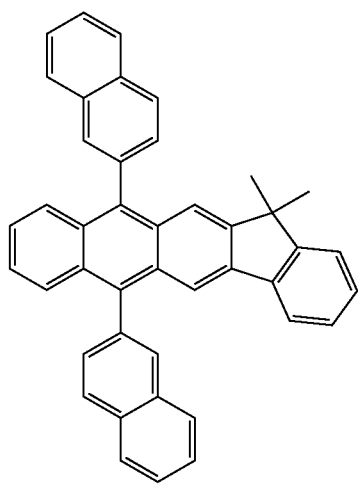
H41
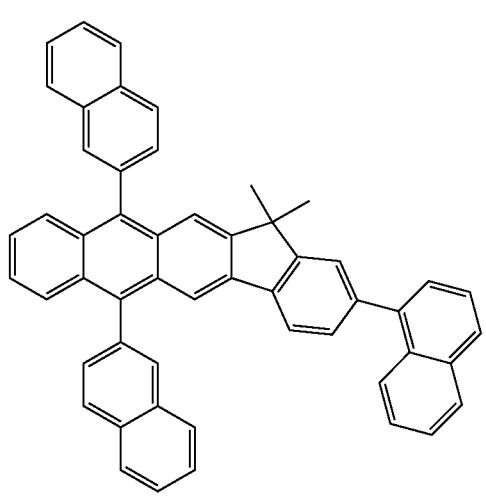

H42

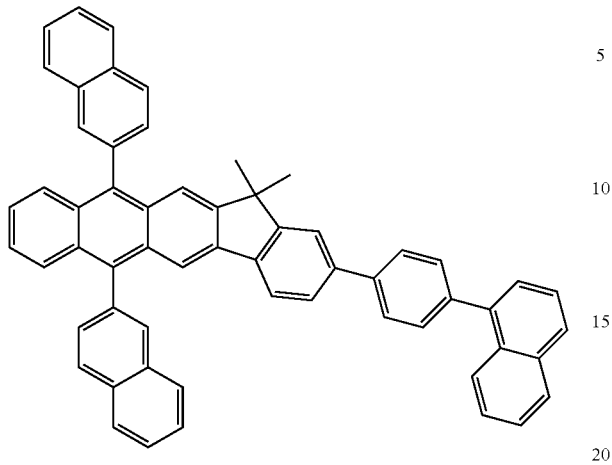

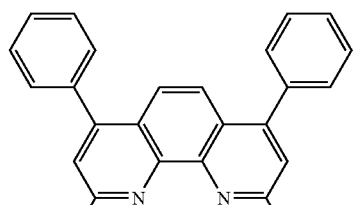
BCP

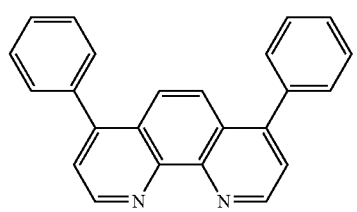
Bphen

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light or other various embodiments are possible.

When the emission layer includes a host and a dopant, an amount of dopant is, in general, in a range of about 0.01 part by weight to about 15 parts by weight based on 100 parts by weight of the host, but is not limited thereto.

A thickness of the emission layer may be in a range of about 100 Angstroms (Å) to about 1,000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer, but is not limited thereto.

In some embodiments, the electron transport region may have a structure of a hole blocking layer/an electron transport layer/an electron injection layer or an electron transport layer/an electron injection layer, but it is not limited thereto. The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer may, for example, include at least one selected from BCP and Bphen, but is not limited thereto.

A thickness of the hole blocking layer may be in a rage of about 20 Å to about 1,000 Å, for example, about 30 Å to about 300 Å. When the thickness of the hole blocking layer is within this range, excellent hole blocking characteristics may be obtained without a substantial increase in driving voltage.

The electron transport layer may include at least one selected from BCP, Bphen, as defined above, and Alq₃, Balq, TAZ and NTAZ below.

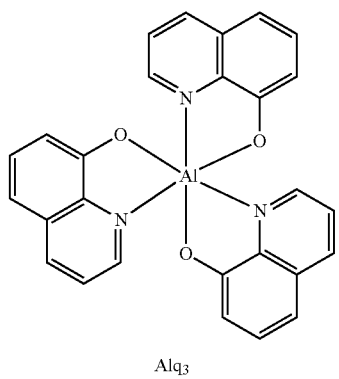
Alq₃

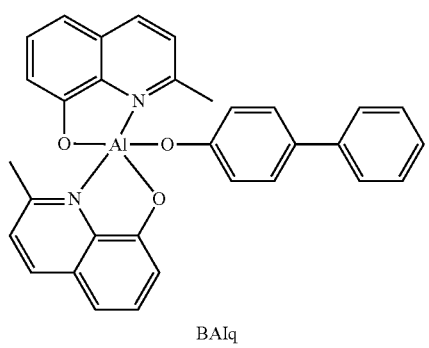
BAlq

-continued

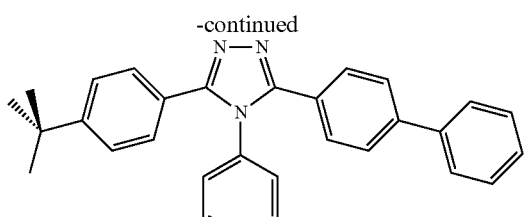

TAZ

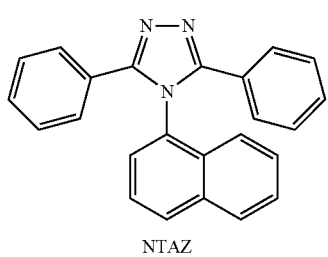

NTAZ

Alternatively, the electron transport layer may include at least one selected from Compounds ET1 and ET2, but is not limited thereto.

ET1

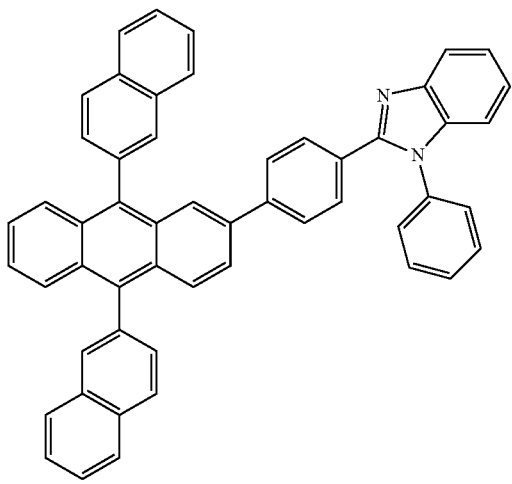

ET2

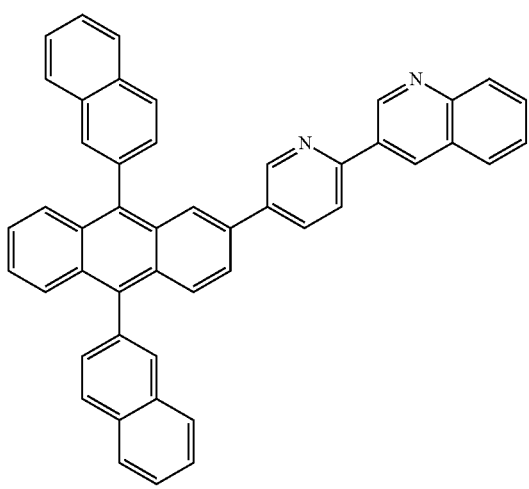

A thickness of the electron transport layer may be in a rage of about 100 Å to about 1,000 Å, for example, about 150 Å to about 500 Å. When the thickness of the electron transport layer is within this range, excellent electron transport characteristics may be obtained without a substantial increase in driving voltage.

The electron transport layer may further include a metal-containing material as well as the materials described above.

The metal-containing material may include a Li complex. The Li complex may include, for example, Compound ET-D1 (lithium quinolate, LiQ) or ET-D2.

ET-D1

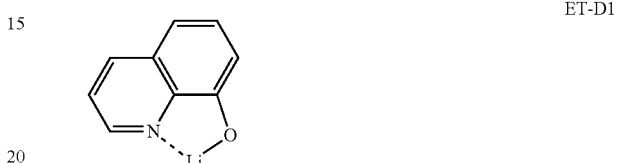

ET-D2

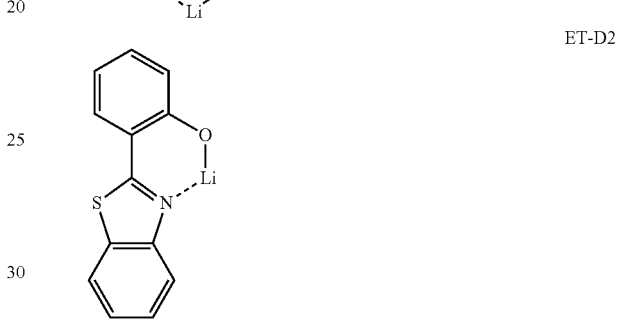

The electron transport region may include an electron injection layer (EIL) that facilitates electron injection from the second electrode 19.

The electron injection layer may include at least one selected from, LiF, NaCl, CsF, $Li_2O$, and BaO.

A thickness of the electron injection layer may be in a range of about 1 Å to about 100 Å, for example, about 3 Å to about 90 Å. When the thickness of the electron injection layer is within this range, excellent electron injection characteristics may be obtained without a substantial increase in driving voltage.

The second electrode 19 is disposed on the organic layer 15. The second electrode 19 may be a cathode. A material for the second electrode 19 may be a material having a relatively low work function, such as a metal, an alloy, an electrically conductive compound, and a mixture thereof. Detailed examples of the material for forming the second electrode 19 include lithium (Li), magnesium (Mg), aluminum (Al), aluminum-lithium (Al—Li), calcium (Ca), magnesium-indium (Mg—In), and magnesium-silver (Mg—Ag). Alternatively, ITO or IZO may be used to form a transmissive second electrode 19 to manufacture a top emission light-emitting device, and other various embodiments may also be possible.

Hereinbefore, the organic light-emitting device has been described with reference to the FIGURE, but it is not limited thereto.

A $C_1$-$C_{60}$ alkyl group as used herein refers to a linear or branched aliphatic hydrocarbon monovalent group having 1 to 60 carbon atoms. Detailed examples thereof include a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by -$OA_{101}$ (wherein, $A_{101}$ is the $C_1$-$C_{60}$ alkyl group). Detailed examples thereof include a methoxy group, an ethoxy group, or an isopropyloxy group.

A $C_2$-$C_{60}$ alkenyl group as used herein refers to a structure including at least one carbon-carbon double bond in the middle or at a terminal of the $C_2$-$C_{60}$ alkyl group. Detailed examples thereof include an ethenyl group, a propenyl group, and a butenyl group. A $C_2$-$C_{60}$ alkenylene group as used herein refers to a divalent group having the same structure as a $C_2$-$C_{60}$ alkenyl group.

A $C_2$-$C_{60}$ alkynyl group as used herein refers to a structure including at least one carbon-carbon triple bond in the middle or at a terminal of the $C_2$-$C_{60}$ alkyl group. Detailed examples thereof include a ethynyl group, a propynyl group. A $C_2$-$C_{60}$ alkynylene group as used herein refers to a divalent group having the same structure as a $C_2$-$C_{60}$ alkynyl group.

A $C_3$-$C_{10}$ cycloalkyl group as used herein refers to a monovalent saturated hydrocarbon monocyclic group including 3 to 10 carbon atoms. Detailed examples thereof include a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent monocyclic group including at least one hetero atom selected from N, O, P and S as a ring-forming atom and 1 to 10 carbon atoms. Detailed examples thereof include a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group including 3 to 10 carbon atoms and at least one double bond in the ring thereof, which is not aromatic. Detailed examples thereof include a cyclopentenyl group, a cyclohexenyl group, and a cycloheptenyl group. A $C_3$-$C_{10}$ cycloalkenylene group as used herein refers to a divalent group having the same structure as a $C_3$-$C_{10}$ cycloalkenyl group.

A $C_1$-$C_{10}$ heterocycloalkenyl group as used herein refers to a monovalent monocyclic group including at least one hetero atom selected from N, O, P, and S as a ring-forming atom, 1 to 10 carbon atoms, and at least one double bond in its ring. Detailed examples of the $C_1$-$C_{10}$ heterocycloalkenyl group include a 2,3-dihydrofuranyl group and a 2,3-dihydrothiophenyl group. A $C_1$-$C_{10}$ heterocycloalkenylene group as used herein refers to a divalent group having the same structure as a $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group include a phenyl group, a naphthyl group, an anthracenyl group, a phenanthrenyl group, a pyrenyl group, or a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system including at least one hetero atom selected from N, O, P and S as a ring-forming atom, and 1 to 60 carbon atoms, and a $C_1$-$C_{60}$ heteroarylene group refers to a divalent group having a carbocyclic aromatic system including at least one hetero atom selected from N, O, P and S as a ring-forming atom, and 1 to 60 carbon atoms. Detailed examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group include two or more rings, the rings may be fused to each other.

A $C_6$-$C_{60}$ aryloxy group as used herein refers to -$OA_{102}$ (wherein, $A_{102}$ refers to the $C_6$-$C_{60}$ aryl group), and the $C_6$-$C_{60}$ arylthio group refers to -$SA_{103}$ (wherein, $A_{103}$ refers to the $C_6$-$C_{60}$ aryl group)

A monovalent non-aromatic condensed polycyclic group as used herein refers to a monovalent group including two or more rings condensed to each other and only carbon atoms as ring-forming atom (for example, having 8 to 60 carbon atoms), wherein the molecular structure as a whole is non-aromatic. Detailed examples of the non-aromatic condensed polycyclic group include a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group including two or more rings condensed to each other, and a hetero atom selected from N, O, P, and S, other than carbon atoms as a ring-forming atom, (for example, having 1 to 60 carbon atoms) wherein the molecular structure as a whole is non-aromatic. Detailed examples of the monovalent non-aromatic condensed heteropolycyclic group include a carbazolyl group. A divalent non-aromatic condensed heteropolycyclic group as used herein refers to a divalent group having the same structure as the monovalent non-aromatic condensed hetero-polycyclic group.

Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples. The expression "'B' was used instead of 'A'" in Synthesis Examples below means that the used amount of 'B' is the same as that of 'A' in terms of a mole to mole ratio.

EXAMPLE

Synthesis Example 1

Synthesis of Compound 1

Compound 1 was synthesized according to Reaction Scheme 1:

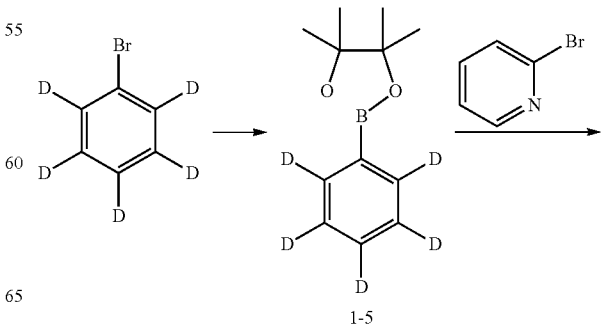

Reaction Scheme 1

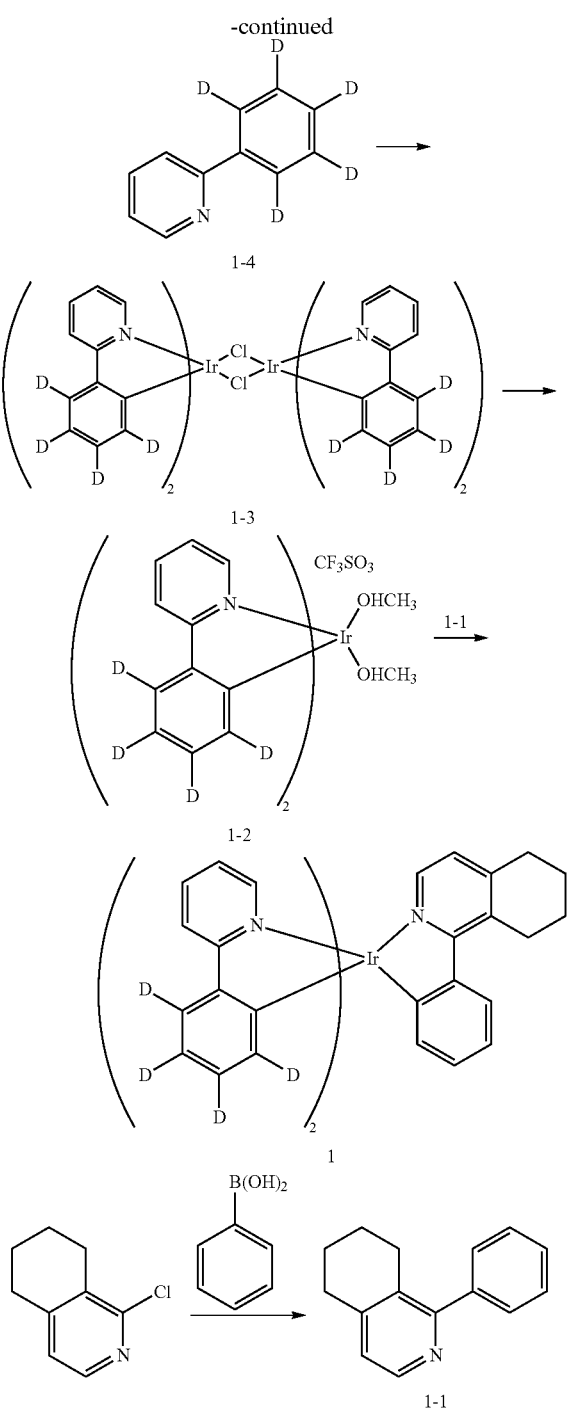

1) Synthesis of Intermediate 1-5

20.0 grams (g) (123.4 millimoles (mmol)) of bromobenzene-d5 was dissolved in 400 milliliters (ml) of tetrahydrofuran. 48.1 ml (150.0 mmol) of 2.5 molar (M) n-BuLi (in hexane) was slowly added thereto at a temperature of −78° C. and the resultant was stirred for about 1 hour. After that, 38 ml (139.0 mmol) of 2-isopropoxy-4,4,5,5-tetramethyl-1,3,2-dioxaborolane was added thereto and the resultant was stirred at a temperature of −78° C. for about 1 hour. Then, the resultant was stirred at room temperature for about 18 hours. When the reaction was complete, 100 ml of water was added thereto at room temperature, and an extraction process was performed by adding 400 ml of ethyl acetate and 500 ml of brine. The organic layer obtained therefrom was dried by using magnesium sulfate, and further distilled at a reduced pressure. The resultant obtained therefrom was purified by column chromatography to obtain about 12.5 g (60.0 mmol, yield of 48%) of Intermediate 1-5. The obtained compound was confirmed by LC-MS.

LC-MS m/z=210(M+H)$^+$.

2) Synthesis of Intermediate 1-4

12.0 g (57.0 mmol) of Intermediate 1-5 and 7.0 g (44.0 mmol) of 2-bromopyridine were dissolved in 300 ml of acetonitrile. 0.5 g (2.2 mmol) of palladium(II) acetate and 2.3 g (8.8 mmol) of triphenylphosphine were added thereto at room temperature and the resultant was stirred for about 5 minutes. After that, 4.9 g (88.0 mmol) of potassium hydroxide was added thereto and the resultant was heated at a temperature of 70° C. for about 22 hours. When the reaction is complete, the resultant was cooled to room temperature, and a floating material was filtered. The obtained organic material was distilled at a reduced pressure, and 300 ml of ethyl acetate and 50 ml of brine were added thereto to perform an extraction process. The organic layer obtained therefrom was dried by using magnesium sulfate and then distilled at a reduced pressure. The resultant obtained therefrom was purified by column chromatography to obtain about 6.0 g (37.4 mmol, yield of 85%) of Intermediate 1-4. The obtained compound was confirmed by LC-MS.

LC-MS m/z=161(M+H)$^+$.

3) Synthesis of Intermediate 1-3

6.0 g (37.4 mmol) of Intermediate 1-4 was dissolved in 60 ml of ethoxyethanol and 20 ml of distilled water, and 5.7 g (16.4 mmol) of Iridium(III) chloride hydrate was added thereto at room temperature and the resultant was refluxed while heating at a temperature of 120° C. for a day. When the reaction was complete, the resultant was cooled to room temperature, and the obtained solid was filtered. The obtained compound was washed by water and hexane, and dried in a vacuum oven at a temperature of 60° C. for a day to obtain about 6.3 g (5.8 mmol, yield of 71%) of Intermediate 1-3. The obtained compound was confirmed by LC-MS.

LC-MS m/z=1087(M+H)$^+$.

4) Synthesis of Intermediate 1-2

6.0 g (5.8 mmol) of Intermediate 1-4 was dissolved in 140 ml of dichloromethane, and 3.0 g (11.6 mmol) of silver trifluoromethanesulfonate and 48 ml of methanol were added thereto. The resultant was stirred in a dark at room temperature for about a day. When the reaction was complete, the resultant was filtered with diatomite, and washed with dichloromethane. The obtained organic material was distilled at a reduced pressure to obtain 7.5 g (10.4 mmol, yield of 90%) of Intermediate 1-2. The obtained compound was used in a successive reaction without confirming a structure of the obtained compound.

LC-MS m/z=Not detected.

5) Synthesis of Intermediate 1-1

5.0 g (29.9 mmol) of 1-chloro-5,6,7,8-tetrahydroisoquinoline was dissolved in 120 ml of tetrahydrofuran, and then 1.7 g (1.5 mmol) of tetrakistriphenylphosphine Pd(0) was added thereto at room temperature. The resultant was stirred for about 5 minutes. After that, 4.3 g (35.9 mmol) of phenylboronic acid and 8.3 g (59.8 mmol) of potassium carbonate were added thereto. Then, 60 ml of distilled water was added thereto and the resultant was heated at a temperature of 70° C. under reflux for a day. When the reaction was complete, 100 ml of ethyl acetate was added thereto.

The organic layer was dried by using magnesium sulfate and then distilled at a reduced pressure. The resultant obtained therefrom was purified by column chromatography to obtain about 5.5 g (26.3 mmol, yield of 88%) of Intermediate 1-1. The obtained compound was confirmed by LC-MS.

LC-MS m/z=210(M+H)$^+$.

6) Synthesis of Compound 1

At room temperature, 5.0 g (6.9 mmol) of Compound 1-2 was dissolved in 80 ml of ethanol. 1.7 g (8.3 mmol) of Compound 1-1 was added thereto and the resultant was refluxed at a heating temperature of 100° C. for 18 hours. After 18 hours, the resultant was cooled to room temperature. The obtained solid was filtered and washed with a small amount of methanol. The obtained solid compound was purified by column chromatography to obtain about 2.1 g (2.9 mmol, yield of 42%) of Compound 1. The obtained compound was confirmed by LC-MS and $^1$H NMR.

LC-MS m/z=718(M+H)$^+$.

$^1$H NMR (300 MHz, CDCl$_3$) δ=8.31-8.28 (m, 3H), 8.07 (br s, 1H), 7.85-7.41 (m, 7H), 7.01-6.97 (m, 3H), 3.36 (br s, 2H), 3.01 (br s, 2H), 1.84 (br s, 4H).

Synthesis Example 2

Synthesis of Compound 2

Compound 2 was synthesized according to Reaction Scheme 2:

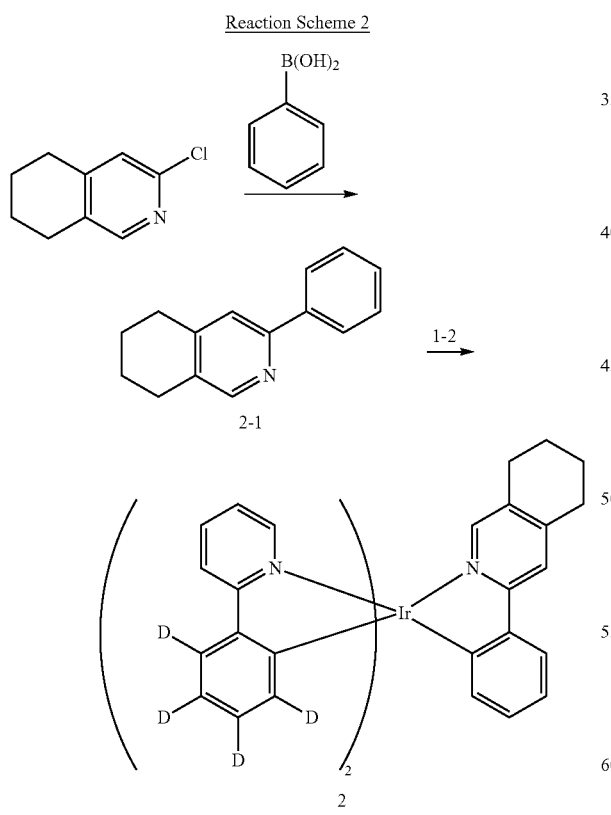

1) Synthesis of Intermediate 2-1

Intermediate 2-1 (yield of 80%) was synthesized in the same manner as Intermediate 1-1 in Synthesis Example 1, except that 3-chloro-5,6,7,8-tetrahydroisoquinoline was used instead of 1-chloro-5,6,7,8-tetrahydroisoquinoline. The obtained compound was confirmed by LC-MS.

LC-MS m/z=210(M+H)$^+$.

2) Synthesis of Compound 2

Compound 2 (yield of 38%) was synthesized in the same manner as Compound 1 in Synthesis Example 1, except that Intermediate 2-1 was used instead of Intermediate 1-1. The obtained compound was confirmed by LCMS and $^1$H NMR.

LC-MS m/z=718(M+H)$^+$.

$^1$H NMR (300 MHz, CDCl$_3$) δ=8.26-8.25 (m, 3H), 8.10 (d, 1H), 7.83-7.80 (m, 2H), 7.78 (s, 1H), 7.51-7.40 (m, 5H), 7.01 (br s, 2H), 3.42-3.40 (m, 2H), 2.62 (br s, 2H), 1.84-1.81 (m, 4H).

Synthesis Example 3

Synthesis of Compound 3

Compound 3 was synthesized according to Reaction Scheme 3:

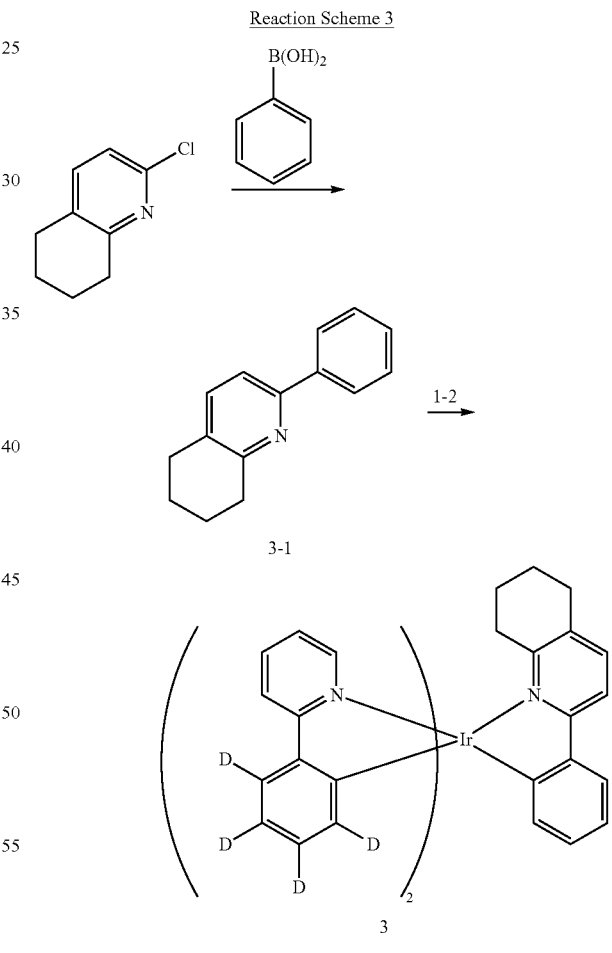

1) Synthesis of Intermediate 3-1

Intermediate 3-1 (yield of 82%) was synthesized in the same manner as Intermediate 1-1 in Synthesis Example 1, except that 2-chloro-5,6,7,8-tetrahydroquinoline was used instead of 1-chloro-5,6,7,8-tetrahydroisoquinoline. The obtained compound was confirmed by LC-MS.

LC-MS m/z=210(M+H)$^+$.

2) Synthesis of Compound 3

Compound 3 (yield of 17%) was synthesized in the same manner as Compound 1 in Synthesis Example 1, except that Intermediate 3-1 was used instead of Intermediate 1-1. The obtained compound was confirmed by LCMS and $^1$H NMR.

LC-MS m/z=718(M+H)$^+$.

$^1$H NMR (300 MHz, CDCl$_3$) δ=8.27 (d, 2H), 8.16 (d, 1H), 7.84 (br s, 2H), 7.60-7.38 (m, 6H), 7.24 (d, 1H), 7.02 (br s, 2H), 3.11-3.10 (m, 2H), 2.68 (br s, 2H), 1.83-1.80 (m, 4H).

Synthesis Example 4

Synthesis of Compound 4

Compound 4 was synthesized according to Reaction Scheme 4:

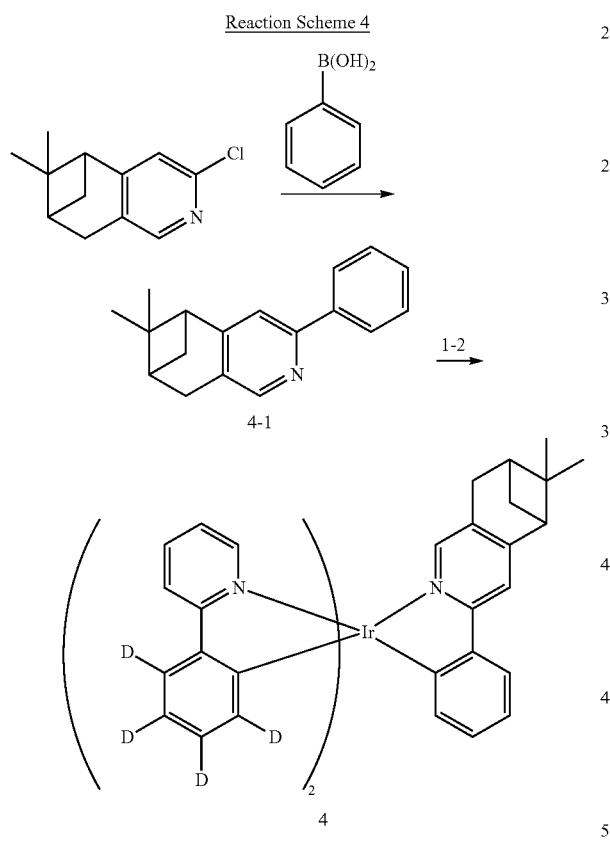

1) Synthesis of Intermediate 4-1

Intermediate 4-1 (yield of 80%) was synthesized in the same manner as Intermediate 1-1 in Synthesis Example 1, except that 3-chloro-6,6-dimethyl-5,6,7,8-tetrahydro-5,7-methanoisoquinoline (purchased at Pharma Costech, www.pctc.co.kr) was used instead of 1-chloro-5,6,7,8-tetrahydroisoquinoline. The obtained compound was confirmed by LC-MS.

LC-MS m/z=250(M+H)$^+$.

2) Synthesis of Compound 4

Compound 4 (yield of 35%) was synthesized in the same manner as Compound 1 in Synthesis Example 1, except that Intermediate 4-1 was used instead of Intermediate 1-1. The obtained compound was confirmed by LCMS and $^1$H NMR.

LC-MS m/z=758(M+H)$^+$.

$^1$H NMR (300 MHz, CDCl$_3$) δ=8.29 (br s, 3H), 8.13 (d, 1H), 7.85-7.83 (m, 3H), 7.55-7.36 (m, 5H), 7.01-7.00 (m, 2H), 2.84 (s, 1H), 2.36 (br s, 2H), 2.32 (br s, 1H), 1.86-1.84 (m, 2H), 0.91 (s, 6H).

Synthesis Example 5

Synthesis of Compound 5

Compound 5 was synthesized according to Reaction Scheme 5:

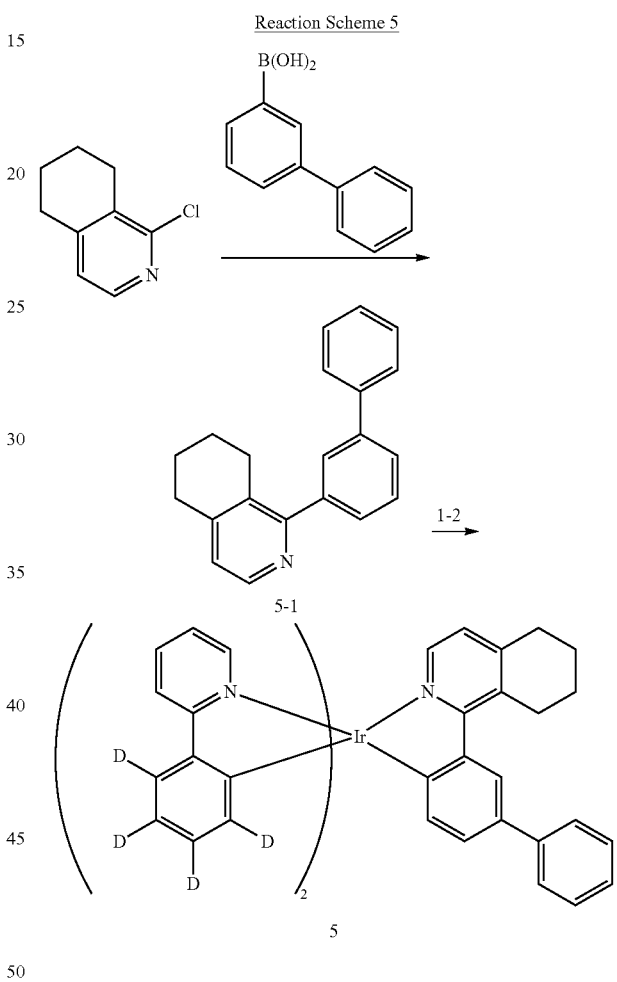

1) Synthesis of Intermediate 5-1

Intermediate 5-1 (yield of 73%) was synthesized in the same manner as Intermediate 1-1 in Synthesis Example 1, except that 3-biphenylboronic acid was used instead of phenylboronic acid. The obtained compound was confirmed by LC-MS.

LC-MS m/z=286(M+H)$^+$.

2) Synthesis of Compound 5

Compound 5 (yield of 35%) was synthesized in the same manner as Compound 1 in Synthesis Example 1, except that Intermediate 5-1 was used instead of Intermediate 1-1. The obtained compound was confirmed by LCMS and $^1$H NMR.

LC-MS m/z=794(M+H)$^+$.

$^1$H NMR (300 MHz, CDCl$_3$) δ=8.30-8.28 (m, 3H), 8.15 (s, 1H), 7.82-7.76 (m, 6H), 7.48-7.41 (m, 5H), 7.01-6.97 (m, 3H), 3.35 (br s, 2H), 2.99 (br s, 2H), 1.85-1.84 (m, 4H).

Synthesis Example 6

Synthesis of Compound 6

Compound 6 was synthesized according to Reaction Scheme 6:

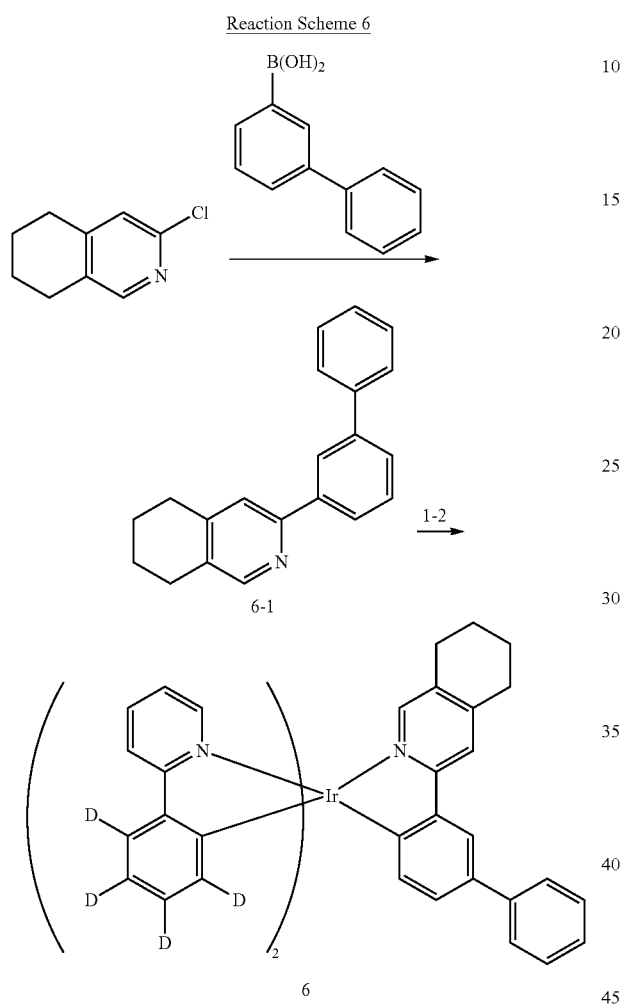

1) Synthesis of Intermediate 6-1

Intermediate 6-1 (yield of 80%) was synthesized in the same manner as Intermediate 1-1 in Synthesis Example 1, except that 3-biphenylboronic acid was used instead of phenylboronic acid. The obtained compound was confirmed by LC-MS.

LC-MS m/z=286(M+H)$^+$.

2) Synthesis of Compound 6

Compound 6 (yield of 30%) was synthesized in the same manner as Compound 1 in Synthesis Example 1, except that Intermediate 6-1 was used instead of Intermediate 1-1. The obtained compound was confirmed by LCMS and $^1$H NMR.

LC-MS m/z=794(M+H).

$^1$H NMR (300 MHz, CDCl$_3$) δ=8.28-8.26 (m, 3H), 8.42 (s, 1H), 7.87-7.71 (m, 7H), 7.52-7.36 (m, 5H), 7.02 (br s, 2H), 3.41 (br s, 2H), 2.64 (br s, 2H), 1.85 (br s, 4H).

Synthesis Example 7

Synthesis of Compound 7

Compound 7 was synthesized according to Reaction Scheme 7:

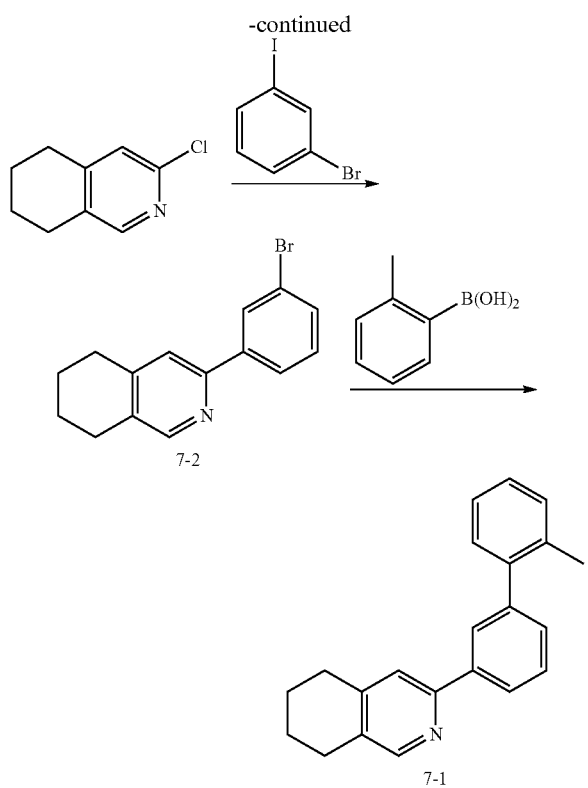

1) Synthesis of Intermediate 7-5

Intermediate 7-5 (yield of 86%) was synthesized in the same manner as Intermediate 1-4 in Synthesis Example 1, except that 2-bromo-5-methylpyridine was used instead of 2-bromopyridine. The obtained compound was confirmed by LC-MS.

LC-MS m/z=175(M+H)$^+$.

2) Synthesis of Intermediate 7-4

Intermediate 7-4 (yield of 75%) was synthesized in the same manner as Intermediate 1-3 in Synthesis Example 1, except that Intermediate 7-15 was used instead of Intermediate 1-4. The obtained compound was confirmed by LC-MS.

LC-MS m/z=1143(M+H)$^+$.

3) Synthesis of Intermediate 7-3

Intermediate 7-3 (yield of ~99%) was synthesized in the same manner as Intermediate 1-2 in Synthesis Example 1, except that Intermediate 7-4 was used instead of Intermediate 1-3. The obtained compound was used in a successive reaction without confirming a structure of the obtained compound.

LC-MS m/z=Not detected.

4) Synthesis of Intermediate 7-2

7.0 g (41.8 mmol) of 3-chloro-5,6,7,8-tetrahydroisoquinoline was dissolved in 200 ml of tetrahydrofuran, and then 2.4 g (2.1 mmol) of tetrakistriphenylphosphine Pd(0) was added thereto at room temperature and the resultant was stirred for about 5 minutes. After that, 5.3 ml (41.8 mmol) of 1-bromo-2-iodobenzene and 11.6 g (83.6 mmol) of potassium carbonate were added thereto. Then, 100 ml of distilled water was added thereto and the resultant was refluxed while heating at a temperature of 70° C. for a day. When the reaction was complete, 150 ml of ethyl acetate was added to perform an extraction process, and the extracted organic layer was dried by using magnesium sulfate and then distilled at a reduced pressure. The resultant obtained therefrom was purified by column chromatography to obtain about 7.0 g (24.3 mmol, yield of 58%) of Intermediate 7-2. The obtained compound was confirmed by LC-MS.

LC-MS m/z=288(M+H)$^+$.

5) Synthesis of Intermediate 7-1

7.0 g (24.3 mmol) of Intermediate 7-2 was dissolved in 150 ml of ethanol. 1.4 g (1.2 mmol) of tetrakistriphenylphosphine Pd(0) was added thereto at room temperature and the resultant was stirred for about 5 minutes. After that, 5.0 g (36.5 mmol) of 2-methylphenylboronic acid and 10.0 g (72.9 mmol) of potassium carbonate were added and the resultant was refluxed while heating at a temperature of 75° C. for a day. When the reaction was complete, the resultant was concentrated at a reduced pressure. 200 ml of ethyl acetate and 80 ml of brine were added to extract the product. The extracted organic layer was dried by using magnesium sulfate and distilled at a reduced pressure. The resultant obtained therefrom was purified by column chromatography to obtain about 6.4 g (21.4 mmol, yield of 88%) of Intermediate 7-1. The obtained compound was confirmed by LC-MS.

LC-MS m/z=300(M+H)$^+$.

6) Synthesis of Compound 7

Compound 7 (yield of 18%) was synthesized in the same manner as Compound 1 in Synthesis Example 1, except that Intermediate 7-1 was used instead of Intermediate 1-1, and Intermediate 7-3 was used instead of Intermediate 1-2. The obtained compound was confirmed by LCMS and $^1$H NMR.

LC-MS m/z=836(M+H)$^+$.

$^1$H NMR (300 MHz, CDCl$_3$) δ=8.34 (d, 2H), 8.33 (br s, 1H), 7.96-65 (m, 6H), 7.42-7.24 (m, 5H), 3.41 (br s, 2H), 2.65-6.62 (m, 2H), 2.19 (s, 6H), 1.86-1.82 (m, 4H).

Synthesis Example 8

Synthesis of Compound 8

Compound 8 was synthesized according to Reaction Scheme 8:

Reaction Scheme 8

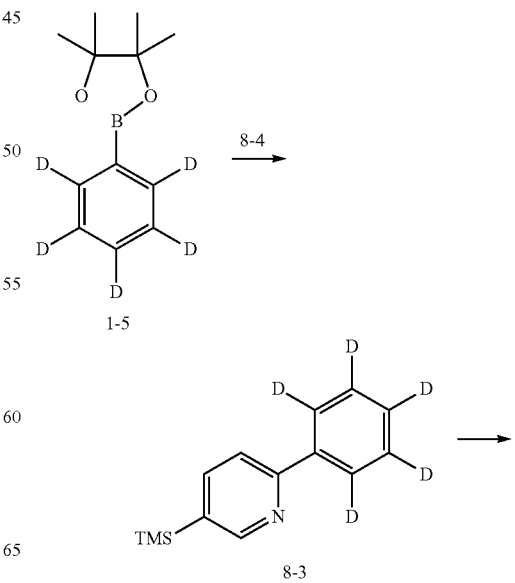

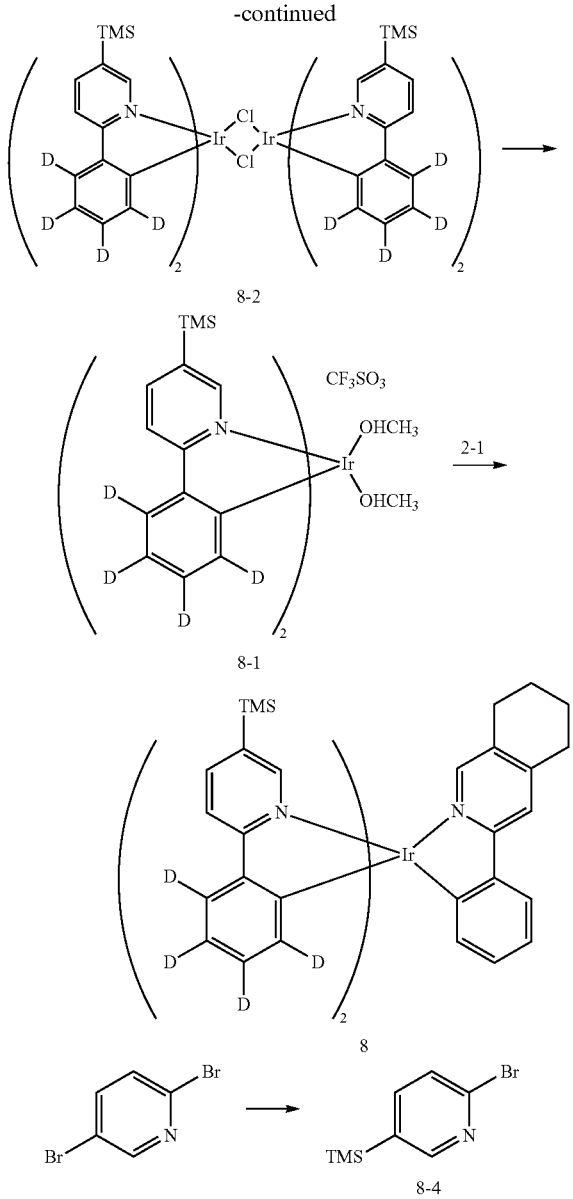

2) Synthesis of Intermediate 8-3

Intermediate 8-3 (yield of 77%) was synthesized in the same manner as Intermediate 7-5 in Synthesis Example 7, except that Intermediate 8-4 was used instead of 2-bromo-5-methylpyridine. The obtained compound was confirmed by LC-MS LC-MS m/z=233(M+H)$^+$.

3) Synthesis of Intermediate 8-2

Intermediate 8-2 (yield of 70%) was synthesized in the same manner as Intermediate 1-3 in Synthesis Example 1, except that Intermediate 8-3 was used instead of Intermediate 1-4. The obtained compound was confirmed by LC-MS.

LC-MS m/z=1375(M+H)$^+$.

4) Synthesis of Intermediate 8-1

Intermediate 8-1 (yield of ~99%) was synthesized in the same manner as Intermediate 1-2 in Synthesis Example 1, except that Intermediate 8-2 was used instead of Intermediate 1-3. The obtained compound was used in a successive reaction without confirming a structure thereof.

LC-MS m/z=Not detected.

5) Synthesis of Compound 8

Compound 8 (yield of 25%) was synthesized in the same manner as Compound 2 in Synthesis Example 2, except that Intermediate 8-1 was used instead of Intermediate 1-2. The obtained compound was confirmed by LCMS and $^1$H NMR.

LC-MS m/z=862(M+H)$^+$.

$^1$H NMR (300 MHz, CDCl$_3$) δ=8.53 (br s, 2H), 8.14 (s, 1H), 8.03 (br s, 1H), 7.80-7.75 (m, 3H), 7.72-7.70 (m, 2H), 7.51-7.42 (m, 3H), 3.43-3.41 (m, 2H), 2.64-2.61 (m, 2H), 1.85-1.81 (m, 4H), 0.29 (s, 9H).

Synthesis Example 9

Synthesis of Compound 9

Compound 9 was synthesized according to Reaction Scheme 9:

Reaction Scheme 9

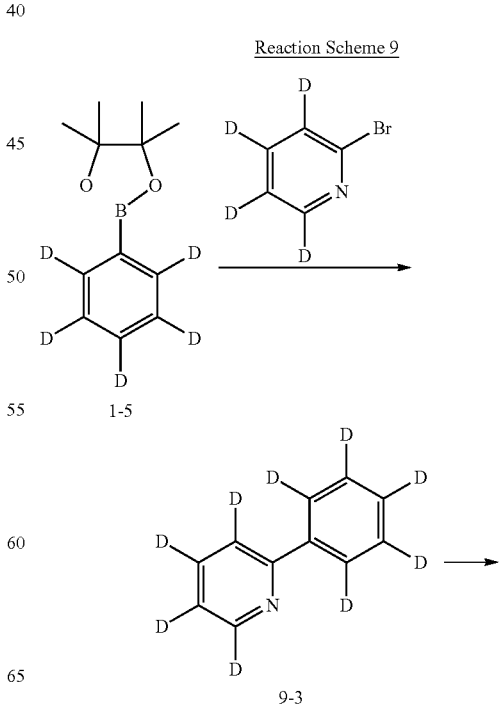

1) Synthesis of Intermediate 8-4

20.0 g (84.4 mmol) of 2,5-dibromopyridine was dissolved in 300 ml of diethyl ether. 53.0 ml (84.4 mmol) of 1.6 M n-BuLi (in hexane) was slowly added thereto at a temperature of −78° C., and the resultant was stirred for about 1 hour. After that, 11 ml (84.4 mmol) of chlorotrimethylsilane was added thereto for 50 minutes and the resultant was stirred at a temperature of −78° C. for about 1 hour. Then, the resultant was stirred at room temperature for about 18 hours. When the reaction was complete, 100 ml of water was added thereto at room temperature, and then 400 ml of ethyl acetate and 500 ml of brine were added to extract the product. The organic layer extracted therefrom was dried by using magnesium sulfate and distilled at a reduced pressure. The resultant obtained therefrom was purified by column chromatography to obtain about 16.0 g (69.5 mmol, yield of 82%) of Intermediate 8-4. The obtained compound was confirmed by LC-MS.

LC-MS m/z=230(M+H)$^+$.

$^1$H NMR (300 MHz, CDCl$_3$) δ=8.40 (s, 1H), 7.61 (d, 1H), 7.45 (d, 1H), 0.29 (s, 9H).

LC-MS m/z=726(M+H)$^+$.

$^1$H NMR (300 MHz, CDCl$_3$) δ=8.55 (s, 2H), 8.12 (d, 1H), 7.80 (s, 1H), 7.61-7.48 (m, 3H), 3.44 (br s, 2H), 2.66 (br s, 2H), 1.86-1.82 (m, 4H).

Synthesis Example 10

Synthesis of Compound 10

Compound 10 was synthesized according to Reaction Scheme 10:

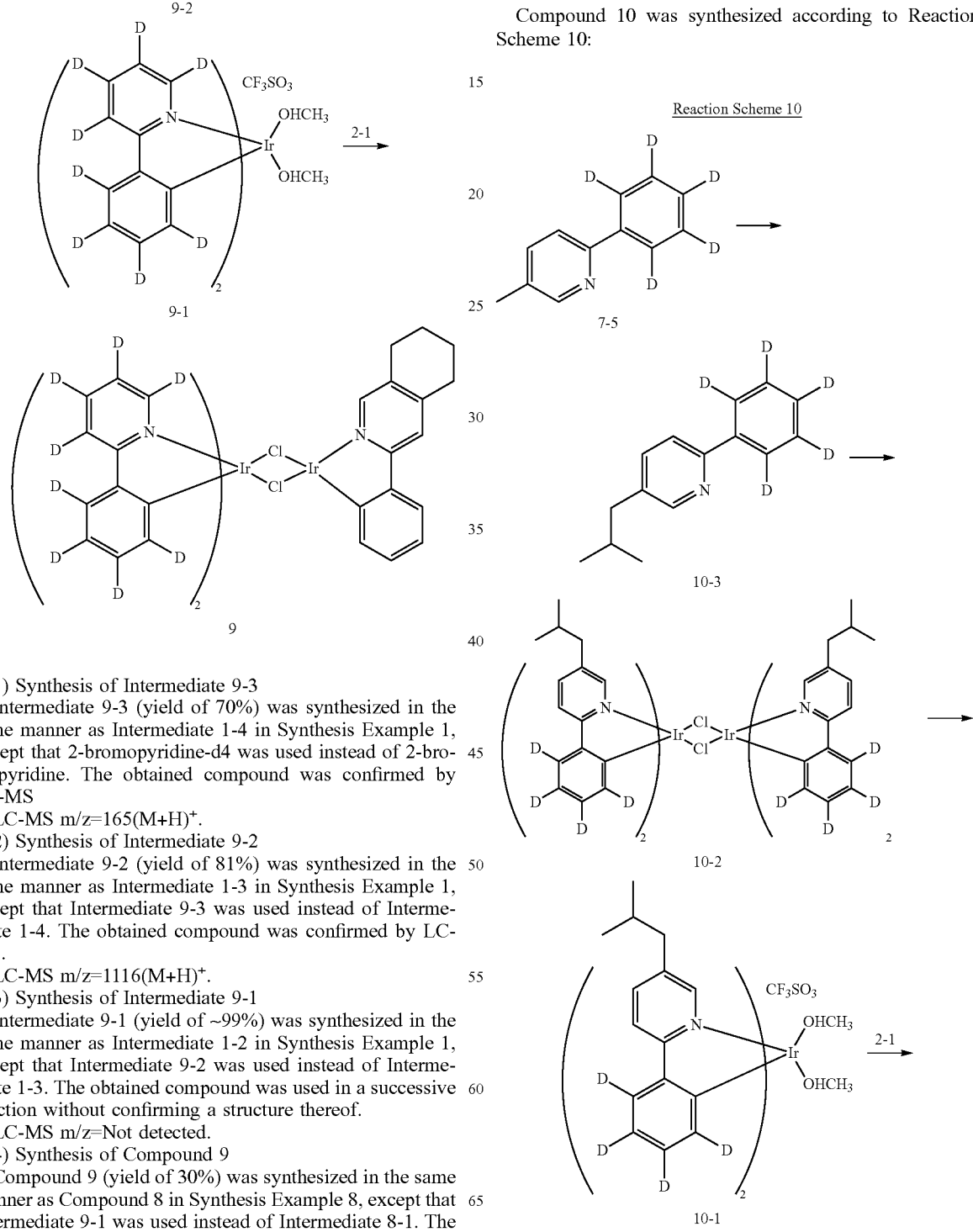

1) Synthesis of Intermediate 9-3

Intermediate 9-3 (yield of 70%) was synthesized in the same manner as Intermediate 1-4 in Synthesis Example 1, except that 2-bromopyridine-d4 was used instead of 2-bromopyridine. The obtained compound was confirmed by LC-MS LC-MS m/z=165(M+H)$^+$.

2) Synthesis of Intermediate 9-2

Intermediate 9-2 (yield of 81%) was synthesized in the same manner as Intermediate 1-3 in Synthesis Example 1, except that Intermediate 9-3 was used instead of Intermediate 1-4. The obtained compound was confirmed by LC-MS.

LC-MS m/z=1116(M+H)$^+$.

3) Synthesis of Intermediate 9-1

Intermediate 9-1 (yield of ~99%) was synthesized in the same manner as Intermediate 1-2 in Synthesis Example 1, except that Intermediate 9-2 was used instead of Intermediate 1-3. The obtained compound was used in a successive reaction without confirming a structure thereof.

LC-MS m/z=Not detected.

4) Synthesis of Compound 9

Compound 9 (yield of 30%) was synthesized in the same manner as Compound 8 in Synthesis Example 8, except that Intermediate 9-1 was used instead of Intermediate 8-1. The obtained compound was confirmed by LCMS and $^1$H NMR.

111
-continued

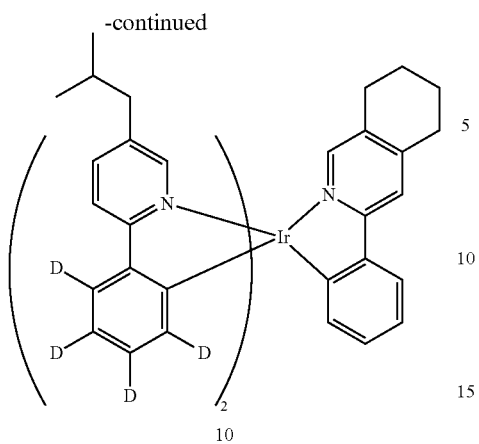

10

1) Synthesis of Intermediate 10-3

4.2 g (23.9 mmol) of Intermediate 7-5 was dissolved in 400 ml of tetrahydrofuran. 18.0 ml (35.9 mmol) of 2.0 M lithium diisopropylamide solution was slowly added thereto at a temperature of −78° C. and the result was stirred for about 1 hour. After that, 3.6 ml (38.2 mmol) of 2-bromopropane was added, the resultant was stirred at a temperature of −78° C. for about 1 hour and further stirred at room temperature for about 18 hours. When the reaction was complete, 100 ml of water was added thereto at room temperature, and 200 ml of dichloromethane and 50 ml of brine were added to extract the product. The extracted organic layer was dried by using magnesium sulfate and distilled at a reduced pressure. The resultant obtained therefrom was purified by column chromatography to obtain about 4.0 g (18.5 mmol, yield of 77%) of Intermediate 10-3. The obtained compound was confirmed by LC-MS.

LC-MS m/z=217(M+H)$^+$.

2) Synthesis of Intermediate 10-2

Intermediate 10-2 (yield of 75%) was synthesized in the same manner as Intermediate 1-3 in Synthesis Example 1, except that Intermediate 10-3 was used instead of Intermediate 1-4. The obtained compound was confirmed by LC-MS.

LC-MS m/z=1311(M+H)$^+$.

3) Synthesis of Intermediate 10-1

Intermediate 10-1 (yield of ~99%) was synthesized in the same manner as Intermediate 1-2 in Synthesis Example 1, except that Intermediate 10-2 was used instead of Intermediate 1-3. The obtained compound was used in a successive reaction without confirming a structure thereof.

LC-MS m/z=Not detected.

4) Synthesis of Compound 10

Compound 10 (yield of 28%) was synthesized in the same manner as Compound 8 in Synthesis Example 8, except that Intermediate 10-1 was used instead of Intermediate 8-1. The obtained compound was confirmed by LCMS and $^1$H NMR.

LC-MS m/z=830(M+H)$^+$.

$^1$H NMR (300 MHz, CDCl$_3$) δ=8.58 (d, 2H), 8.14 (br s, 1H), 7.77-7.72 (m, 3H), 7.55-7.38 (m, 4H), 3.43 (br s, 2H), 2.64 (br s, 2H), 2.54 (d, 4H), 1.86-1.80 (m, 6H), 0.88 (s, 12H).

112

Synthesis Example 11

Synthesis of Compound 11

Compound 11 was synthesized according to Reaction Scheme 11:

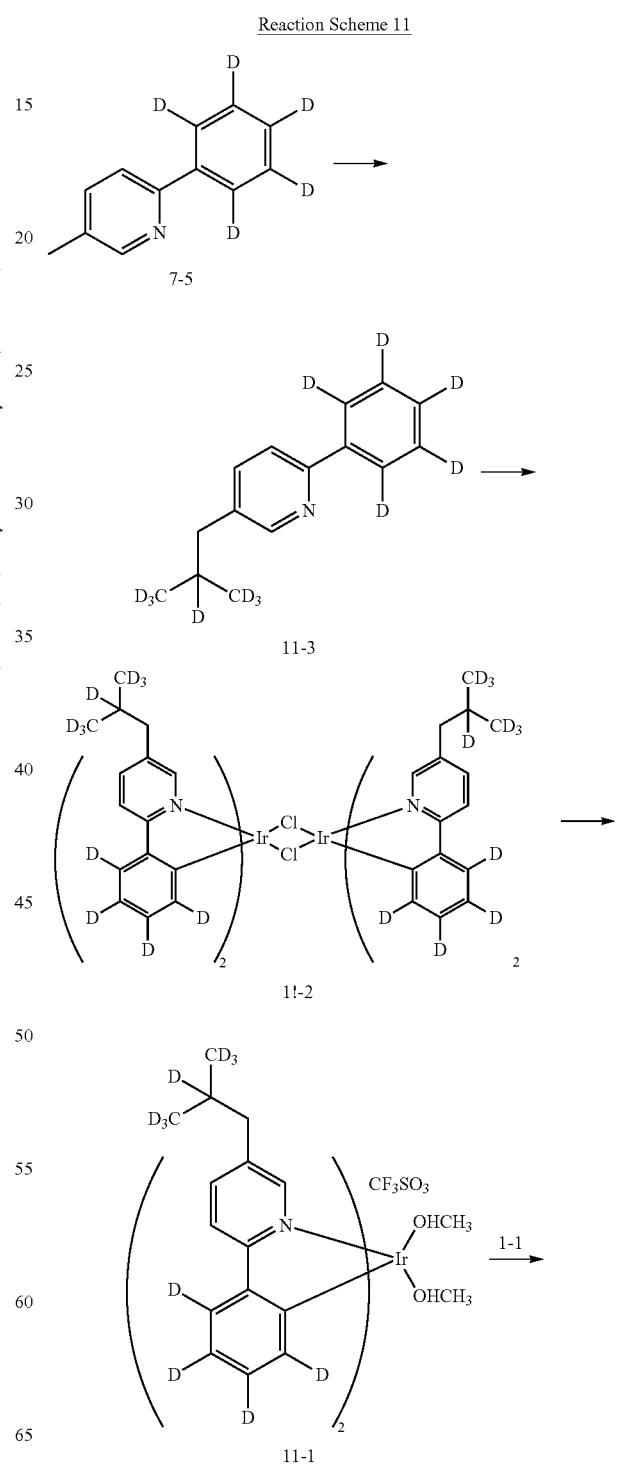

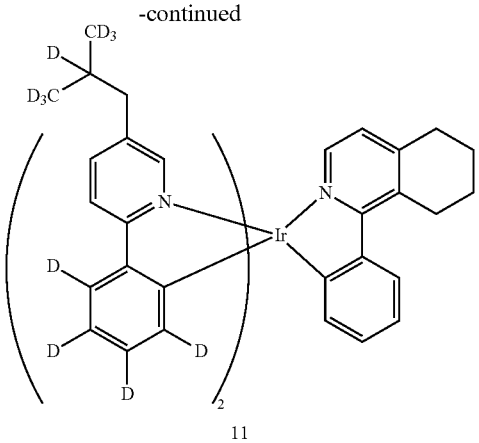

11

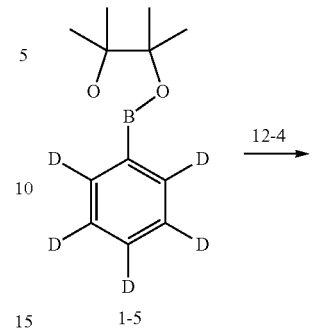

Reaction Scheme 12

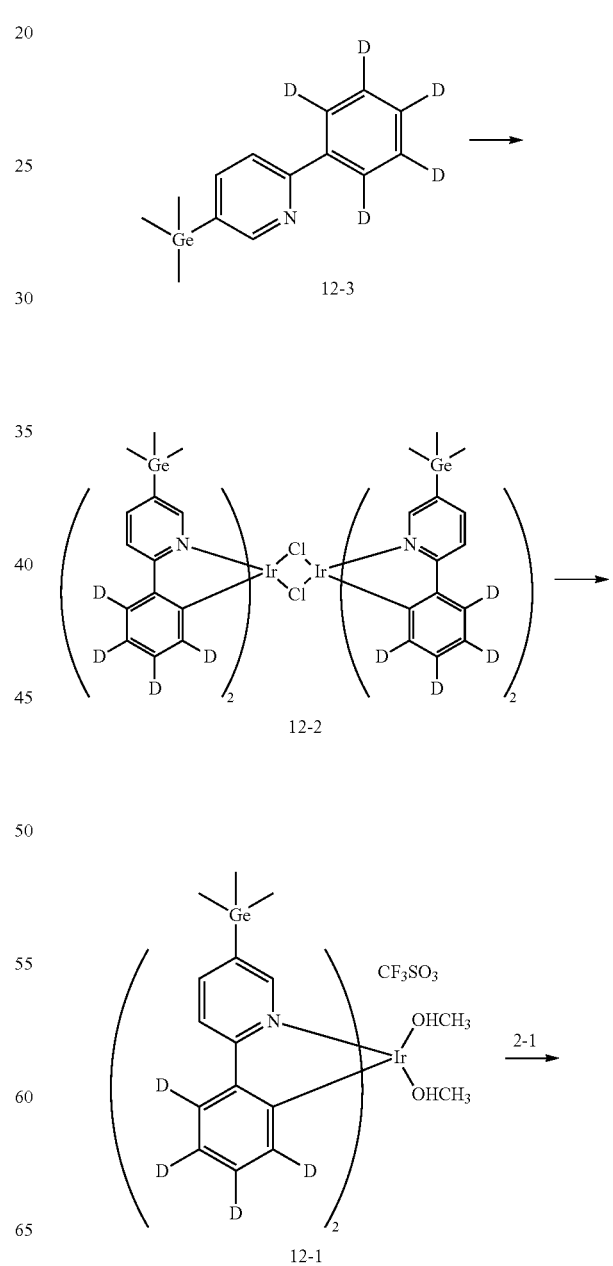

1) Synthesis of Intermediate 11-3

Intermediate 11-3 (yield of 53%) was synthesized in the same manner as Intermediate 10-3 in Synthesis Example 10, except that 2-iodopropane-d7 was used instead of 2-bromopropane. The obtained compound was confirmed by LC-MS.

LC-MS m/z=224(M+H)$^+$.

2) Synthesis of Intermediate 11-2

Intermediate 11-2 (yield of 60%) was synthesized in the same manner as Intermediate 1-3 in Synthesis Example 1, except that Intermediate 11-3 was used instead of Intermediate 1-4. The obtained compound was confirmed by LC-MS.

LC-MS m/z=1340(M+H)$^+$.

3) Synthesis of Intermediate 11-1

Intermediate 11-1 (yield of ~99%) was synthesized in the same manner as Intermediate 1-2 in Synthesis Example 1, except that Intermediate 11-2 was used instead of Intermediate 1-3. The obtained compound was used in a successive reaction without confirming a structure thereof.

LC-MS m/z=Not detected.

4) Synthesis of Compound 11

Compound 11 (yield of 14%) was synthesized in the same manner as Compound 1 in Synthesis Example 1, except that Intermediate 11-1 was used instead of Intermediate 1-2. The obtained compound was confirmed by LCMS and $^1$H NMR.

LC-MS m/z=844(M+H)$^+$.

$^1$H NMR (300 MHz, CDCl$_3$) δ=8.52-8.50 (m, 3H), 8.17 (br s, 1H), 7.76 (d, 2H), 7.55-7.35 (m, 5H), 7.01 (d, 1H), 3.42 (br s, 2H), 2.97 (br s, 2H), 2.30-2.27 (m, 4H), 1.88-1.85 (m, 4H).

Synthesis Example 12

Synthesis of Compound 12

Compound 12 was synthesized according to Reaction Scheme 12:

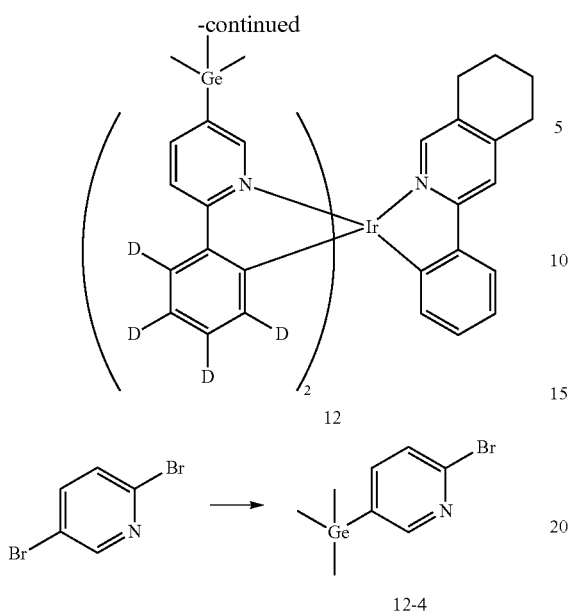

1) Synthesis of Intermediate 12-4

Intermediate 12-4 (yield of 50%) was synthesized in the same manner as Intermediate 8-4 in Synthesis Example 8, except that chlorotrimethylgermane was used instead of chlorotrimethylsilane. The obtained compound was confirmed by LC-MS.

LC-MS m/z=276(M+H)$^+$.

2) Synthesis of Intermediate 12-3

Intermediate 12-3 (yield of 75%) was synthesized in the same manner as Intermediate 8-3 in Synthesis Example 8, except that Intermediate 12-4 was used instead of Intermediate 8-4. The obtained compound was confirmed by LC-MS.

LC-MS m/z=279(M+H)$^+$.

3) Synthesis of Intermediate 12-2

Intermediate 12-2 (yield of 70%) was synthesized in the same manner as Intermediate 1-3 in Synthesis Example 1, except that Intermediate 12-3 was used instead of Intermediate 1-4. The obtained compound was used in a successive reaction without confirming a structure thereof.

LC-MS m/z=Not detected.

4) Synthesis of Intermediate 12-1

Intermediate 12-1 (yield of ~99%) was synthesized in the same manner as Intermediate 1-2 in Synthesis Example 1, except that Intermediate 12-2 was used instead of Intermediate 1-3. The obtained compound was used in a successive reaction without confirming a structure thereof.

LC-MS m/z=Not detected.

5) Synthesis of Compound 12

Compound 12 (yield of 20%) was synthesized in the same manner as Compound 2 in Synthesis Example 2, except that Intermediate 12-1 was used instead of Intermediate 1-2. The obtained compound was confirmed by LCMS and $^1$H NMR.

LC-MS m/z=952(M+H)$^+$.

$^1$H NMR (300 MHz, CDCl$_3$) δ=8.52 (br s, 1H), 8.33 (s, 2H), 8.14 (br s, 1H), 7.98 (br s, 2H), 7.73 (s, 1H), 7.55-7.33 (m, 5H), 3.46-3.43 (m, 2H), 2.66-2.63 (m, 2H), 1.84-1.81 (m, 4H), 0.36 (s, 18H).

Synthesis Example 13

Synthesis of Compound 12

Compound 13 was synthesized according to Reaction Scheme 13:

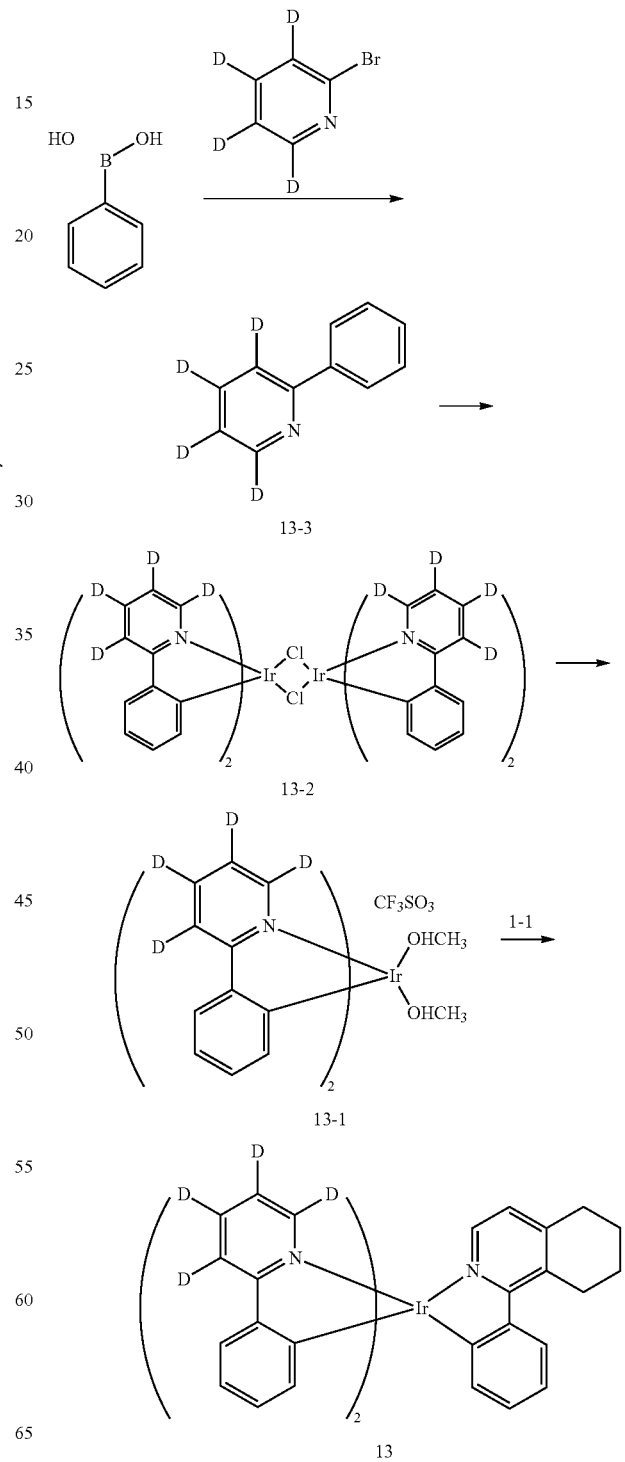

1) Synthesis of Intermediate 13-3

5.0 g (41.0 mmol) of phenylboronic acid was dissolved in 300 ml of ethanol, and then 2.3 g (2.1 mmol) of tetrakistriphenylphosphine Pd(0) was added thereto at room temperature and the resultant was stirred for 5 minutes. After that, 6.0 g (37.0 mmol) of 2-bromopyridine-d4 and 15.0 g (111.0 mmol) of potassium carbonate were added, and the resultant was refluxed at a heating temperature of 80° C. for a day. When the reaction was complete, the resultant was concentrated at a reduced pressure, and then 200 ml of dichloromethane and 80 ml of brine were added thereto to extract the product. The extracted organic layer was dried by using magnesium sulfate and distilled at a reduced pressure. The resultant obtained therefrom was purified by column chromatography to obtain about 4.7 g (29.6 mmol, yield of 80%) of Intermediate 13-3. The obtained compound was confirmed by LC-MS.

LC-MS m/z=160(M+H)$^+$.

2) Synthesis of Intermediate 13-2

Intermediate 13-2 (yield of 80%) was synthesized in the same manner as Intermediate 1-3 in Synthesis Example 1, except that Intermediate 13-3 was used instead of Intermediate 1-4. The obtained compound was confirmed by LC-MS.

LC-MS m/z=1087(M+H)$^+$.

3) Synthesis of Intermediate 13-1

Intermediate 13-1 (yield of ~99%) was synthesized in the same manner as Intermediate 1-2 in Synthesis Example 1, except that Intermediate 13-2 was used instead of Intermediate 1-3. The obtained compound was used in a successive reaction without confirming a structure thereof.

LC-MS m/z=Not detected.

4) Synthesis of Compound 13

Compound 13 (yield of 24%) was synthesized in the same manner as Compound 1 in Synthesis Example 1, except that Intermediate 13-1 was used instead of Intermediate 1-2. The obtained compound was confirmed by LCMS and $^1$H NMR.

LC-MS m/z=718(M+H)$^+$.

$^1$H NMR (300 MHz, CDCl$_3$) δ=8.33 (d, 1H), 8.20 (d, 2H), 7.63-7.45 (m, 9H), 7.02 (d, 2H), 3.45 (br s, 2H), 2.98 (br s, 2H), 1.86-1.83 (m, 4H).

Synthesis Example 14

Synthesis of Compound 14

Compound 14 was synthesized according to Reaction Scheme 14:

Reaction Scheme 14

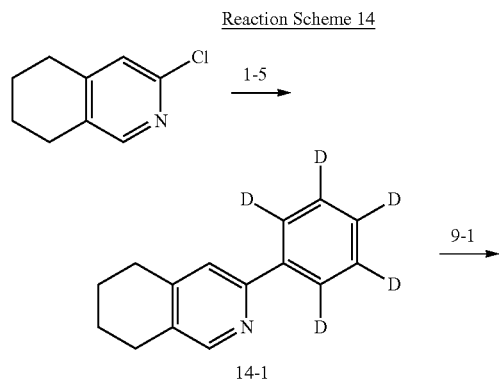

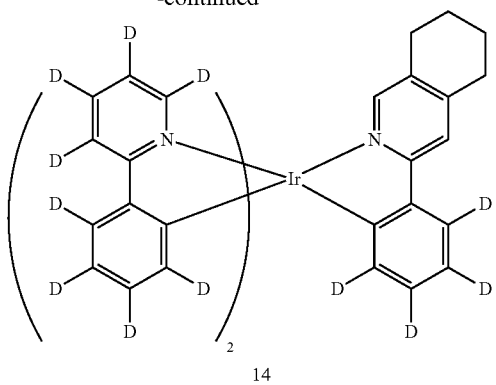

1) Synthesis of Intermediate 14-1

Intermediate 14-1 (yield of 85%) was synthesized in the same manner as Intermediate 2-1 in Synthesis Example 2, except that Intermediate 1-5 was used instead of phenylboronic acid. The obtained compound was confirmed by LC-MS.

LC-MS m/z=215(M+H).

2) Synthesis of Compound 14

Compound 14 (yield of 15%) was synthesized in the same manner as Compound 1 in Synthesis Example 1, except that Intermediate 9-1 was used instead of Intermediate 1-2, and Intermediate 14-1 was used instead of Intermediate 1-1. The obtained compound was confirmed by LCMS and $^1$H NMR.

LC-MS m/z=730(M+H)$^+$.

$^1$H NMR (300 MHz, CDCl$_3$) δ=8.36 (s, 1H), 7.63 (s, 9H), 3.44 (br s, 2H), 2.65 (br s, 2H), 1.85-1.82 (m, 4H).

Synthesis Example 15

Synthesis of Compound 15

Compound 15 was synthesized according to Reaction Scheme 15:

Reaction Scheme 15

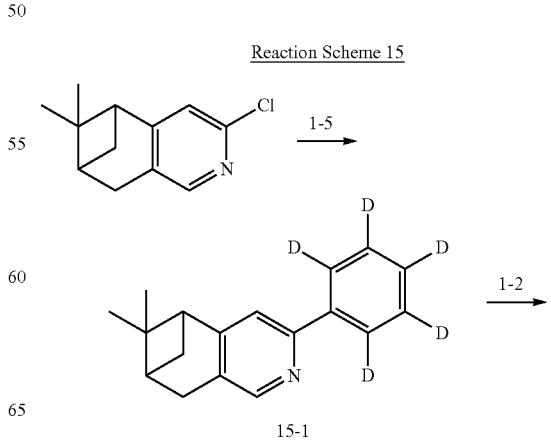

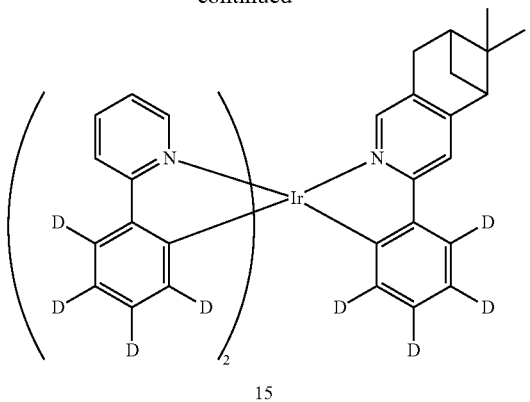

15

1) Synthesis of Intermediate 15-1

Intermediate 15-1 (yield of 80%) was synthesized in the same manner as Intermediate 4-1 in Synthesis Example 47, except that Intermediate 1-5 was used instead of phenylboronic acid. The obtained compound was confirmed by LC-MS.

LC-MS m/z=255(M+H)$^+$.

2) Synthesis of Compound 15

Compound 15 (yield of 13%) was synthesized in the same manner as Compound 1 in Synthesis Example 1, except that Intermediate 15-1 was used instead of Intermediate 1-1. The obtained compound was confirmed by LCMS and $^1$H NMR.

LC-MS m/z=762(M+H)$^+$.

$^1$H NMR (300 MHz, CDCl$_3$) δ=8.31 (br s, 3H), 7.86-7.82 (m, 3H), 7.32-7.24 (m, 2H), 7.01-7.00 (m, 2H), 2.84 (s, 1H), 2.36 (br s, 2H), 2.33-2.31 (m, 1H), 1.86-1.84 (m, 2H), 0.90 (s, 6H).

Synthesis Example 16

Synthesis of Compound 16

Compound 16 was synthesized according to Reaction Scheme 16:

Reaction Scheme 16

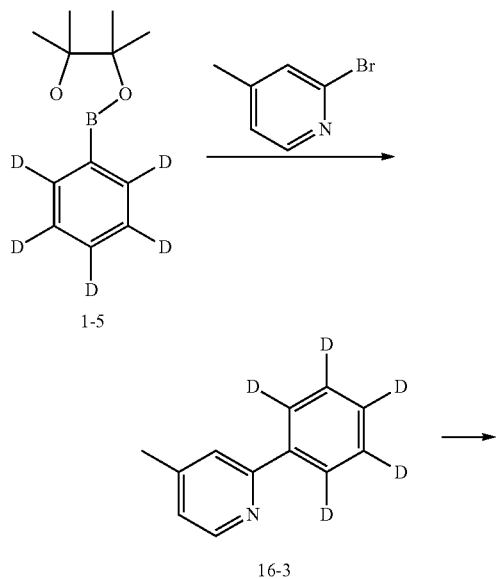

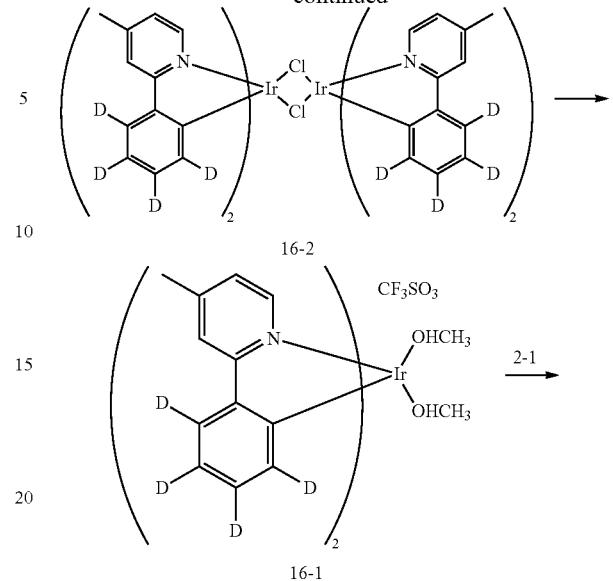

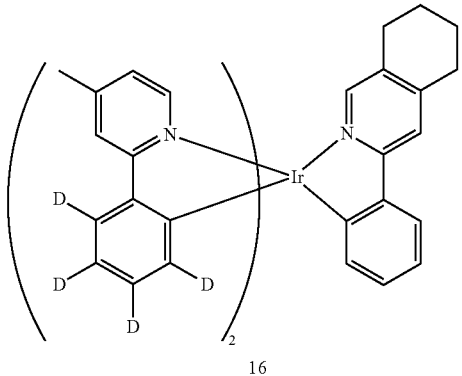

16

1) Synthesis of Intermediate 16-3

Intermediate 16-3 (yield of 72%) was synthesized in the same manner as Intermediate 12-3 in Synthesis Example 12, except that Intermediate 12-4 was used instead of 2-bromo-4-methylpyridine. The obtained compound was confirmed by LC-MS.

LC-MS m/z=175(M+H)$^+$.

2) Synthesis of Intermediate 16-2

Intermediate 16-2 (yield of 55%) was synthesized in the same manner as Intermediate 1-3 in Synthesis Example 1, except that Intermediate 16-3 was used instead of Intermediate 1-4. The obtained compound was used in a successive reaction without confirming a structure thereof.

LC-MS m/z=Not detected

3) Synthesis of Intermediate 16-1

Intermediate 16-1 (yield of ~99%) was synthesized in the same manner as Intermediate 1-2 in Synthesis Example 1, except that Intermediate 16-2 was used instead of Intermediate 1-3. The obtained compound was used in a successive reaction without confirming a structure thereof.

LC-MS m/z=Not detected.

4) Synthesis of Compound 16

Compound 16 (yield of 25%) was synthesized in the same manner as Compound 1 in Synthesis Example 1, except that Intermediate 2-1 was used instead of Intermediate 1-1, and Intermediate 16-1 was used instead of Intermediate 1-2. The obtained compound was confirmed by LCMS and $^1$H NMR.

LC-MS m/z=746(M+H)$^+$.

$^1$H NMR (300 MHz, CDCl$_3$) δ=8.47 (d, 2H), 8.25 (d, 1H), 7.92 (s, 2H), 7.85 (s, 1H), 7.66-7.48 (m, 3H), 7.06 (d, 2H), 3.44-3.41 (m, 2H), 2.63 (br s, 2H), 2.31 (s, 6H), 1.84-1.81 (m, 4H).

Synthesis Example 17

Synthesis of Compound 17

Compound 17 was synthesized according to Reaction Scheme 17.

Reaction Scheme 17

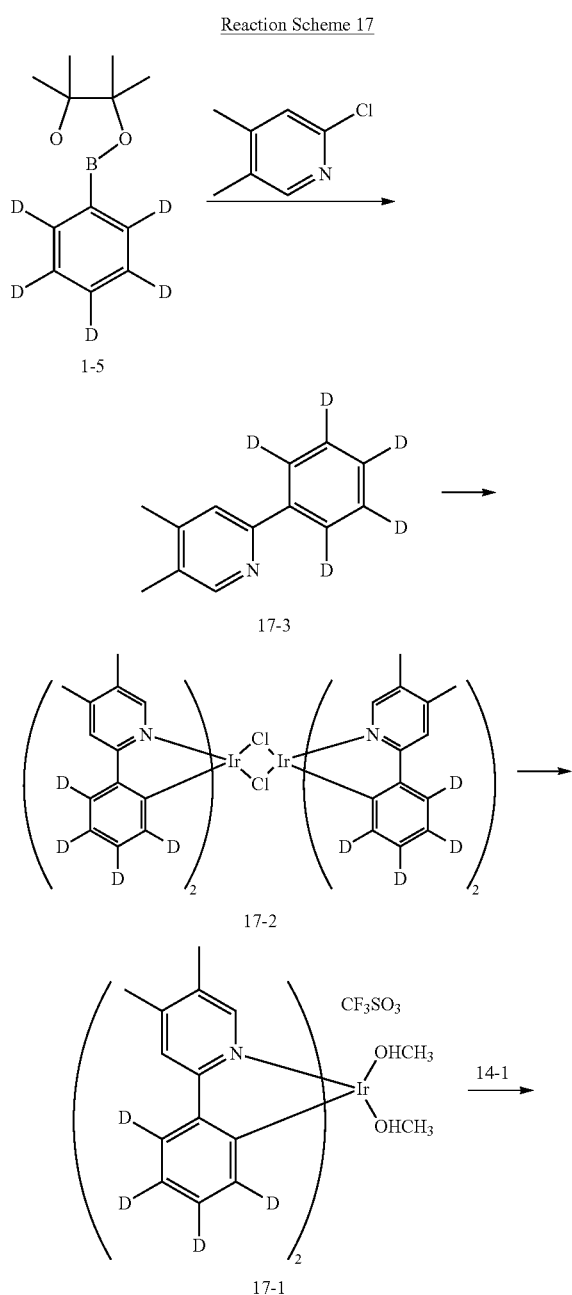

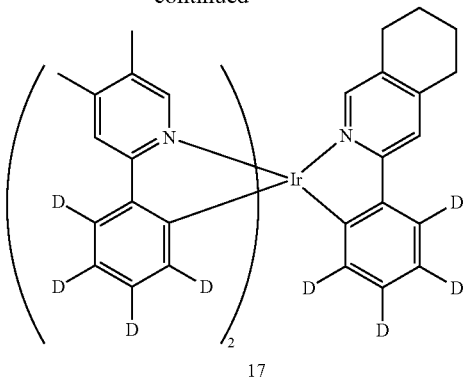

1) Synthesis of Intermediate 17-3

Intermediate 17-3 (yield of 68%) was synthesized in the same manner as Intermediate 16-3 in Synthesis Example 16, except that 2-chloro-4,5-dimethylpyridine was used instead of Intermediate 2-bromo-4-methylpyridine. The obtained compound was confirmed by LC-MS.

LC-MS m/z=189(M+H)$^+$.

2) Synthesis of Intermediate 17-2

Intermediate 17-2 (yield of 32%) was synthesized in the same manner as Intermediate 1-3 in Synthesis Example 1, except that Intermediate 17-3 was used instead of Intermediate 1-4. The obtained compound was used in a successive reaction without confirming a structure thereof.

LC-MS m/z=Not detected

3) Synthesis of Intermediate 17-1

Intermediate 17-1 (yield of ~99%) was synthesized in the same manner as Intermediate 1-2 in Synthesis Example 1, except that Intermediate 17-2 was used instead of Intermediate 1-3. The obtained compound was used in a successive reaction without confirming a structure the obtained compound.

LC-MS m/z=Not detected.

4) Synthesis of Compound 17

Compound 17 (yield of 15%) was synthesized in the same manner as Compound 1 in Synthesis Example 1, except that Intermediate 14-1 was used instead of Intermediate 1-1, and Intermediate 17-1 was used instead of Intermediate 1-2. The obtained compound was confirmed by LCMS and $^1$H NMR.

LC-MS m/z=778(M+H)$^+$.

$^1$H NMR (300 MHz, CDCl$_3$) δ=8.52 (s, 2H), 7.68 (s, 2H), 3.43-3.41 (m, 2H), 2.65 (br s, 2H), 2.37 (s, 12H), 1.86-1.82 (m, 4H).

Synthesis Example 18

Synthesis of Compound 18

Compound 18 was synthesized according to Reaction Scheme 18:

Reaction Scheme 18

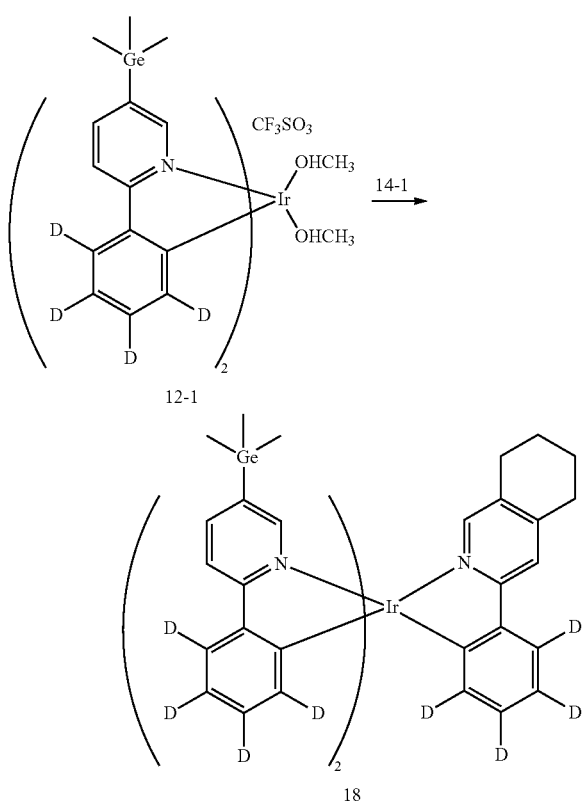

1) Synthesis of Compound 18

Compound 18 (yield of 32%) was synthesized in the same manner as Compound 1 in Synthesis Example 1, except that Intermediate 14-1 was used instead of Intermediate 1-1, and Intermediate 12-1 was used instead of Intermediate 1-2. The obtained compound was confirmed by LCMS and $^1$H NMR.

LC-MS m/z=956(M+H)$^+$.

$^1$H NMR (300 MHz, CDCl$_3$) δ=8.52 (br s, 1H), 8.33 (s, 2H), 7.97 (br s, 2H), 7.73 (s, 1H), 7.33 (d, 2H), 3.45-3.43 (m, 2H), 2.64 (br s, 2H), 1.84-1.80 (m, 4H), 0.40 (s, 18H).

Synthesis Example 19

Synthesis of Compound 19

Compound 19 was synthesized according to Reaction Scheme 19:

Reaction Scheme 19

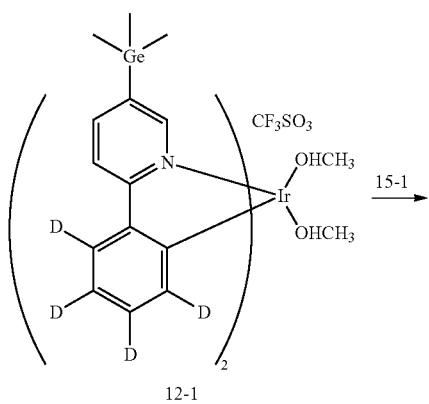

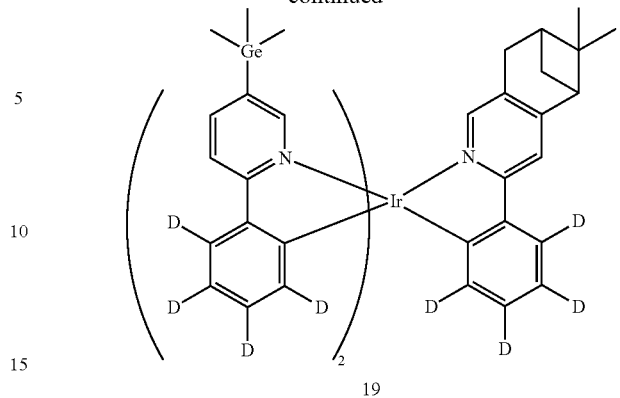

1) Synthesis of Compound 19

Compound 19 (yield of 30%) was synthesized in the same manner as Compound 1 in Synthesis Example 1, except that Intermediate 15-1 was used instead of Intermediate 1-1, and Intermediate 12-1 was used instead of Intermediate 1-2. The obtained compound was confirmed by LCMS and $^1$H NMR.

LC-MS m/z=996(M+H)$^+$.

$^1$H NMR (300 MHz, CDCl$_3$) δ=8.55 (s, 1H), 8.34 (s, 2H), 7.85 (d, 2H), 7.75 (s, 1H), 7.35 (d, 2H), 3.32 (br s, 1H), 2.35-2.30 (m, 3H), 2.02 (br s, 1H), 1.76 (br s, 1H), 0.98 (s, 6H), 0.39 (s, 18H).

Example 1

A glass substrate with ITO/Ag/ITO anode (70/1,000/70 Å) was cut to a size of 50 millimeters (mm)×50 mm×0.5 mm, ultrasonically cleaned with isopropyl alcohol and pure water for 5 minutes each, and exposed to ultraviolet (UV) light for 30 minutes and then ozone. The glass substrate was loaded into a vacuum deposition apparatus.

2-TNATA was deposited on the glass substrate to form a hole injection layer having a thickness of 600 Å, and then 4,4'-bis[N-(1-naphthyl)-N-phenylamino group]biphenyl (NPB) was deposited on the hole injection layer to form a hole transport layer having a thickness of 1,000 Å.

CBP and Compound 1 were co-deposited on the hole transport layer at a weight ratio of 91:9 to form an emission layer having a thickness of 250 Å. BCP was vacuum-deposited on the emission layer to form a hole blocking layer having a thickness of 50 Å. Alq$_3$ was deposited on the hole blocking layer to form an electron transport layer having a thickness of 350 Å, and LiF was vacuum-deposited on the electron transport layer to form an electron injection layer having a thickness of 10 Å, and then Mg and Ag were vacuum-deposited on the electron injection layer at a weight ratio of 90:10 to form an electrode having a thickness of 120 Å, thereby manufacturing an organic light-emitting device.

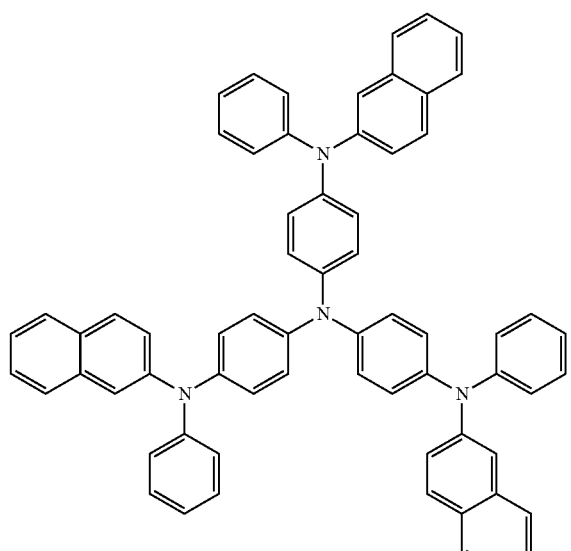

2-TNATA

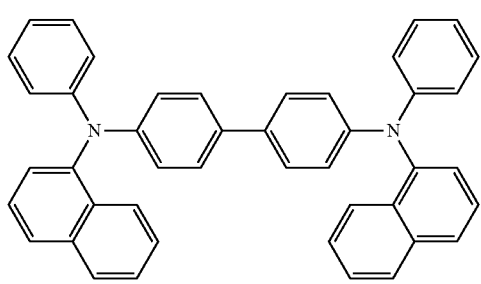

NPB

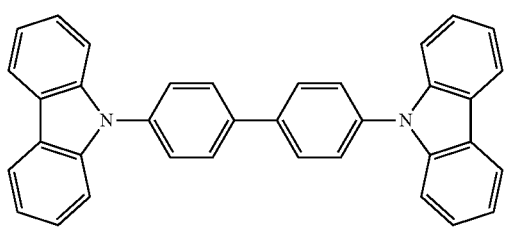

CBP

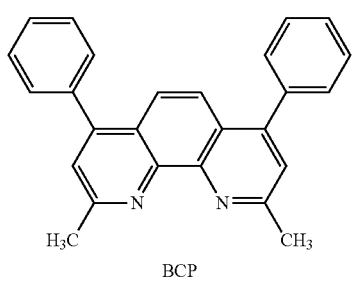

BCP

Example 2

An organic light-emitting device was manufactured in the same manner as in Example 1, except that, in forming an emission layer, Compound 2 was used instead of Compound 1.

Example 3

An organic light-emitting device was manufactured in the same manner as in Example 1, except that, in forming an emission layer, Compound 5 was used instead of Compound 1.

Example 4

An organic light-emitting device was manufactured in the same manner as in Example 1, except that, in forming an emission layer, Compound 6 was used instead of Compound 1.

Example 5

An organic light-emitting device was manufactured in the same manner as in Example 1, except that, in forming an emission layer, Compound 8 was used instead of Compound 1.

Example 6

An organic light-emitting device was manufactured in the same manner as in Example 1, except that, in forming an emission layer, Compound 10 was used instead of Compound 1.

Example 7

An organic light-emitting device was manufactured in the same manner as in Example 1, except that, in forming an emission layer, Compound 14 was used instead of Compound 1.

Example 8

An organic light-emitting device was manufactured in the same manner as in Example 1, except that, in forming an emission layer, Compound 16 was used instead of Compound 1.

Example 9

An organic light-emitting device was manufactured in the same manner as in Example 1, except that, in forming an emission layer, Compound 18 was used instead of Compound 1.

Comparative Example 1

An organic light-emitting device was manufactured in the same manner as in Example 1, except that, in forming an emission layer, Compound Ir(ppy)$_3$ described below was used instead of Compound 1.

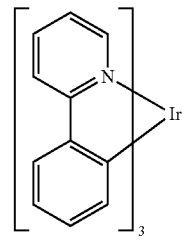

Irppy$_3$

Comparative Example 2

An organic light-emitting device was manufactured in the same manner as in Example 1, except that, in forming an emission layer, Compound A described below was used instead of Compound 1.

Compound A

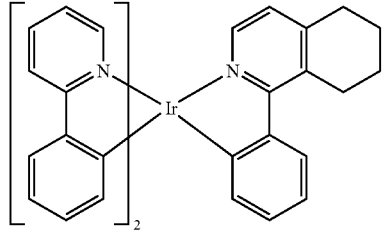

Comparative Example 3

An organic light-emitting device was manufactured in the same manner as in Example 1, except that, in forming an emission layer, Compound B described below was used instead of Compound 1.

Compound B

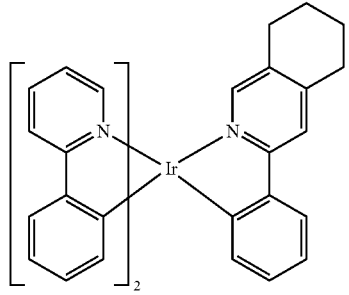

Comparative Example 4

An organic light-emitting device was manufactured in the same manner as in Example 1, except that, in forming an emission layer, Compound C described below was used instead of Compound 1.

Compound C

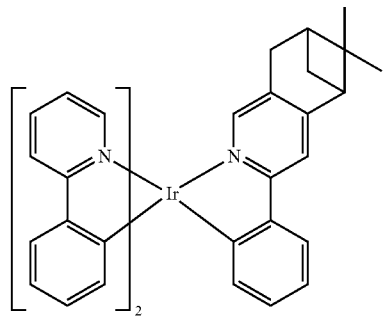

Evaluation Example 1

Driving voltage, current density, luminance, efficiency, emission color, color coordinate and lifetime were measured in Examples 1 to 9 and Comparative Examples 1 to 4 by using a current-voltage meter (Keithley 2400) and a luminance meter (Minolta Cs-1000A), and the results thereof are shown in Table 1 below. $LT_{97}$ refers to lifetime, which is the time elapsed before luminance reaches 97% of an initial luminance level:

TABLE 1

|  | host | dopant | driving voltage (V) | current density (Ma/cm$^2$) | luminance (cd/m$^2$) | efficiency (cd/A) | emission color | color coordinate | $LT_{97}$ (HR) |
|---|---|---|---|---|---|---|---|---|---|
| Example 1 | CBP | Compound 1 | 5.7 | 10 | 4,972 | 49.7 | green | 0.27, 0.70 | 75 |
| Example 2 | CBP | Compound 2 | 5.7 | 10 | 5,163 | 51.6 | green | 0.25, 0.71 | 81 |
| Example 3 | CBP | Compound 5 | 5.3 | 10 | 4,954 | 49.5 | green | 0.28, 0.71 | 70 |
| Example 4 | CBP | Compound 6 | 5.4 | 10 | 5,063 | 50.6 | green | 0.26, 0.70 | 85 |
| Example 5 | CBP | Compound 8 | 5.6 | 10 | 6,208 | 62.1 | green | 0.27, 0.72 | 94 |
| Example 6 | CBP | Compound 10 | 5.7 | 10 | 6,328 | 63.3 | green | 0.26, 0.71 | 87 |
| Example 7 | CBP | Compound 14 | 5.8 | 10 | 5,233 | 52.3 | green | 0.24, 0.70 | 98 |
| Example 8 | CBP | Compound 16 | 5.7 | 10 | 5,964 | 59.6 | green | 0.24, 0.72 | 68 |
| Example 9 | CBP | Compound 18 | 5.6 | 10 | 6,076 | 60.8 | green | 0.27, 0.71 | 90 |
| Comparative Example 1 | CBP | Ir(ppy)$_3$ | 6.8 | 10 | 4,255 | 42.6 | green | 0.25, 0.70 | 55 |
| Comparative Example 2 | CBP | Compound A | 5.7 | 10 | 4,896 | 49.0 | green | 0.28, 0.70 | 59 |
| Comparative Example 3 | CBP | Compound B | 5.7 | 10 | 5,091 | 50.9 | green | 0.26, 0.71 | 66 |
| Comparative Example 4 | CBP | Compound C | 5.7 | 10 | 4,958 | 49.6 | green | 0.26, 0.70 | 60 |

In addition, with respect to the driving voltages of the organic light-emitting devices according to Comparative Examples 1 to 4 and Examples 1 to 9, Examples 1 to 9 have excellent I-V-L characteristics. Accordingly, Examples 1 to 9 have an excellent efficiency and lifetime and better luminance than Comparative Examples 1 to 4. In detail, driving voltages of the organic light-emitting devices according to Examples 1 to 9 are decreased by 0.3 Volts (V) to 1.5 V from those of the organic light-emitting devices according to Comparative Examples 1 to 4.

Particularly, a compound according to an embodiment is used as a green phosphorescent dopant in Example 1. Thus, Example 1 has a better driving voltage, efficiency, and lifetime, which are 1.0 V lower, about 20% better, and more than 75% better, than Comparative Example 1, respectively. Example 1 also has a better lifetime, which is about 50% longer than Comparative Example 3.

As described above, according to the one or more of the above exemplary embodiments, the organometallic compound has excellent electric characteristics and thermal stability, and thus an organic light-emitting device including the organometallic compound may have low driving voltage, high efficiency, high luminance, long lifespan and high color purity.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the FIGURES, it will be understood by those of ordinary skill in the art that various changes in form and details may be made therein without departing from the spirit and scope as defined by the following claims.

What is claimed is:
1. An organometallic compound represented by Formula 1:

$$M(L_1)_{n1}(L_2)_{n2}(L_3)_{n3}$$ Formula 1

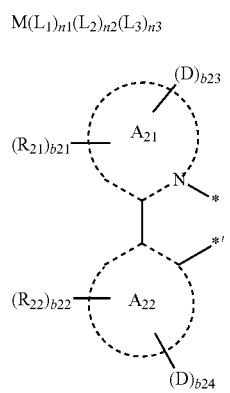

Formula 2

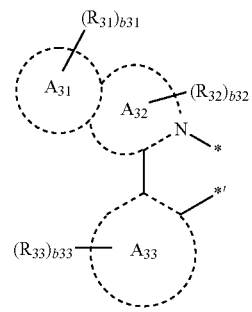

Formula 3 wherein, in Formulae 1, 2, and 3,
M is selected from a Period 1 transition metal, a Period 2 transition metal, and a Period 3 transition metal;
$L_1$ is a first ligand represented by Formula 2;
$L_2$ is a second ligand represented by Formula 3;
$L_3$ is selected from a monovalent organic ligand, a divalent organic ligand, and a trivalent organic ligand;
n1 and n2 are each independently an integer of 1 to 3, wherein when n1 is 2 or more, groups $L_1$ are identical or different, and when n2 is 2 or more, groups $L_2$ are identical or different;
n3 is an integer of 0 to 4, wherein when n3 is 2 or more, groups $L_3$ are identical or different;
$A_{21}$ and $A_{32}$ are each independently selected from a $C_1$-$C_{10}$ heterocycloalkane, a $C_1$-$C_{10}$ heterocycloalkene, a $C_1$-$C_{10}$ heteroarene, and a non-aromatic condensed heteropolycycle;
$A_{22}$ and $A_{33}$ are each independently selected from a $C_3$-$C_{10}$ cycloalkane, a $C_1$-$C_{10}$ heterocycloalkane, a $C_3$-$C_{10}$ cycloalkene, a $C_1$-$C_{10}$ heterocycloalkene, a $C_6$-$C_{10}$ arene, a $C_1$-$C_{10}$ heteroarene, a non-aromatic condensed polycycle, and a non-aromatic condensed heteropolycycle;
$A_{31}$ is selected from a $C_3$-$C_{20}$ cycloalkene and a $C_1$-$C_{10}$ heterocycloalkene;
$R_{21}$, $R_{22}$, and $R_{31}$ to $R_{33}$ are each independently selected from a hydrogen, a deuterium, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), —B($Q_6$)($Q_7$), and —Ge($Q_8$)($Q_9$)($Q_{10}$);
b21, b22, and b31 to b33 are each independently an integer of 1 to 4;
b23 and b24 are each independently an integer of 0 to 4, wherein the sum of b23 and b24 is 1 or more;

* and *' are each independently a binding site with M in Formula 1;

at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkenyl group, a $C_1$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$);

wherein $Q_1$ to $Q_{10}$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

2. The organometallic compound of claim 1, wherein M is Ir, Pt, Os, Ti, Zr, Hf, Eu, Tb, or Tm.

3. The organometallic compound of claim 1, wherein n1 is 2, n2 is 1, and n3 is 0.

4. The organometallic compound of claim 1, wherein $A_{21}$ and $A_{32}$ each independently are a pyrrole, an imidazole, a pyrazole, a thiazole, an isothiazole, an oxazole, an isoxazole, a triazole, a pyridine, a pyrazine, a pyrimidine, a quinoline, an isoquinoline, a benzoquinoline, a quinoxaline, a quinazoline, a naphthyridine, a benzoimidazole, a benzoxazole, an isobenzoxazole, an oxadiazole, or a triazine.

5. The organometallic compound of claim 1, wherein $A_{21}$ and $A_{32}$ each independently are a pyridine, a pyrazine, a pyrimidine, a quinoline, an isoquinoline, a quinoxaline, a quinazoline, or a naphthyridine.

6. The organometallic compound of claim 1, wherein $A_{22}$ and $A_{33}$ each independently are a benzene, a naphthalene, a fluorene, a spiro-fluorene, an indene, a furan, a thiophene, a carbazole, a benzofuran, a benzothiophene, a dibenzofuran, a dibenzothiophene, a pyrrole, an imidazole, a pyrazole, a thiazole, an isothiazole, an oxazole, an isoxazole, a triazole, a pyridine, a pyrazine, a pyrimidine, a quinoline, an isoquinoline, a benzoquinoline, a quinoxaline, a quinazoline, a naphthyridine, a benzoimidazole, a benzoxazole, an isobenzoxazole, an oxadiazole, or a triazine.

7. The organometallic compound of claim 1, wherein $A_{22}$ and $A_{33}$ each independently are a benzene, a naphthalene, a fluorene, a carbazole, a dibenzofuran, or a dibenzothiophene.

8. The organometallic compound of claim 1, wherein $A_{31}$ is a cyclopentene, a cyclohexene, a cycloheptene, a bicycloheptene, a dihydrofuran, a dihydropyran, or an oxabicycloheptene.

9. The organometallic compound of claim 1, wherein $A_{31}$ is a cyclopentene, a cyclohexane, or a bicycloheptene.

10. The organometallic compound of claim 1, wherein $R_{21}$, $R_{22}$, and $R_{31}$ to $R_{33}$ are each independently selected from a hydrogen, a deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{33}$)($Q_{34}$)($Q_{35}$); and —Si($Q_3$)($Q_4$)($Q_5$) and —Ge($Q_8$)($Q_9$)($Q_{10}$);

wherein $Q_3$ to $Q_5$, $Q_8$ to $Q_{10}$, and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group.

11. The organometallic compound of claim 1, wherein $L_1$ is a first ligand represented by one of Formulae 2-1 to 2-4:

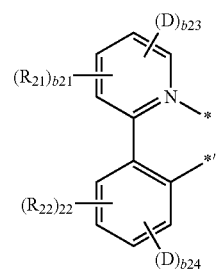

2-1

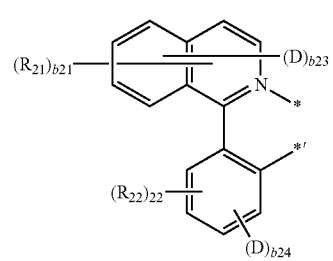

2-2

135
-continued

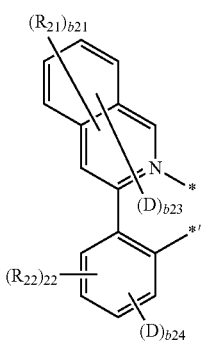
2-3

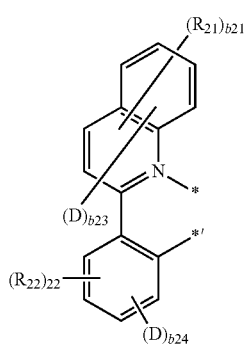
2-4 wherein, in Formulae 2-1 to 2-4,
D is deuterium, and
descriptions of $R_{21}$, $R_{22}$, b21, b22, b23, b24, *, and *' are the same as in claim 1.

12. The organometallic compound of claim 1, wherein $L_1$ is a first ligand represented by one of Formulae 2-31 to 2-34:

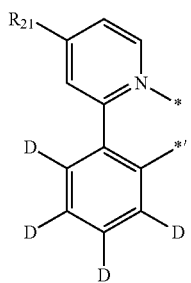
2-31

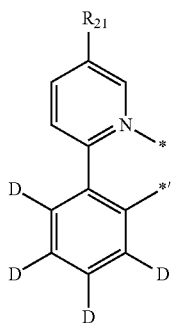
2-32

136
-continued

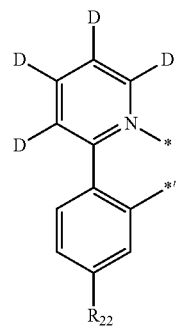
2-33

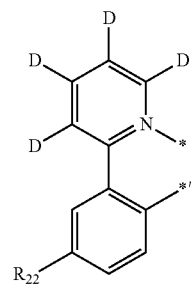
2-34 wherein, in Formulae 2-31 to 2-34,
D is deuterium, and
descriptions of $R_{21}$, $R_{22}$, *, and *' are the same as in claim 1.

13. The organometallic compound of claim 1, wherein $L_2$ is a second ligand represented by one of Formulae 3-1 to 3-15:

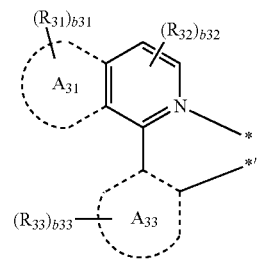
3-1

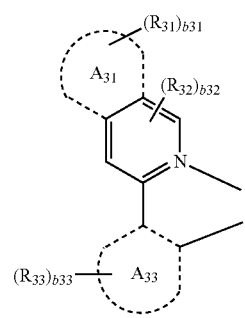
3-2

3-3 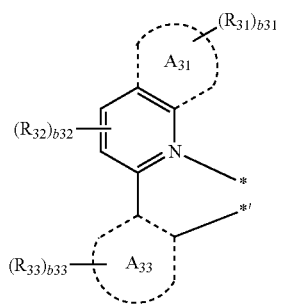
3-4 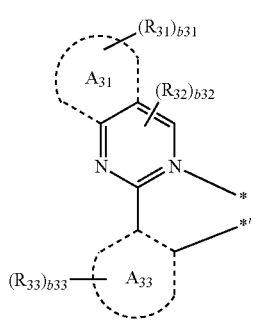
3-5 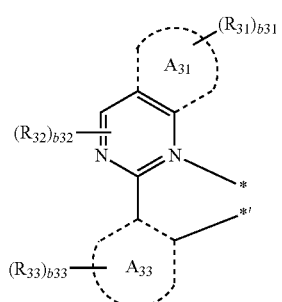
3-6 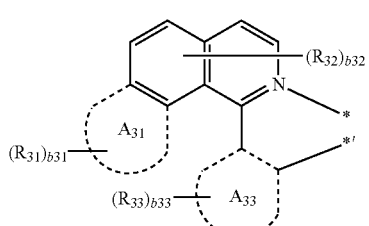
3-7 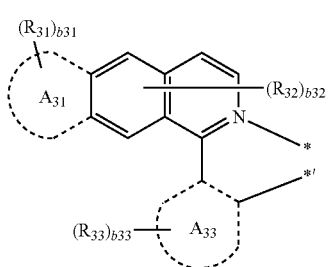
3-8 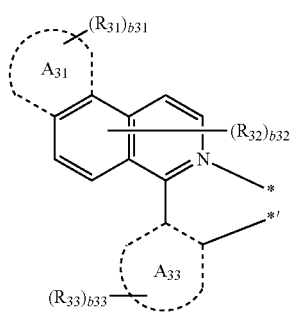
3-9 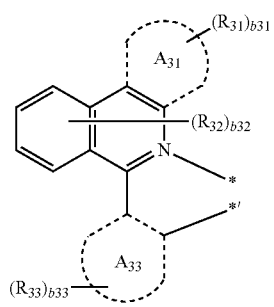
3-10 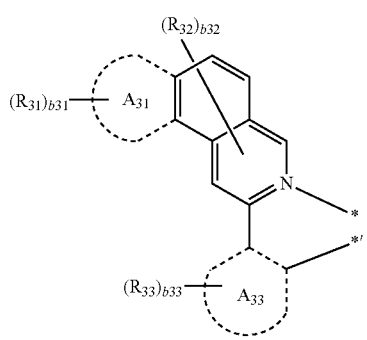
3-11 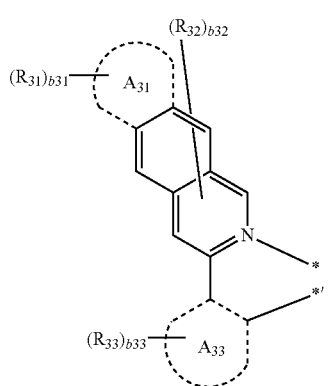

-continued
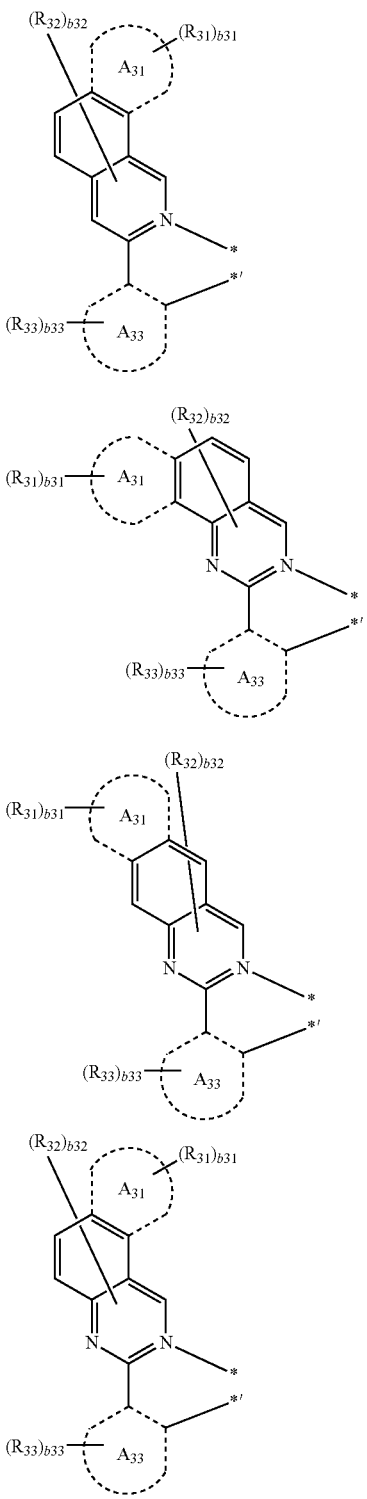
3-12
3-13
3-14
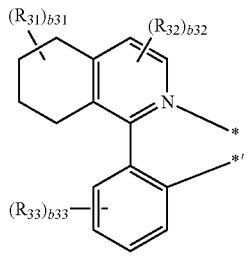
3-51
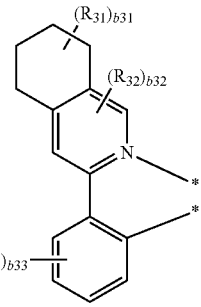
3-52
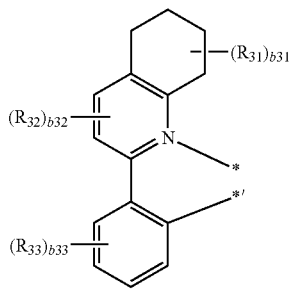
3-53
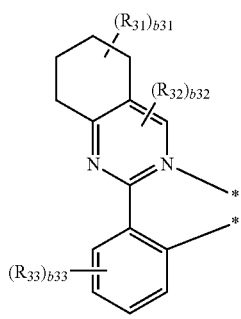
3-54
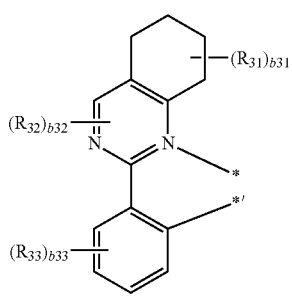
3-55
wherein, in Formulae 3-1 to 3-15,
descriptions of $A_{31}$, $A_{33}$, $R_{31}$ to $R_{33}$, b31 to b33, *and *' are the same as in claim 1.
14. The organometallic compound of claim 1, wherein $L_2$ is a second ligand represented by one of Formulae 3-51 to 3-65:

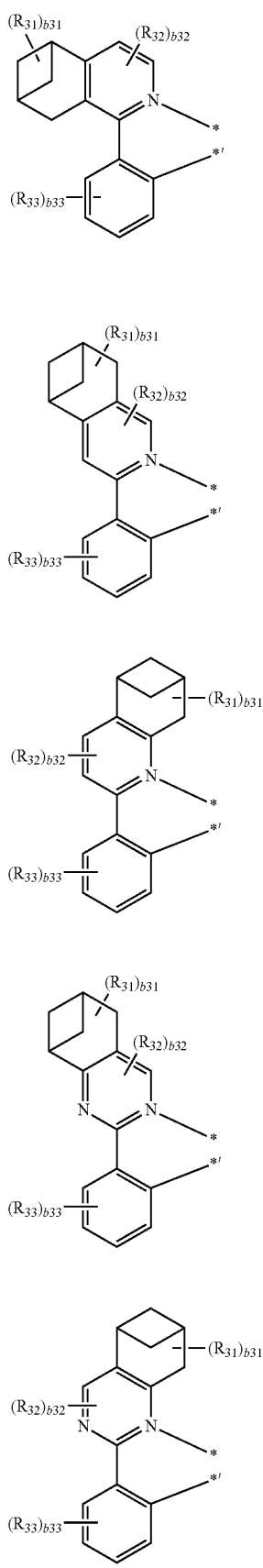
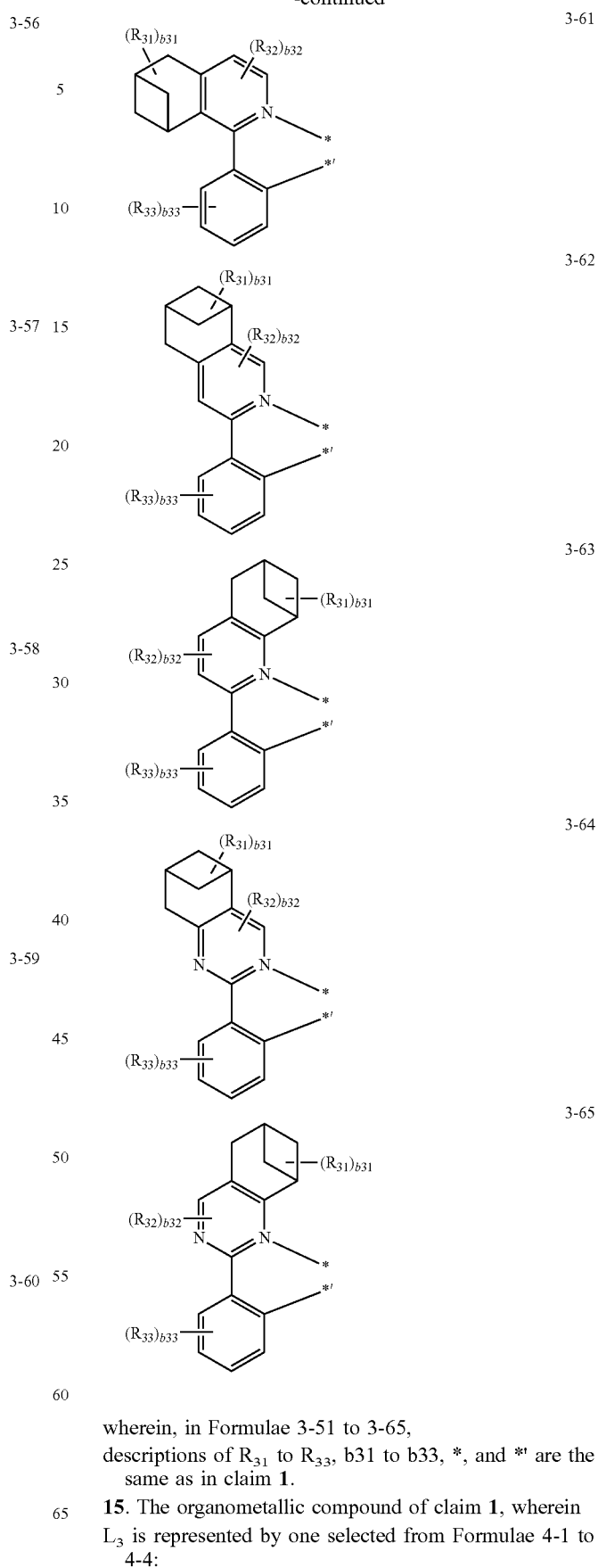
wherein, in Formulae 3-51 to 3-65,
descriptions of $R_{31}$ to $R_{33}$, b31 to b33, *, and *' are the same as in claim 1.
15. The organometallic compound of claim 1, wherein $L_3$ is represented by one selected from Formulae 4-1 to 4-4:

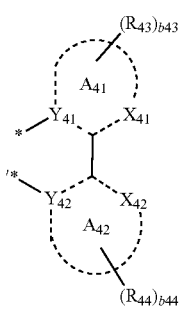

4-1

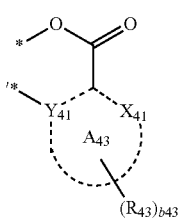

4-2

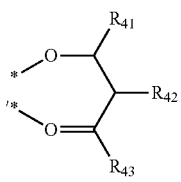

4-3

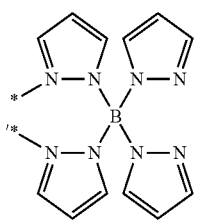

4-4 wherein, in Formulae 4-1 to 4-4, $X_{41}$ is $CR_{41}$ or N; $X_{42}$ is $CR_{42}$ or N;

$Y_{41}$ and $Y_{42}$ each independently are C or N;

$A_{41}$ to $A_{43}$ are each independently selected from a $C_3$-$C_{10}$ cycloalkane, a $C_1$-$C_{10}$ heterocycloalkane, a $C_3$-$C_{10}$ cycloalkene, a $C_1$-$C_{10}$ heterocycloalkene, a $C_6$-$C_{10}$ arene, a $C_1$-$C_{10}$ heteroarene, a non-aromatic condensed polycycle, and a non-aromatic condensed heteropolycycle;

$R_{41}$ to $R_{44}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_{41}$)($Q_{42}$)($Q_{43}$);

b43 and b44 each independently are an integer of 1 to 5;

$Q_{41}$ to $Q_{43}$ each independently are a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group; and

* and *' each independently are a binding site with M in Formula 1.

16. The organometallic compound of claim 1, wherein $L_3$ is represented by one selected from Formulae 5-1 to 5-119:

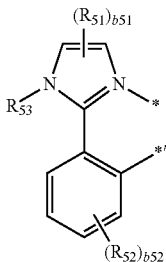

5-1

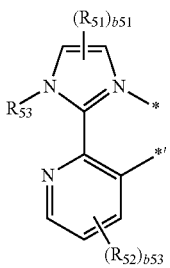

5-2

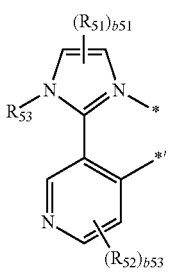

5-3

-continued
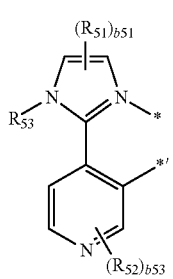
5-4
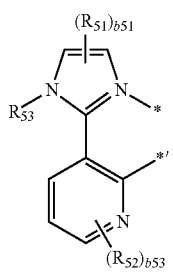
5-5
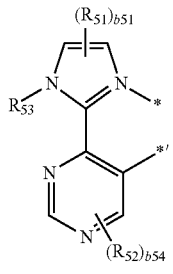
5-6
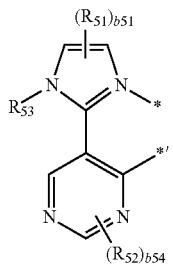
5-7
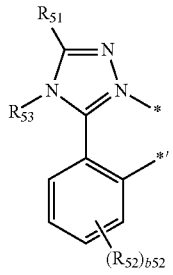
5-8
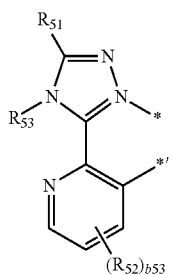
5-9
-continued
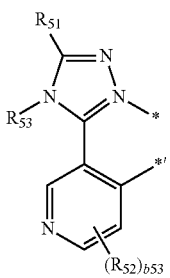
5-10
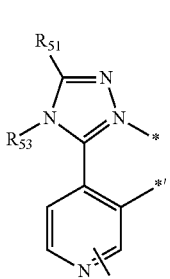
5-11
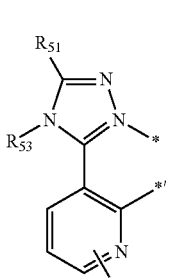
5-12
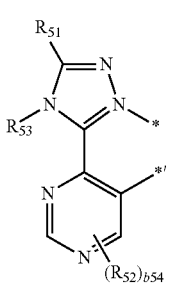
5-13
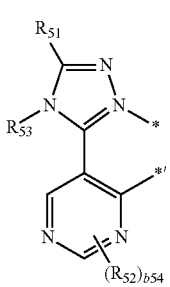
5-14

| | |
|---|---|
| 5-15 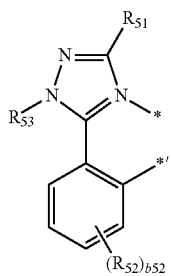 | 5-20 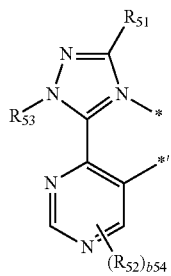 |
| 5-16 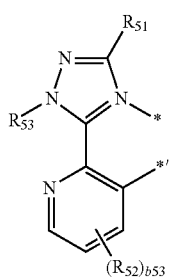 | 5-21 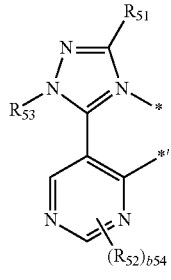 |
| 5-17 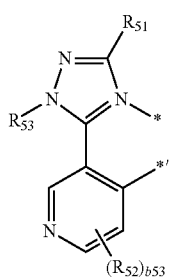 | 5-22 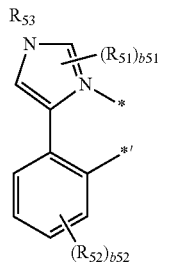 |
| 5-18 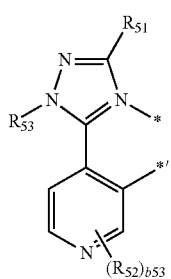 | 5-23 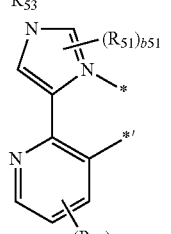 |
| | 5-24 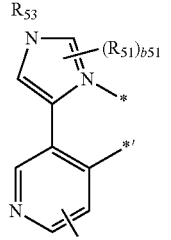 |
| 5-19 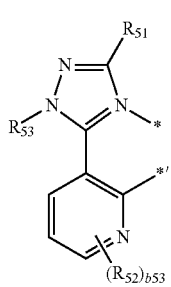 | 5-25 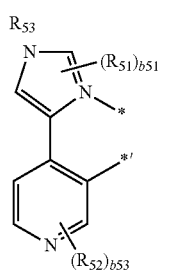 |

-continued
5-26
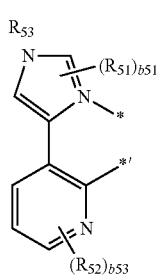
5-27
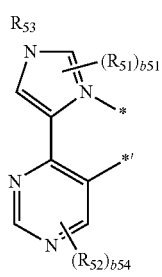
5-28
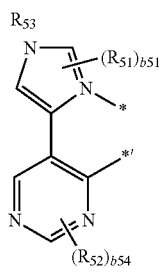
5-29
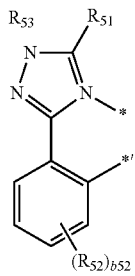
5-30
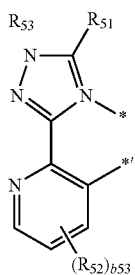
5-31
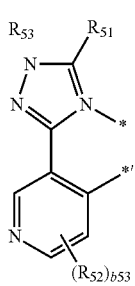
-continued
5-32
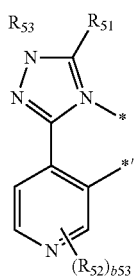
5-33
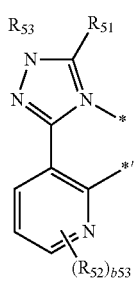
5-34
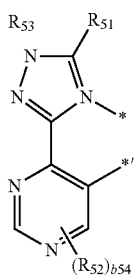
5-35
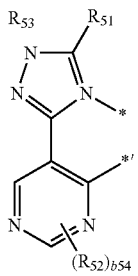
5-36
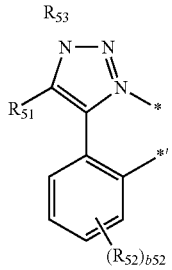

151
-continued
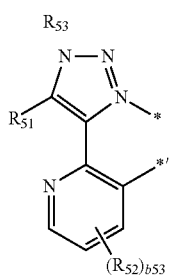
5-37
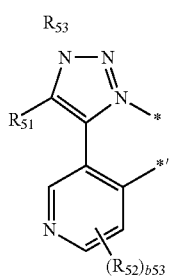
5-38
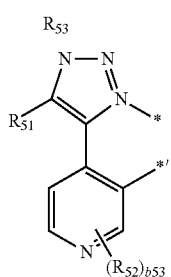
5-39
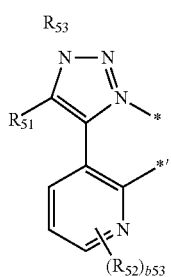
5-40
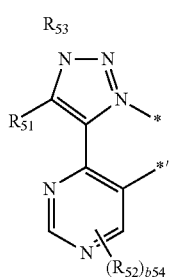
5-41
152
-continued
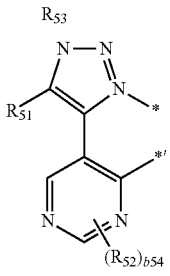
5-42
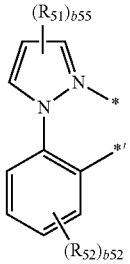
5-43
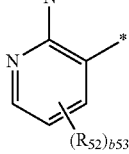
5-44
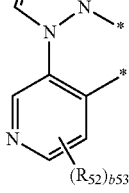
5-45
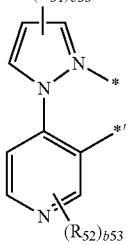
5-46
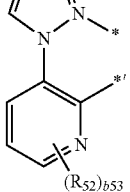
5-47

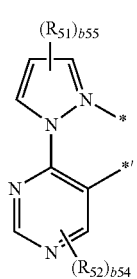
5-48
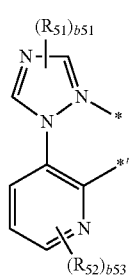
5-54
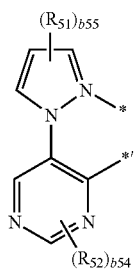
5-49
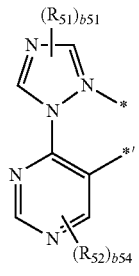
5-55
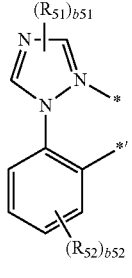
5-50
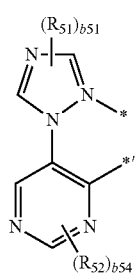
5-56
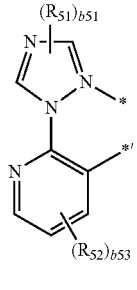
5-51
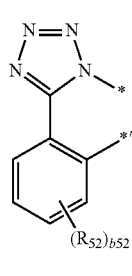
5-57
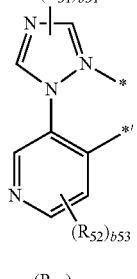
5-52
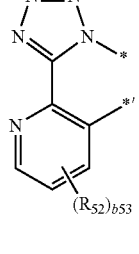
5-58
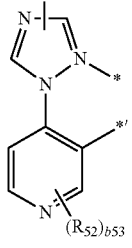
5-53
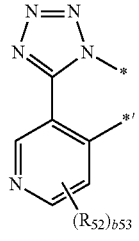
5-59

155
-continued
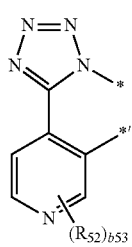
5-60
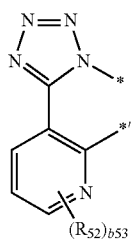
5-61
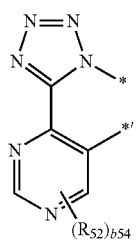
5-62
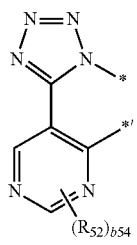
5-63
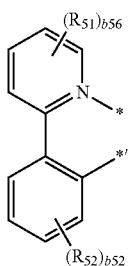
5-64
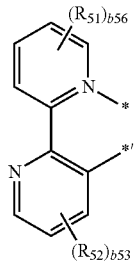
5-65
156
-continued
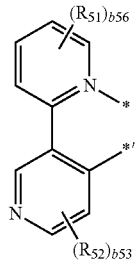
5-66
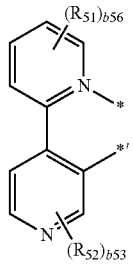
5-67
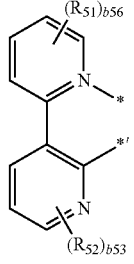
5-68
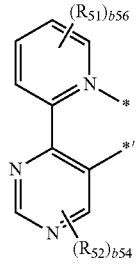
5-69
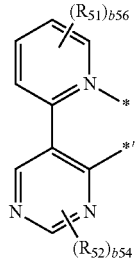
5-70
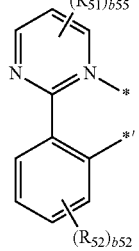
5-71

5-72 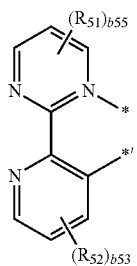
5-73 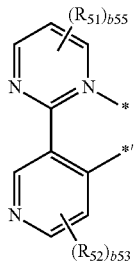
5-74 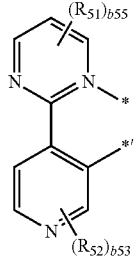
5-75 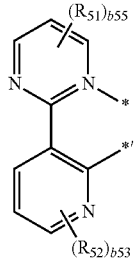
5-76 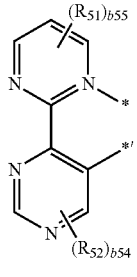
5-77 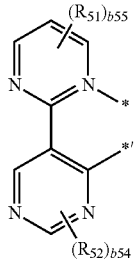
5-78 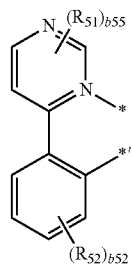
5-79 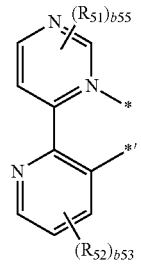
5-80 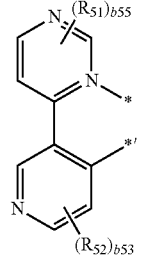
5-81 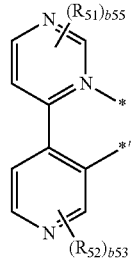
5-82 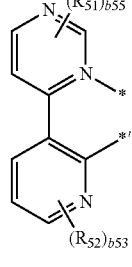
5-83 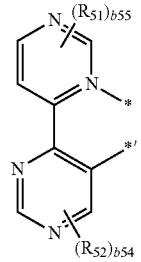

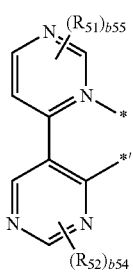 5-84
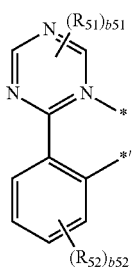 5-85
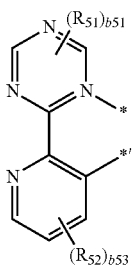 5-86
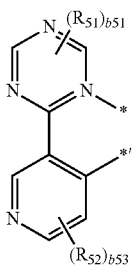 5-87
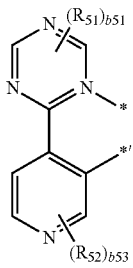 5-88
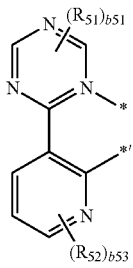 5-89
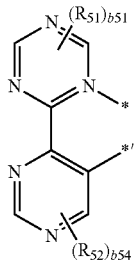 5-90
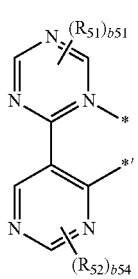 5-91
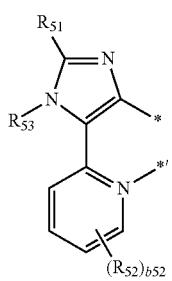 5-92
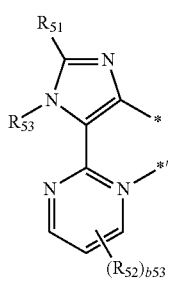 5-93
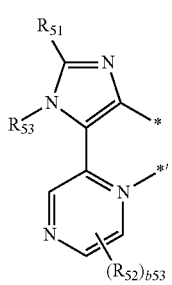 5-94

5-95 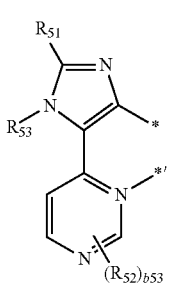
5-100 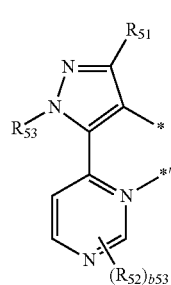
5-96 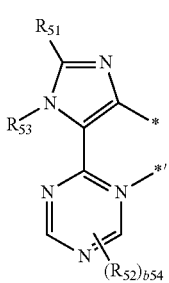
5-101 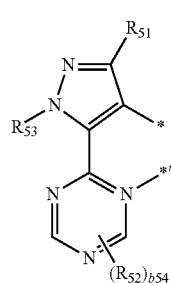
5-97 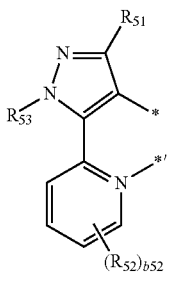
5-102 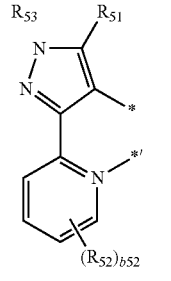
5-98 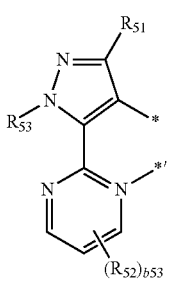
5-103 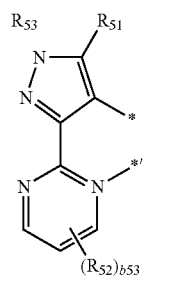
5-99 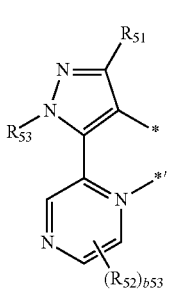
5-104

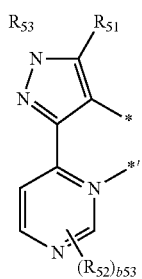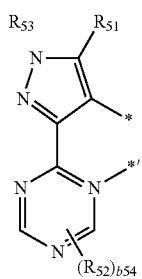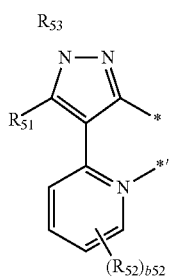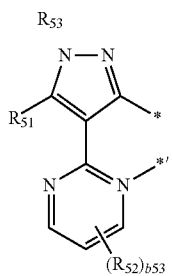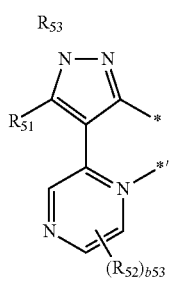
5-105
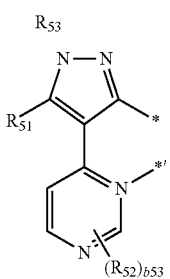
5-106
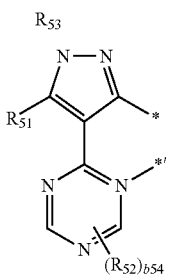
5-107
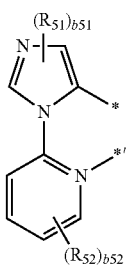
5-108
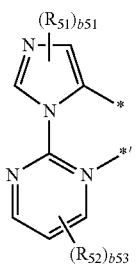
5-109
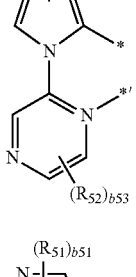
5-110
5-111
5-112
5-113
5-114
5-115

-continued

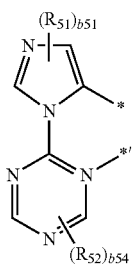

5-116

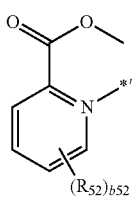

5-117

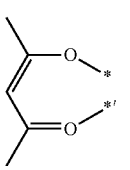

5-118

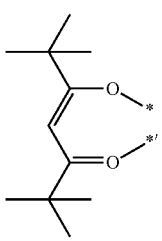

5-119 wherein, in Formulae 5-1 to 5-119,

R$_{51}$ to R$_{53}$ are each independently selected from a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an iso-butyl group, a sec-butyl group, a tert-butyl group, an n-pentyl group, an iso-pentyl group, a sec-pentyl group, a tert-pentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decanyl group, an iso-decanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group, each substituted with at least one selected from —F, a cyano group, and a nitro group;

b51 and b54 each independently are 1 or 2;

b53 and b55 each independently are an integer of 1 to 3;

b52 is an integer of 1 to 4; and

* and *' each independently are a binding site with M in Formula 1.

17. The organometallic compound of claim 1, wherein the organometallic compound is represented by Formula 1-1:

$$M(L_1)_{n1}(L_2)_{n2} \qquad \text{Formula 1-1}$$

wherein, in Formulae 1-1,

M is Os, Ir, or Pt;

L$_1$ is represented by one selected from Formulae 6-1 to 6-11;

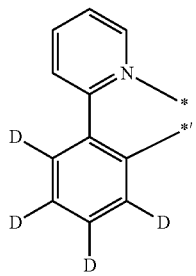

6-1

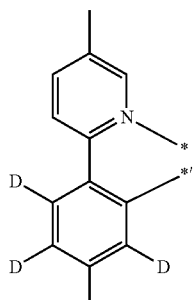

6-2

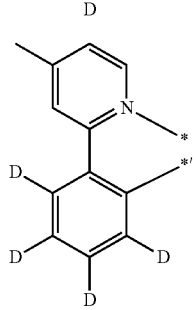

6-3

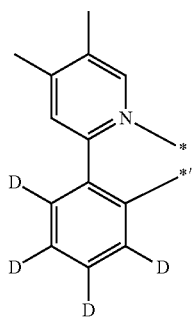
6-4
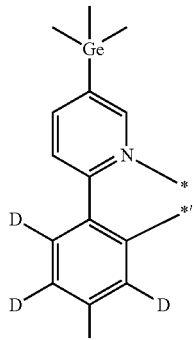
6-8
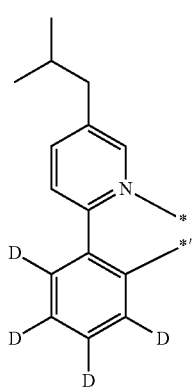
6-5
6-9
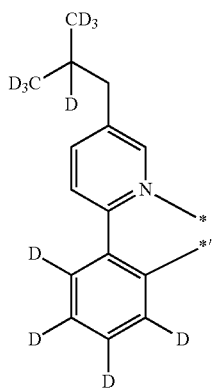
6-6
6-10
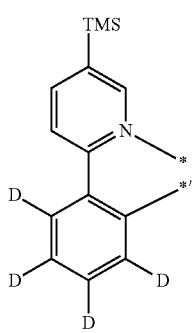
6-7
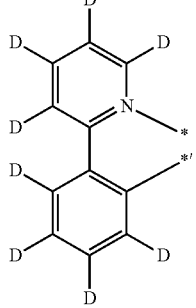
6-11
D is deuterium; n1 is 2; L₂ is represented by Formulae 7-1 to 7-16;
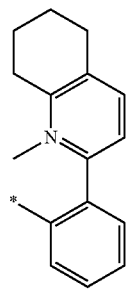
7-1

-continued
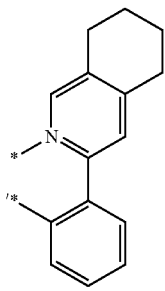
7-2
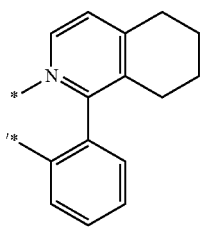
7-3
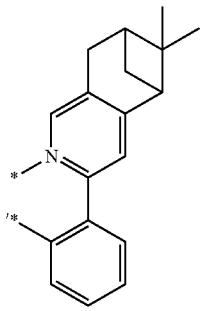
7-4
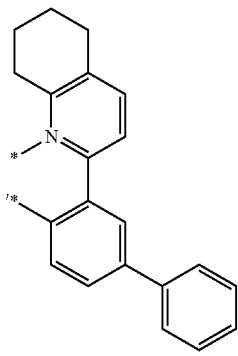
7-5
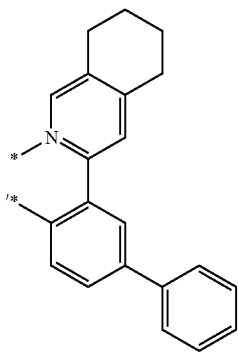
7-6
-continued
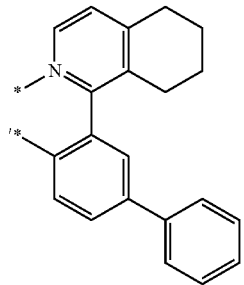
7-7
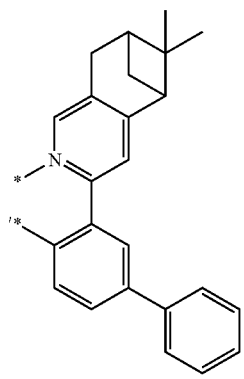
7-8
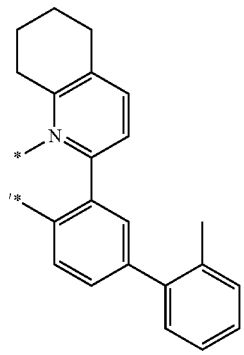
7-9
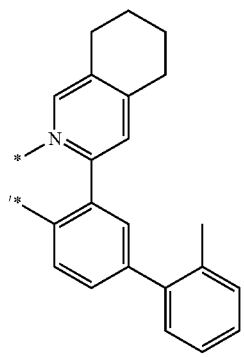
7-10

-continued
7-11 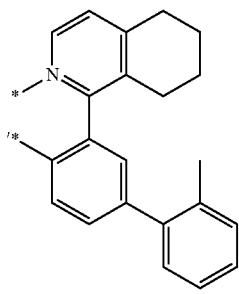
7-12 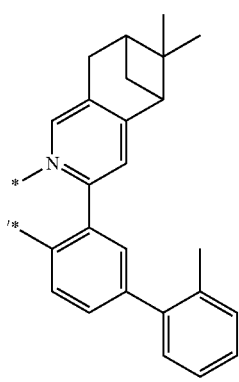
7-13 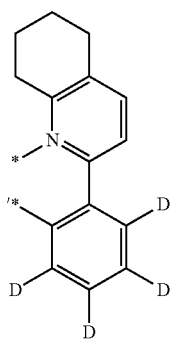
7-14 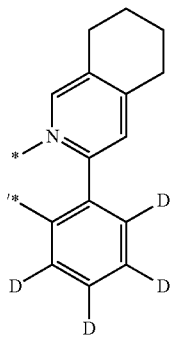
7-15 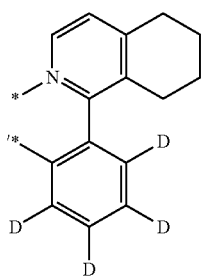
-continued
7-16 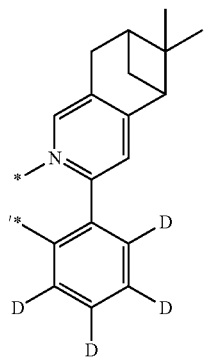
n2 is 1.
18. The organometallic compound of claim 1, wherein the organometallic compound is selected from Compounds 1 to 19:
1 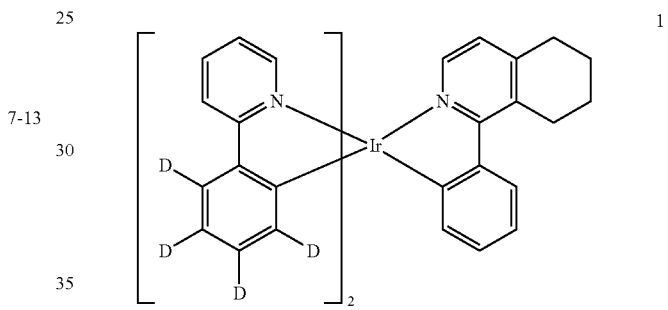
2 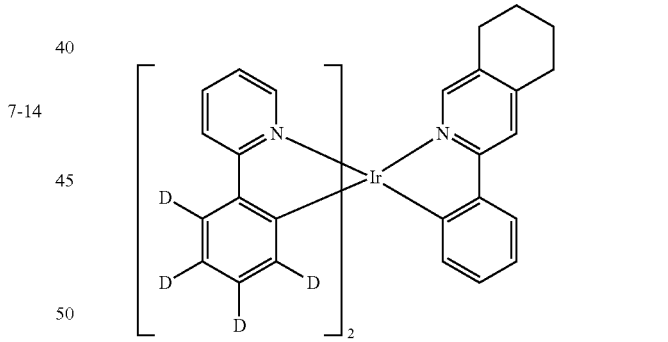
3 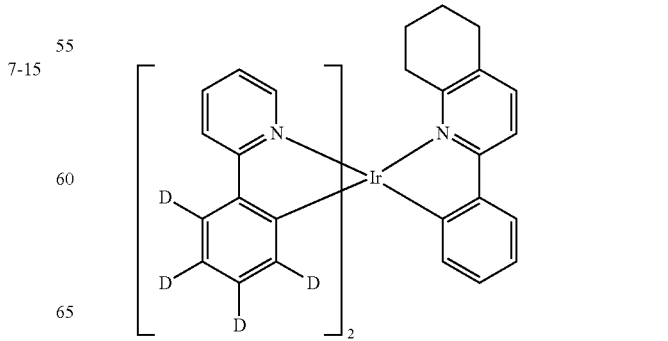

-continued
4
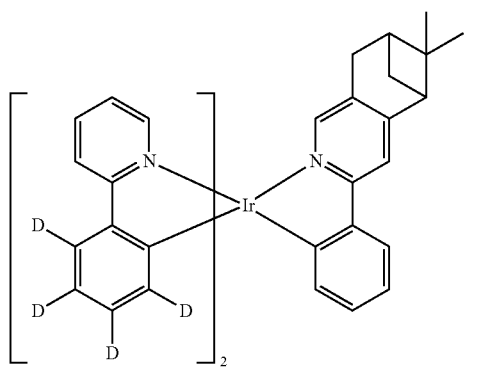
5
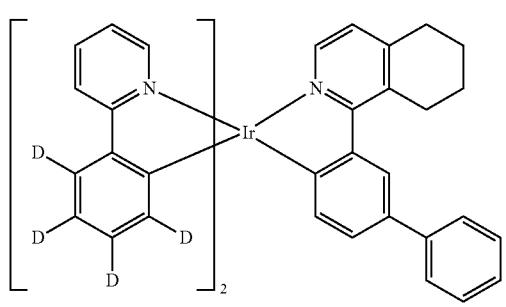
6
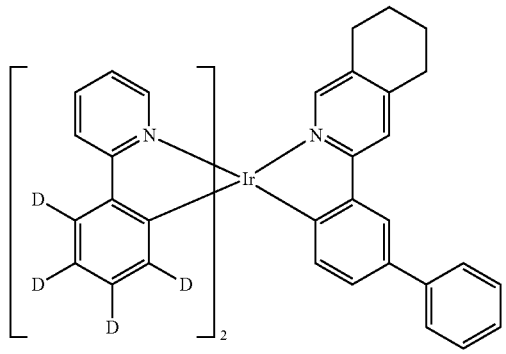
7
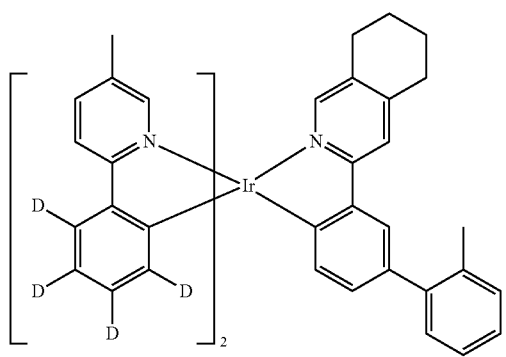
-continued
8
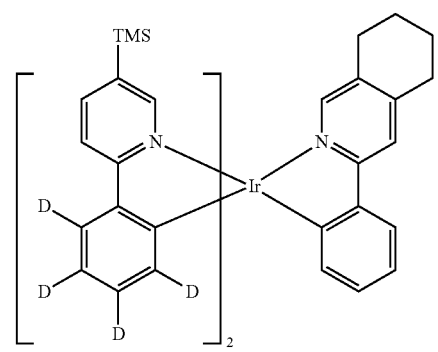
9
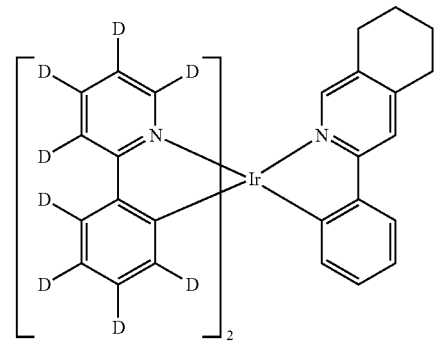
10
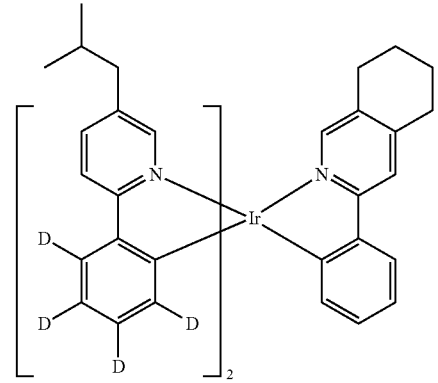
11
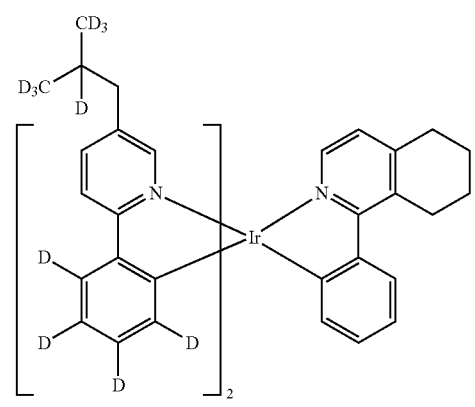

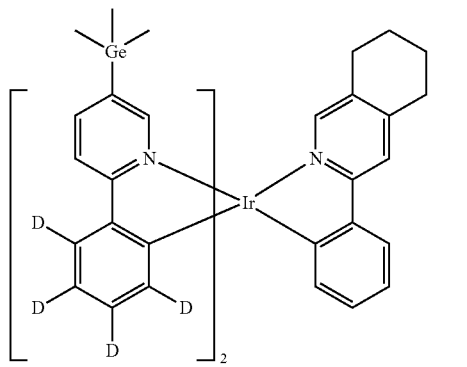
12
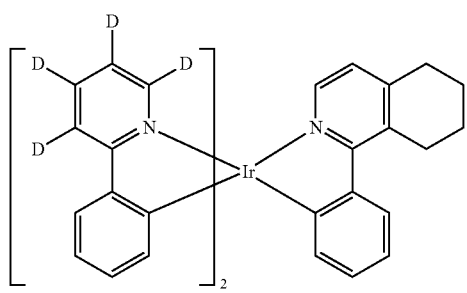
13
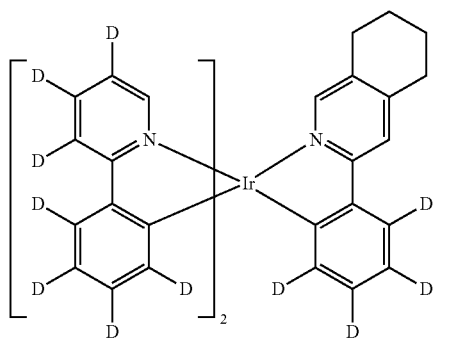
14
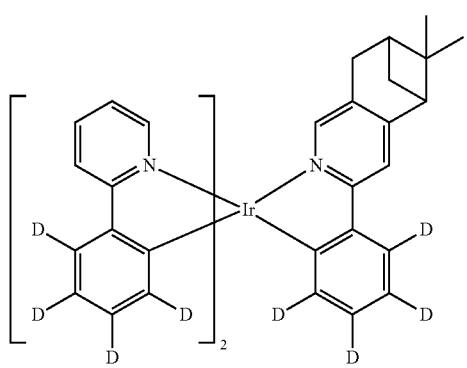
15
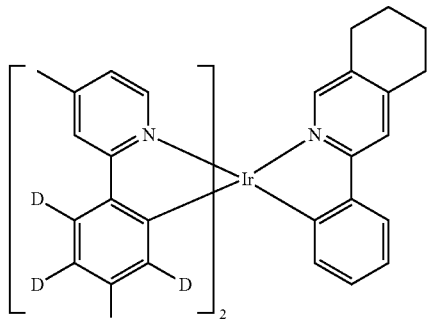
16
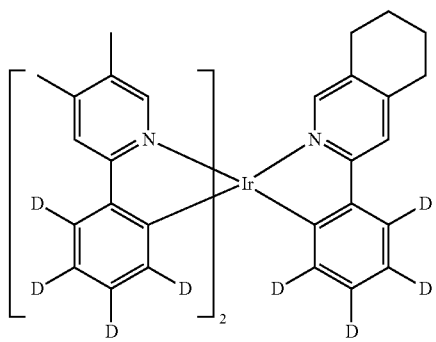
17
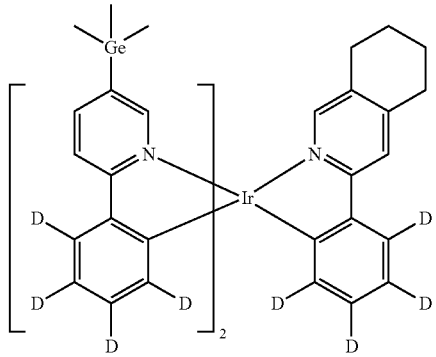
18
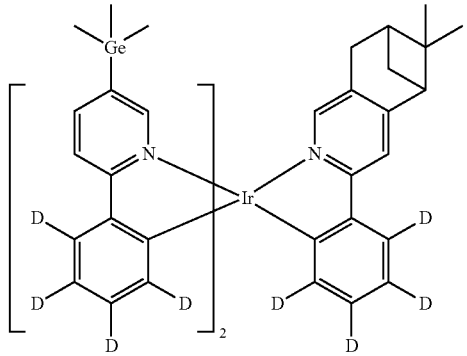
19
wherein, D is deuterium, and TMS in Compound 8 is —Si(CH$_3$)$_3$.
19. An organic light-emitting device comprising:
a first electrode;
a second electrode; and
an organic layer disposed between the first electrode and the second electrode,
wherein the organic layer comprises an emission layer and at least one organometallic compound of claim 1.

20. The organic light-emitting device of claim 19, wherein the emission layer comprises the organometallic compound of claim 1 and a host, wherein the amount of the organometallic compound of claim 1 is smaller than the amount of the host.

* * * * *